US008030459B2

(12) United States Patent
Papisov et al.

(10) Patent No.: US 8,030,459 B2
(45) Date of Patent: Oct. 4, 2011

(54) OXIME CONJUGATES AND METHODS FOR THEIR FORMATION AND USE

(75) Inventors: Mikhail I. Papisov, Winchester, MA (US); Alexander Yurkovetskiy, Littleton, MA (US)

(73) Assignee: The General Hospital Corporation, Boston, MA (US)

(*) Notice: Subject to any disclaimer, the term of this patent is extended or adjusted under 35 U.S.C. 154(b) by 148 days.

(21) Appl. No.: 10/521,334

(22) PCT Filed: Jul. 18, 2003

(86) PCT No.: PCT/US03/22584
§ 371 (c)(1),
(2), (4) Date: Oct. 27, 2005

(87) PCT Pub. No.: WO2004/009082
PCT Pub. Date: Jan. 29, 2004

(65) Prior Publication Data
US 2006/0058513 A1    Mar. 16, 2006

Related U.S. Application Data

(60) Provisional application No. 60/397,283, filed on Jul. 19, 2002.

(51) Int. Cl.
*C07K 14/47*    (2006.01)
*C07H 17/02*    (2006.01)
*C07D 207/36*    (2006.01)

(52) U.S. Cl. .............. 530/409; 536/17.4; 536/25.31; 548/518; 548/544

(58) Field of Classification Search .......... 530/409; 536/17.4; 548/518, 544
See application file for complete search history.

(56) References Cited

U.S. PATENT DOCUMENTS

| | | | |
|---|---|---|---|
| 5,075,222 A | 12/1991 | Hannum et al. | |
| 5,342,770 A | 8/1994 | Yamasaki | 435/178 |
| 5,582,172 A | 12/1996 | Papisov et al. | |
| 5,591,710 A | 1/1997 | Hsia | 514/6 |
| 5,605,791 A | 2/1997 | Ashkenazi et al. | 435/5 |
| 5,612,037 A * | 3/1997 | Huebner et al. | 424/194.1 |
| 5,624,803 A | 4/1997 | Noonberg et al. | |
| 5,780,243 A | 7/1998 | Thacker | 435/7 |
| 5,811,510 A | 9/1998 | Papisov | |
| 5,817,343 A | 10/1998 | Burke | |
| 5,824,784 A | 10/1998 | Kinstler et al. | |
| 5,863,990 A | 1/1999 | Papisov | |
| 5,945,293 A | 8/1999 | Siiman et al. | 435/7.24 |
| 5,958,398 A * | 9/1999 | Papisov | 424/78.08 |
| 6,048,837 A | 4/2000 | Friedman et al. | |
| 6,057,431 A | 5/2000 | Ishihara et al. | |
| 6,294,170 B1 | 9/2001 | Boone et al. | |
| 6,514,500 B1 | 2/2003 | Bridon et al. | 424/193.1 |
| 6,822,086 B1 | 11/2004 | Papisov | |
| 7,160,924 B2 | 1/2007 | Kinstler et al. | |
| 7,270,808 B2 | 9/2007 | Cheng et al. | |
| 2002/0082362 A1 | 6/2002 | Brocchini et al. | |
| 2002/0172689 A1 | 11/2002 | Scott | |
| 2004/0105840 A1 | 6/2004 | Kinstler et al. | |
| 2005/0169968 A1 | 8/2005 | Elmaleh et al. | |
| 2006/0019911 A1 | 1/2006 | Papisov | |
| 2006/0069230 A1 * | 3/2006 | Papisov | 528/220 |
| 2007/0190018 A1 | 8/2007 | Papisov | |
| 2008/0019940 A1 | 1/2008 | Papisov | |

FOREIGN PATENT DOCUMENTS

| | | |
|---|---|---|
| EP | 0280474 A2 | 8/1988 |
| EP | 0325270 A2 | 7/1989 |
| WO | WO 94/02068 | 2/1994 |
| WO | WO-9605309 A2 | 2/1996 |
| WO | WO 96/32419 | 10/1996 |
| WO | WO-9640912 A1 | 12/1996 |
| WO | WO 98/05363 | 2/1998 |
| WO | WO-98/05363 A2 | 2/1998 |
| WO | WO-9930561 A1 | 6/1999 |
| WO | WO-99/64595 A1 | 12/1999 |
| WO | WO-0078355 A2 | 12/2000 |
| WO | WO-0107486 A1 | 2/2001 |
| WO | WO-0110468 A2 | 2/2001 |
| WO | WO 02/067995 A1 | 9/2002 |
| WO | WO 02/087498 A2 | 11/2002 |
| WO | WO-03059988 A2 | 7/2003 |

OTHER PUBLICATIONS

Cervigni et al., Angew. Chem. Chem. Int. Engl., (1996), 35(11), pp. 1230-1232.*  G. Hermanson, Bioconjugate Techniques, pp. 552-569.*
K. Rose, J. Am. Chem. Soc. 1994, 116, 30-33.*
G. Hermanson, Bioconjugate Techniques, pp. 552-569, (1996). (provided before).*
International Search Report for PCT/US03/022584.

(Continued)

*Primary Examiner* — Yong Chu
(74) *Attorney, Agent, or Firm* — Choate Hall & Stewart LLP; Brenda Herschbach Jarrell; John P. Rearick

(57) ABSTRACT

The present invention relates to biodegradable biocompatible polyketals, methods for their preparation, and methods for creating animals by administration of biodegradable biocompatible polyketals. In one aspect, a method for forming the biodegradable biocompatible polyketals comprises combining a glycol-specific oxidizing agent with a polysaccharide to form an aldehyde intermediate, which is combined with a reducing agent to form the biodegradable biocompatible polyketal. The resultant biodegradable biocompatible polyketals can be chemically modified to incorporate additional hydrophilic moieties. A method for treating animals includes the administration of the biodegradable biocompatible polyketal in which biologically active compounds or diagnostic labels can be disposed. The present invention also relates to chiral polyketals, methods for their preparation, and methods for use in chromatographic applications, specifically in chiral separations. A method for forming the chiral polyketals comprises combining a glycol-specific oxidizing agent with a polysaccharide to form an aldehyde intermediate, which is combined with a suitable reagent to form the chiral polyketal. A method for use in chiral separations includes the incorporation of the chiral polyketals in the mobile phase during a chromatographic separation, or into chiral stationary phases such as gels. The present invention further relates to chiral polyketals as a source for chiral compounds, and methods for generating such chiral compounds.

23 Claims, 1 Drawing Sheet

OTHER PUBLICATIONS

Bieniarz, et al., "Extended Length Heterobifunctional Coupling Agents for Protein Conjugations", *Bioconjugate Chem.*; 7: 88-95, 1996.

Boeckler, et al., "Immunogenicity of New Heterobifunctional Cross-linking Reagents used in the Conjugation of Synthetic Peptides to liposomes", *Jour. of Immunological Methods* 191: 1-10, 1996.

Dubowchik, et al., "Monomethoxytrityl (MMT) as a Versatile Amino Protecting Group for Complex Prodrugs of Anticancer Compounds Sensitive to Strong Acids, Bases and Nucleophiles," *Tetrahedron Letters*, 38(30): 5257-5260, 1997.

Herrmann, et al., "Peptide-functionalized Polyphenylene Dendrimers," *Tetrahedron*, 59: 3925-3935, 2003.

Holtsberg, et al., "Poly(ethylene glycol) (PEG) conjugated arginine deiminase: effects of PEG formulations on its pharmacological properties," *Journal of Controlled Release*, 80: 259-271, 2002.

Liu et al., "Strategies for the synthesis of fluorescently labeled PNA," *Tetrahedron Letters*, 41: 6153-6156, 2000.

Pierce, "NHS-Esters-Maleimide Crosslinkers," www.piercenet.com/files/0438sm4.pdf, 2002.

Sharma, et al., "Maleimide-Assisted On-resin Macrocyclization," *Tetrahedron Letters*, 37(32): 5665-5668, 1996.

U.S. Appl. No. 12/620,855, Papisov et al.

Bendele et al., Short Communication: Renal Tubular Vacuolation in Animals Treated with Polyethylene-Glycol-Conjugated Proteins, Toxicological Sciences, 42: 152-157 (1997).

Bruneel D. et al. "Chemical modification of pullulan: 3. Succinoylation" Polymer, Elsevier Science Publishers B.V, GB, vol. 35, No. 12, Jun. 1, 1994, pp. 2656-2658.

Cervigni S. et al. "Synthesis of Glycopeptides and Lipopeptides by Chemoselective Ligation" Angew. Chem. Int. Ed. Egl. 1996, 35, No. 11, pp. 1230-1232.

Conover, C. et al. Physiological Effect of Polyethylene Glycol Conjugation on Stroma-Free Bovine Hemoglobin in the Conscious Dog After Partial Exchange Transfusion, Artificial Organs, vol. 21, No. 5, 1997, pp. 369-378.

Duncan, R. Polymer-Drug Conjugates. In: Handbook of Anticancer Drug Development, D. Budman, H. Calvert, and E. Rowinsky (Eds.), Lippincott, Williams & Wilkins Philadelphia (2003) pp. 239-260.

Endo et al. Nature of Linkage and Mode of Action of Methotrexate Conjugated with Antitumor Antibodies: Implications for Future Preparation of Conjugates. Cancer Research 48, 3330-3335, Jun. 15, 1988.

Feng et al. Synthesis and Evaluation of Water-Soluble Paclitaxel Prodrugs. Bioorganic & Medicinal Chemistry Letters 12 (2002) 3301-3303.

Gao Q. et al. "Drug-induced DNA repair: X-ray structure of a DNA-ditercalinium complex" Proc. Natl. Acad. Sci. USA vol. 88, pp. 2422-2426, Mar. 1991.

Hermanson G. Bioconjugate Techniques pp. 548-569 (1996).

Jordan, Craig V. Tamoxifen: A Most Unlikely Pioneering Medicine. Nature Reviews. vol. 2, Mar. 2003, 205-213.

Matysiak S. "Acetal Oligonucleotide Conjugates in Antisense Strategy" Nucleosides & Nucleotides, 16(5&6), pp. 855-861 (1997).

Papisov M.I. et al. "Semisynthetic Hydrophilic Polyals" Biomacromolecules 2005, vol. 6, pp. 2659-2670.

Pierce, NHS-Esters-Maleimide Crosslinkers, Jun. 27, 2002, pp. 1-8.

Tomlinson et al. Polyacetal-Doxorubicin Conjugates Designed for pH-Dependent Degradation. Bioconjugate Chem. 2003, 14, 1096-1106.

Zalipsky et al. Attachment of Drugs to Polyethylene Glycols. Eur. Polym. J. vol. 19, No. 12, pp. 1177-1183, 1983.

Conover, C. et al. Physiological Effect of Polyethylene Glycol Conjugation on Stroma-Free Bovine Hemoglobin in the Conscious Dog After Partial Exchange Transfusion, Artificial Organs, vol. 21, No. 5, 1997, pp. 369-378.

Endo et al. Nature of Linkage and Mode of Action of Methotrexate Conjugated with Antitumor Antibodies: Implications for Future Preparation of Conjugates. Cancer Research. (1988), 48, p. 3330-3335.

Feng et al. Bioorg. Med. Chem. Lett. (2002) 12, pp. 3301-3303.

Gao Q. et al. Drug-induced DNA repair: X-ray structure of a DNA-ditercalinium complex Proc. Natl. Acad. Sci. USA vol. 88, pp. 2422-2426, Mar. 1991 Biochemistry.

Jordan, V. C. Nature Reviews: Drug Discovery, Feb. 2003, p. 205-213.

Maeda, H et al. Conjugates of anticancer agents and polymers: advantages of macromolecular therapeutics in vivo. Bioconj. Chem. 1992, 3:351-362.

Matysiak S. Acetal Oligonucleotide Conjugates in Antisense Strategy Nucleosides & Nucleotides, 16(5&6), pp. 855-861 (1997).

Papisov M.I. et al. Semisynthetic Hydrophilic Polyals Biomacromolecules 2005, vol. 6, pp. 2659-2670.

Papisov, M et al. Fully biodegradable hydrophilic polyals (polyacetals and polyketals). 29th Int. Symp. on Controlled Release of Bioactive Materials, 2002, Seoul, Korea. Controlled Release Society, Deerfield, IL, 2002; paper # 465.

Papisov, M. (2001) Acyclic polyacetals from polysaccharides. (Biopolymers from polysaccharides and agroproteins), ACS Symposium Series 786, pp. 301-314.

Papisov, M. et al (1996) A long-circulating polymer with hydrolizable main chain. 23-rd International Symposium on Controlled Release of Bioactive Materials, Kyoto, Japan, 1996; Controlled Release Society, Deerfield, IL,; 107-108.

Papisov, M. et al. Fully biodegradable hydrophilic polyacetals for macromolecular radiopharmaceuticals. 49-th Annual Meeting of The Society of Nuclear Medicine, Los Angeles, CA, 2002. J. Nuc. Med. 2002, 43:5 (Supplement) p. 377P (abstract).

Papisov, M. et al. Hydrophilic Polyals: Biomimetic Biodegradable Stealth Materials for Pharmacology and Bioengineering. Proceedings of 226th Natl. Meeting of American Chemical Society, New York, NY, 2003.

Papisov, MI et al. (1998) Model cooperative (multivalent) vectors for drug targeting. 25th Int. Symp. on Controlled Release of Bioactive Materials, 1998, Las Vegas, Nevada, USA; Controlled Release Society, Deerfield, IL,170-171.

Papisov, MI. Modeling in vivo transfer of long-circulating polymers (two classes of long circulating polymers and factors affecting their transfer in vivo). Adv. Drug Delivery Rev., Special issue on long circulating drugs and drug carriers, 1995, 16:127-139.

Papisov, MI. Theoretical considerations of RES-avoiding liposomes: molecular mechanics and chemistry of liposome interactions. Adv. Drug Delivery Rev. 1998, 32:119-138.

Tomlinson et al. Polyacetal-doxorubicin conjugates designed for pH dependent degradation. Bioconjugate Chem., 2003, 14(6), 1096-1106.

Yurkovetskiy, A. et al. Biodegradable polyal carriers for protein modification. 29th Int. Symp. on Controlled Release of Bioactive Materials, 2002, Seoul, Korea. Controlled Release Society, Deerfield, IL, 2002; paper # 357.

Yurkovetskiy, A. et al. Biodegradable polyals for protein modification. Controlled Release Society's Winter Symposium, Salt Lake City, Utah, 2003.

Yurkovetsky, A. et al., Fully Degradable Hydrophilic Polyals for Protein Modification. Biomacromolecules 2005, 6, 2648-2658.

Zalipsky et al. Eur. Polym. J. (1983), vol. 19, No. 12, p. 1177-1183.

Mett, H. et al., Cancer Chemother Pharmacol., vol. 32, pp. 39-45 (1993).

* cited by examiner

OXIME CONJUGATES AND METHODS FOR THEIR FORMATION AND USE

PRIORITY CLAIM

The present application claims the benefit under 35 U.S.C. 371 of International Application No.: PCT/US03/33584 (published PCT application No. WO 04/09082), filed Jul. 18, 2003, which claims priority to U.S. Patent Application No. 60/397,283, filed Jul. 19, 2002, the entire contents of each of the above cited applications are incorporated herein by reference.

GOVERNMENT FUNDING

The present invention was made with support, in part, from a grant from the National Center for Research Resources of the National Institutes of Health (Number R21-RR14221) and a DoE grant (Number DE-FG02-00ER63057). Accordingly, the United States Government may have certain rights in this invention.

A portion of the disclosure of this patent document contains material which is subject to copyright protection. The copyright owner has no objection to the facsimile reproduction by any-one of the patent document or the patent disclosure, as it appears in the Patent and Trademark Office patent file or records, but otherwise reserves all copyright rights whatsoever.

BACKGROUND OF THE INVENTION

Traditionally, pharmaceuticals have primarily consisted of small molecules that are dispensed orally (as solid pills and liquids) or as injectables. Over the past three decades, however, sustained release formulations (i.e., compositions that control the rate of drug delivery and allows delivery of the therapeutic agent at the site where it is needed) have become increasingly common and complex. Nevertheless, many questions and challenges regarding the development of new treatments as well as the mechanisms with which to administer them remain to be addressed.

Although considerable research efforts in this area have led to significant advances, drug delivery methods/systems that have been developed over the years and are currently used, still exhibit specific problems that require some investigating. For example, many drugs exhibit limited or otherwise reduced potencies and therapeutic effects because of they are generally subject to partial degradation before they reach a desired target in the body. Once administered, sustained release medications deliver treatment continuously, e.g. for days or weeks, rather than for a short period of time (hours or minutes). Furthermore, orally administered therapeutics are generally preferable over injectable medications, which are often more expensive and are more challenging to administer, and thus it would be highly desirable if injectable medications could simply be dosed orally. However, this goal cannot be achieved until methods are developed to safely shepherd drugs through tissue barriers, such as epithelial or dermal barriers, or specific areas of the body, such as the stomach, where low pH can degrade or destroy a medication, or through an area where healthy tissue might be adversely affected.

One objective in the field of drug delivery systems, therefore, is to deliver medications intact to specifically targeted areas of the body through a system that can control the rate and time of administration of the therapeutic agent by means of either a physiological or chemical trigger. Over the past decade, materials such as polymeric microspheres, polymer micelles, soluble polymers and hydrogel-type materials have been shown to be effective in enhancing drug targeting specificity, lowering systemic drug toxicity, improving treatment absorption rates, and providing protection for pharmaceuticals against biochemical degradation, and thus have shown great potential for use in biomedical applications, particularly as components of drug delivery devices.

The design and engineering of biomedical polymers (e.g., polymers for use under physiological conditions) are generally subject to specific and stringent requirements. In particular, such polymeric materials must be compatible with the biological milieu in which they will be used, which often means that they show certain characteristics of hydrophilicity. They also have to demonstrate adequate biodegradability (i.e., they degrade to low molecular weight species. The polymer fragments are in turn metabolized in the body or excreted, leaving no trace).

Biodegradability is typically accomplished by synthesizing or using polymers that have hydrolytically unstable linkages in the backbone. The most common chemical functional groups with this characteristic are esters, anhydrides, orthoesters, and amides. Chemical hydrolysis of the hydrolytically unstable backbone is the prevailing mechanism for the polymer's degradation. Biodegradable polymers can be either natural or synthetic. Synthetic polymers commonly used in medical applications and biomedical research include polyethyleneglycol (pharmacokinetics and immune response modifier), polyvinyl alcohol (drug carrier), and poly(hydroxypropylmetacrylamide) (drug carrier). In addition, natural polymers are also used in biomedical applications. For instance, dextran, hydroxyethylstarch, albumin and partially hydrolyzed proteins find use in applications ranging from plasma substitute, to radiopharmaceutical to parenteral nutrition. In general, synthetic polymers may offer greater advantages than natural materials in that they can be tailored to give a wider range of properties and more predictable lot-to-lot uniformity than can materials from natural sources. Synthetic polymers also represent a more reliable source of raw materials, one free from concerns of infection or immunogenicity. Methods of preparing polymeric materials are well known in the art. However, synthetic methods that successfully lead to the preparation of polymeric materials that exhibit adequate biodegradability, biocompatibility, hydrophilicity and minimal toxicity for biomedical use are scarce. The restricted number and variety of biopolymers currently available attest to this.

Therefore a need exists in the biomedical field for low-toxicity, biodegradable, biocompatible, hydrophilic polymer conjugates comprising pharmaceutically useful modifiers, which overcome or minimize the above-referenced problems. Such polymer conjugates would find use in several applications, including components for biomedical preparations, pharmaceutical formulations, medical devices, implants, and the packaging/delivery of therapeutic, diagnostic and prophylatic agents.

SUMMARY OF THE INVENTION

The present invention discloses a polymer conjugate that is biodegradable, biocompatible and exhibits little toxicity and/or bioadhesivity in vivo, and contains one or more modifiers covalently attached to the polymer via oxime-containing linkages.

In one aspect, the invention encompasses a conjugate comprising a carrier substituted with one or more occurrences of a moiety having the structure:

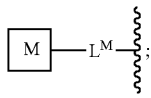

wherein each occurrence of M is independently a modifier; and each occurrence of $L^M$ is independently an oxime-containing linker.

In certain embodiments, each occurrence of $L^M$ is independently a moiety having the structure:

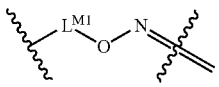

wherein each occurrence of $L^{M1}$ is independently a substituted or unsubstituted, cyclic or acyclic, linear or branched $C_{0-12}$alkylidene or $CO_{12}$ alkenylidene moiety wherein up to two non-adjacent methylene units are independently optionally replaced by CO, $CO_2$, COCO, $CONR^{Z1}$, $OCONR^{Z1}$, $NR^{Z1}NR^{Z2}$, $NR^{Z1}NR^{Z2}CO$, $NR^{Z1}CO$, $NR^{Z1}CO_2$, $NR^{Z1}CONR^{Z2}$, SO, $SO_2$, $NR^{Z1}SO_2$, $SO_2NR^{Z1}$, $NR^{Z1}SO_2NR^{Z2}$, O, S, or $NR^{Z1}$; wherein each occurrence of $R^{Z1}$ and $R^{Z2}$ is independently hydrogen, alkyl, heteroalkyl, aryl, heteroaryl or acyl.

In certain other embodiments, one or more occurrences of $L^{M1}$ independently comprises a maleimide- or N-hydroxysuccinimide ester-containing crosslinker. In yet other embodiments, one or more occurrences of $L^{M1}$ independently comprises a 4-(N-maleimidomethyl)cyclohexane-1-carboxylate, m-maleimidobenzoyl or a 4-(p-maleimidophenyl) butyrate crosslinker.

In certain other embodiment, one or more occurrences of M comprises, or is attached to the carrier through, a biodegradable bond. In certain exemplary embodiments, the biodegradable bond is selected from the group consisting of acetal, ketal, amide, ester, thioester, enamine, imine, imide, dithio, and phosphoester bond.

In certain other embodiments, the carrier is a hydrophilic biodegradable polymer selected from the group consisting of carbohydrates, glycopolysaccharides, glycolipids, glycoconjugates, polyacetals, polyketals, and derivatives thereof. In certain exemplary embodiments, the carrier is a naturally occurring linear and branched biodegradable biocompatible homopolysaccharide selected from the group consisting of cellulose, amylose, dextran, levan, fucoidan, carraginan, inulin, pectin, amylopectin, glycogen and lixenan. In certain other exemplary embodiments, the carrier is a naturally occurring linear and branched biodegradable biocompatible heteropolysaccharide selected from the group consisting of agarose, hyluronan, chondroitinsulfate, dermatansulfate, keratansulfate, alginic acid and heparin. In yet other exemplary embodiments, the carrier is a hydrophilic polymer selected from the group consisting of polyacrylates, polyvinyl polymers, polyesters, polyorthoesters, polyamides, polypeptides, and derivatives thereof. In still other exemplary embodiments, the carrier is a biodegradable biocompatible polyacetal wherein at least a subset of the polyacetal repeat structural units have the following chemical structure:

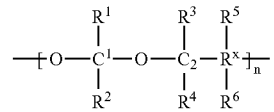

wherein for each occurrence of the n bracketed structure, one of $R^1$ and $R^2$ is hydrogen, and the other is a biocompatible group and includes a carbon atom covalently attached to $C^1$; $R^x$ includes a carbon atom covalently attached to $C^2$; n is an integer; each occurrence of $R^3$, $R^4$, $R^5$ and $R^6$ is a biocompatible group and is independently hydrogen or an organic moiety; and for each occurrence of the bracketed structure n, at least one of $R^1$, $R^2$, $R^3$, $R^4$, $R^5$ and $R^6$ comprises a carbonyl group suitable for oxime formation. In further exemplary embodiments, the carrier is a biodegradable biocompatible polyketal wherein at least a subset of the polyketal repeat structural units have the following chemical structure:

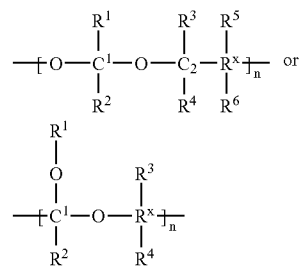

wherein each occurrence of $R^1$ and $R^1$ is a biocompatible group and includes a carbon atom covalently attached to $C^1$; $R^x$ includes a carbon atom covalently attached to $C^2$; n is an integer; each occurrence of $R^3$, $R^1$, $R^5$ and $R^6$ is a biocompatible group and is independently hydrogen or an organic moiety; and for each occurrence of the bracketed structure n, at least one of $R^1$, $R^2$, $R^3$, $R^4$, $R^5$ and $R^6$ comprises a carbonyl group suitable for oxime formation.

In other embodiments, in the conjugates of the invention, one or more occurrences of M comprise a biologically active modifier. In certain exemplary embodiments, one or more occurrence of M is selected from the group consisting of proteins, antibodies, antibody fragments, peptides, antineoplastic drugs, hormones, cytokines, enzymes, enzyme substrates, receptor ligands, lipids, nucleotides, nucleosides, metal complexes, cations, anions, amines, heterocycles, heterocyclic amines, aromatic groups, aliphatic groups, intercalators, antibiotics, antigens, immunomodulators, and antiviral compounds.

In certain other embodiments, one or more occurrence of M comprises a detectable label. In certain exemplary embodiments, one or more occurrence of M comprises atoms or groups of atoms comprising radioactive, paramagnetic, superparamagnetic, fluorescent, or light absorbing structural domains.

In certain other embodiments, one or more occurrences of M comprise a diagnostic label. In certain exemplary embodiments, one or more occurrence of M comprises radiopharmaceutical or radioactive isotopes for gamma scintigraphy and PET, contrast agent for Magnetic Resonance Imaging (MRI), contrast agent for computed tomography, contrast agent for X-ray imaging method, agent for ultrasound diagnostic method, agent for neutron activation, moiety which can reflect, scatter or affect X-rays, ultrasounds, radiowaves, microwaves and/or fluorophores.

In certain embodiments, the conjugates of the invention are water-soluble. In certain exemplary embodiments, the inventive conjugate comprises a biologically active modifier and a detectable label.

In certain embodiments, the carrier is a linear macromolecule, a branched macromolecule, a globular macromolecule, a graft copolymer, a comb copolymer, a nanoparticle or a lipid-based carrier. In certain exemplary embodiments, the lipid-based carrier is a liposome.

In another aspect, the invention encompasses compounds having the structure $R^{N1}R^{N2}N$—O-$L^1$; wherein $R^1$ and $R^{N2}$ are independently hydrogen, an aliphatic, alicyclic, heteroaliphatic, heterocyclic, aryl or heteroaryl moiety, or a nitrogen protecting group, or $R^{N1}$ and $R^{N2}$, taken together with the nitrogen atom to which they are attached, form a substituted or unsubstituted heterocyclic or heteroaryl moiety; and $L^1$ is an aliphatic, alicyclic, heteroaliphatic, heterocyclic, aryl or heteroaryl moiety comprising a functional group adapted for covalent binding to a modifier. In certain exemplary embodiments, $L^1$ is a moiety having the structure —$(CR^{L1}R^{L2})_p$-Q-, wherein p is an integer from 0-6, $R^{L1}$ and $R^{L2}$ are independently hydrogen, an aliphatic, alicyclic, heteroaliphatic, heterocyclic, aryl or heteroaryl moiety or $WR^{W1}$ wherein W is O, S, NH, CO, $SO_2$, COO, CONH, and $R^{W1}$ is hydrogen, an aliphatic, alicyclic, heteroaliphatic, heterocyclic, aryl, heteroaryl, alkylaryl or alkylheteroaryl moiety, and Q is a moiety comprising a functional group adapted for covalent binding to a modifier. In certain other exemplary embodiments, $L^1$ is —$CH_2)_p$ wherein p is an integer from 0-5, and Q is a succinimidyl ester moiety having the structure:

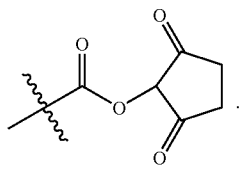

In yet other exemplary embodiments, $L^1$ is —$(CH_2)_{p1}$—CH(OH)$CH_2$NH— wherein $p_1$ is an integer from 1-5, and Q is a maleimidyl moiety having the structure:

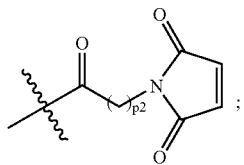

wherein $p_2$ is an integer from 1-5.

In certain exemplary embodiments, in the compounds of the invention, $R^{N1}R^{N2}N$— is a moiety having the structure:

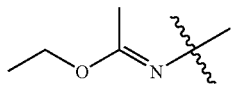

In another aspect, the invention provides compounds having the structure:

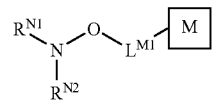

wherein M is a modifier; $L^{M1}$ is a substituted or unsubstituted, cyclic or acyclic, linear or branched $C_{0-12}$alkylidene or $C_{0-12}$alkenylidene moiety wherein up to two non-adjacent methylene units are independently optionally replaced by CO, $CO_2$, COCO, $CONR^{Z1}$, $OCONR^{Z1}$, $NR^{Z1}NR^{Z2}$, $NR^{Z1}NR^{Z2}CO$, $NR^{Z1}CO$, $NR^{Z1}CO_2$, $NR^{Z1}CONR^{Z2}$, SO, $SO_2$, $NR^{Z1}SO_2$, $SO_2NR^{Z1}$, $NR^{Z1}SO_2NR^{Z2}$, O, S, or $NR^{Z1}$; wherein each occurrence of $R^{Z1}$ and $R^{Z2}$ is independently hydrogen, alkyl, heteroalkyl, aryl, heteroaryl or acyl; and $R^{N1}$ and $R^{N2}$ are independently hydrogen, an aliphatic, alicyclic, heteroaliphatic, heterocyclic, aryl or heteroaryl moiety, or a nitrogen protecting group, or $R^{N1}$ and $R^{N2}$, taken together with the nitrogen atom to which they are attached, form a substituted or unsubstituted heterocyclic or heteroaryl moiety.

In certain exemplary embodiments, $L^{M1}$ comprises an NHS ester crosslinker and the compound has the structure:

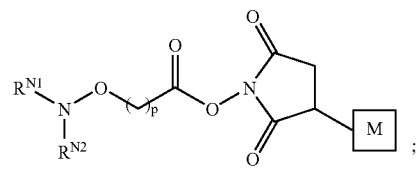

wherein p is 0-5.

In certain other exemplary embodiments, $L^1$ comprises a maleimide crosslinker and the compound has the structure:

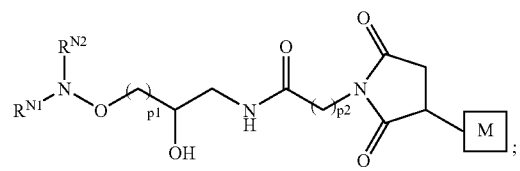

wherein $p_1$ and $p_2$ are independently integers from 1-5.

In certain exemplary embodiments, in the compounds having the structure:

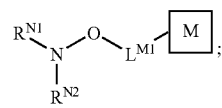

$R^{N1}R^{N2}N$— is a moiety having the structure:

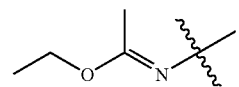

In another aspect, the invention provides a method for preparing a conjugate comprising a carrier substituted with one or more occurrences of a moiety having the structure:

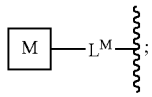

wherein each occurrence of M is independently a modifier; and each occurrence of $L^M$ is independently an oxime-containing linker;

said method comprising steps of:

providing a carrier;

providing one or more modifiers;

providing one or more compounds having the structure: $R^{N1}R^{N2}N$—O-$L^1$; wherein $R^{N1}$ and $R^{N2}$ are independently hydrogen, an aliphatic, alicyclic, heteroaliphatic, heterocyclic, aryl or heteroaryl moiety, or a nitrogen protecting group, or $R^{N1}$ and $R^{N2}$, taken together, form a substituted or unsubstituted alicyclic, aryl or heteroaryl moiety; and each occurrence of $L^1$ is independently an aliphatic, alicyclic, heteroaliphatic, heterocyclic, aryl or heteroaryl moiety comprising a functional group adapted for covalent binding to the modifier; and reacting the one or more compounds of structure $R^{N1}R^{N2}N$—O-$L^1$ with the carrier and the one or more modifiers under suitable conditions so that at least one —O—$NR^{N1}R^{N2}$ moiety is covalently attached to the carrier via an oxime linkage, thereby generating the conjugate.

In another aspect, the invention provides a method for preparing a conjugate comprising a carrier substituted with one or more occurrences of a moiety having the structure:

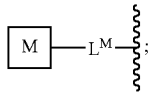

wherein each occurrence of M is independently a modifier; and each occurrence of $L^M$ is independently an oxime-containing linker;

said method comprising steps of:

providing a carrier;

providing one or more compounds having the structure:

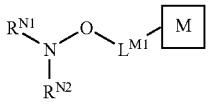

wherein $L^{M1}$ is a substituted or unsubstituted, cyclic or acyclic, linear or branched $C_{0-12}$alkylidene or $C_{0-12}$alkenylidene moiety wherein up to two nonadjacent methylene units are independently optionally replaced by CO, $CO_2$, COCO, $CONR^{Z1}$, $OCONR^{Z1}$, $NR^{Z1}NR^{Z2}$, $NR^{Z1}NR^{Z2}CO$, $NR^{Z1}CO$, $NR^{Z1}CO_2$, $NR^{Z1}CONR^{Z2}$, SO, $SO_2$, $NR^{Z1}SO_2$, $SO_2NR^{Z1}$, $NR^{Z1}SO_2NR^{Z2}$, O, S, or $NR^{Z1}$; wherein each occurrence of $R^{Z1}$ and $R^{Z2}$ is independently hydrogen, alkyl, heteroalkyl, aryl, heteroaryl or acyl; and $R^{N1}$ and $R^{N2}$ are independently hydrogen, an aliphatic, alicyclic, heteroaliphatic, heterocyclic, aryl or heteroaryl moiety, or a nitrogen protecting group, or $R^{N1}$ and $R^{N2}$, taken together with the nitrogen atom to which they are attached, form a substituted or unsubstituted heterocyclic or heteroaryl moiety; and reacting the carrier with the one or more compounds of structure:

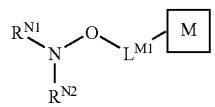

under suitable conditions so that at least one —O—$NR^{N1}R^{N2}$ moiety is covalently attached to the carrier via an oxime linkage, thereby generating the conjugate.

In certain exemplary embodiments, $R^{N1}$ and $R^{N2}$ are each hydrogen. In certain exemplary embodiments, in the one or more compounds of structure $R^{N1}R^{N2}N$—O-$L^1$; at least one of $R^{N1}$ and $R^{N2}$ is a nitrogen protecting group; and the method further comprises the step of hydrolyzing the one or more compounds having the structure $R^{N1}R^{N2}N$—O-$L^1$ to form one or more compounds having the structure $H_2N$—O-$L^1$ prior to reacting with the carrier. In certain exemplary embodiments, in the one or more compounds of structure $R^{N1}R^{N2}N$—O-$L^1$, $R^{N1}R^{N2}N$— has the structure $CH_3CH_2OC(CH_3)$=N—; and the one or more compounds have the following structure:

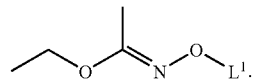

In certain exemplary embodiments, in the one or more compounds of structure

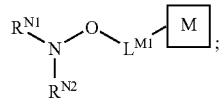

at least one of $R^{N1}$ and $R^{N2}$ is a nitrogen protecting group; and the method further comprises the step of hydrolyzing the one or more compounds having the structure:

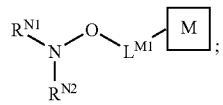

to form one or more compounds having the structure:

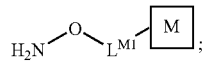

prior to reacting with the carrier.

In certain exemplary embodiments, in the one or more compounds of structure:

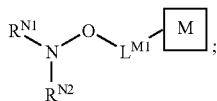

$R^{N1}R^{N2}N-$ has the structure $CH_3CH_2OC(CH_3)=N-$; and the one or more compounds have the following structure:

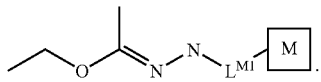

In certain exemplary embodiments, in practicing the method of the invention, the carrier is a biodegradable biocompatible polyacetal wherein at least a subset of the polyacetal repeat structural units have the following chemical structure:

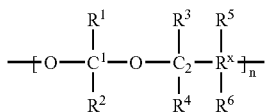

wherein for each occurrence of the n bracketed structure, one of $R^1$ and $R^2$ is hydrogen, and the other is a biocompatible group and includes a carbon atom covalently attached to $C^1$; $R^x$ includes a carbon atom covalently attached to $C^2$; n is an integer; each occurrence of $R^3$, $R^4$, $R^5$ and $R^6$ is a biocompatible group and is independently hydrogen or an organic moiety; and for each occurrence of the bracketed structure n, at least one of $R^1$, $R^2$, $R^3$, $R^4$, $R^5$ and $R^6$ comprises a carbonyl group suitable for oxime formation. In certain embodiments, the carbonyl group is an aldehyde.

In certain exemplary embodiments, in practicing the method of the invention, the carrier is a biodegradable biocompatible polyketal wherein at least a subset of the polyketal repeat structural units have the following chemical structure:

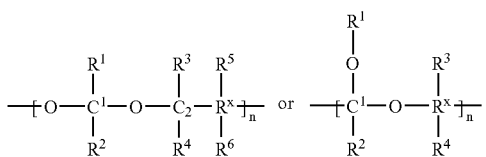

wherein each occurrence of $R^1$ and $R^2$ is a biocompatible group and includes a carbon atom covalently attached to $C^1$; $R^x$ includes a carbon atom covalently attached to $C^2$; n is an integer; each occurrence of $R^3$, $R^4$, $R^5$ and $R^6$ is a biocompatible group and is independently hydrogen or an organic moiety; and for each occurrence of the bracketed structure n, at least one of $R^1$, $R^2$, $R^3$, $R^4$, $R^5$ and $R^6$ comprises a carbonyl group suitable for oxime formation.

In another aspect, the invention provides compositions comprising the conjugate of the invention and a pharmaceutically suitable carrier or diluent. In certain embodiments, the inventive compositions comprise a conjugate associated with an effective amount of a therapeutic agent; wherein the therapeutic agent is incorporated into an released from said conjugate matrix by degradation of the conjugate matrix or diffusion of the agent out of the matrix over a period of time. In certain embodiments, the conjugate is further associated with a diagnostic agent.

In yet another aspect, the invention provides a method of administering to a patient in need of treatment, comprising administering to the subject an effective amount of a suitable therapeutic agent; wherein said therapeutic agent is associated with and released from a conjugate of the invention by degradation of the conjugate matrix or diffusion of the agent out of the matrix over a period of time. In certain embodiments, the therapeutic agent is locally delivered by implantation of said conjugate matrix incorporating the therapeutic agent. In certain embodiments, the therapeutic agent is selected from the group consisting of: vitamins, anti-AIDS substances, anti-cancer substances, antibiotics, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anticoagulants and/or antithrombotic agents, local anesthetics, ophthalmics, prostaglandins, anti-depressants, anti-psychotic substances, anti-emetics, imaging agents.

In certain other exemplary embodiments, the method further comprises administering with the therapeutic agent additional biologically active compounds selected from the group consisting of vitamins, anti-AIDS substances, anti-cancer substances, antibiotics, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anticoagulants and/or antithrombotic agents, local anesthetics, ophthalmics, prostaglandins, anti-depressants, anti-psychotic substances, anti-emetics, imaging agents, and combination thereof.

In certain embodiments, in practicing the method of the invention, the conjugate further comprises or is associated with a diagnostic label. In certain exemplary embodiments, the diagnostic label is selected from the group consisting of: radiopharmaceutical or radioactive isotopes for gamma scintigraphy and PET, contrast agent for Magnetic Resonance Imaging (MRI), contrast agent for computed tomography, contrast agent for X-ray imaging method, agent for ultrasound diagnostic method, agent for neutron activation, moiety which can reflect, scatter or affect X-rays, ultrasounds, radiowaves and microwaves and fluorophores. In certain exemplary embodiments, the conjugate is further monitored in vivo.

In another aspect, the invention provides a method of administering a conjugate of the invention to an animal, comprising preparing an aqueous formulation of said conjugate and parenterally injecting said formulation in the animal. In certain exemplary embodiments, the conjugate comprises a biologically active modifier. In certain exemplary embodiments, the conjugate comprises a detectable modifier.

In another aspect, the invention provides a method of administering a conjugate of the invention to an animal, comprising preparing an implant comprising said conjugate, and implanting said implant into the animal. In certain exemplary embodiments, the implant is a biodegradable gel matrix.

In another aspect, the invention provides a method for treating of an animal in need thereof, comprising administering a conjugate according to the methods described above, wherein said conjugate is associated with a biologically active component.

In another aspect, the invention provides a method for treating of an animal in need thereof, comprising administering a conjugate according to the methods described above, wherein said conjugate comprises a biologically active modifier. In certain exemplary embodiments, the biologically active component is a gene vector.

In another aspect, the invention provides a method for eliciting an immune response in an animal, comprising administering a conjugate as in the methods described above, wherein said conjugate comprises an antigen modifier.

In another aspect, the invention provides a method of diagnosing a disease in an animal, comprising steps of:
  administering a conjugate as in the methods described above, wherein said conjugate comprises a detectable modifier; and
  detecting the detectable modifier.

In certain exemplary embodiments, the step of detecting the detectable modifier is performed non-invasively. In certain exemplary embodiments, the step of detecting the detectable modifier is performed using suitable imaging equipment.

DEFINITIONS

Certain compounds of the present invention, and definitions of specific functional groups are also described in more detail herein. For purposes of this invention, the chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference. Furthermore, it will be appreciated by one of ordinary skill in the art that the synthetic methods, as described herein, utilize a variety of protecting groups. By the term "protecting group", has used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. For example, in certain embodiments, certain exemplary oxygen protecting groups may be utilized. These oxygen protecting groups include, but are not limited to methyl ethers, substituted methyl ethers (e.g., MOM (methoxymethyl ether), MTM (methylthiomethyl ether), BOM (benzyloxymethyl ether), PMBM (p-methoxybenzyloxymethyl ether), to name a few), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether), to name a few), esters (e.g., formate, acetate, benzoate (Bz), trifluoroacetate, dichloroacetate, to name a few), carbonates, cyclic acetals and ketals. In certain other exemplary embodiments, nitrogen protecting groups are utilized. These nitrogen protecting groups include, but are not limited to, carbamates (including methyl, ethyl and substituted ethyl carbamates (e.g., Troc), to name a few) amides, cyclic imide derivatives, N-Alkyl and N-Aryl amines, imine derivatives, and enamine derivatives, to name a few. Certain other exemplary protecting groups are detailed herein, however, it will be appreciated that the present invention is not intended to be limited to these protecting groups; rather, a variety of additional equivalent protecting groups can be readily identified using the above criteria and utilized in the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

"Biocompatible": The term "biocompatible", as used herein is intended to describe compounds that exert minimal destructive or host response effects while in contact with body fluids or living cells or tissues. Thus a biocompatible group, as used herein, refers to an aliphatic, alicyclic, heteroaliphatic, heteroalicyclic, aryl or heteroaryl moiety, which falls within the definition of the term biocompatible, as defined above and herein. The term "Biocompatibility" as used herein, is also taken to mean minimal interactions with recognition proteins, e.g., naturally occurring antibodies, cell proteins, cells and other components of biological systems. However, substances and functional groups specifically intended to cause the above effects, e.g., drugs and prodrugs, are considered to be biocompatible. Preferably, compounds are "biocompatible" if their addition to normal cells in vitro, at concentrations similar to the intended in vivo concentration, results in less than or equal to 5% cell death during the time equivalent to the half-life of the compound in vivo (e.g., the period of time required for 50% of the compound administered in vivo to be eliminated/cleared), and their administration in vivo induces minimal inflammation, foreign body reaction, immunotoxicity, chemical toxicity or other such adverse effects. In the above sentence, the term "normal cells" refers to cells that are not intended to be destroyed by the compound being tested. For example, non-transformed cells should be used for testing biocompatibility of antineoplastic compounds.

"Biodegradable": As used herein, "biodegradable" polymers are polymers that are susceptible to biological processing in vivo. As used herein, "biodegradable" compounds are those that, when taken up by cells, can be broken down by the lysosomal or other chemical machinery or by hydrolysis into components that the cells can either reuse or dispose of without significant toxic effect on the cells. The degradation fragments preferably induce no or little organ or cell overload or pathological processes caused by such overload or other adverse effects in vivo. Examples of biodegradation processes include enzymatic and non-enzymatic hydrolysis, oxidation and reduction. Suitable conditions for non-enzymatic hydrolysis, for example, include exposure of the biodegradable polyal conjugates to water at a temperature and a pH of lysosomal intracellular compartment. Biodegradation of polyal conjugates of the present invention can also be enhanced extracellularly, e.g. in low pH regions of the animal body, e.g. an inflamed area, in the close vicinity of activated macrophages or other cells releasing degradation facilitating factors. In certain preferred embodiments, the effective size of the polymer at pH~7.5 does not detectably change over 1 to 7 days, and remains within 50% of the original polymer size for at least several weeks. At pH~5, on the other hand, the polymer preferably detectably degrades over 1 to 5 days, and is completely transformed into low molecular weight fragments within a two-week to several-month time frame. Polymer integrity in such tests can be measured, for example, by size exclusion HPLC. Although faster degradation may be in some cases preferable, in general it may be more desirable that the polymer degrades in cells with the rate that does not exceed the rate of metabolization or excretion of polymer fragments by the cells. In preferred embodiments, the polymers and polymer biodegradation byproducts are biocompatible.

"Hydrophilic": The term "hydrophilic" as it relates to substituents on the polymer monomeric units does not essentially differ from the common meaning of this term in the art, and denotes organic moieties which contain ionizable, polar, or polarizable atoms, or which otherwise may be solvated by water molecules. Thus a hydrophilic group, as used herein, refers to an aliphatic, alicyclic, heteroaliphatic, heteroalicyclic, aryl or heteroaryl moiety, which falls within the definition of the term hydrophilic, as defined above. Examples of particular hydrophilic organic moieties which are suitable include, without limitation, aliphatic or heteroaliphatic groups comprising a chain of atoms in a range of between about one and twelve atoms, hydroxyl, hydroxyalkyl, amine, carboxyl, amide, carboxylic ester, thioester, aldehyde, nitryl, isonitryl, nitroso, hydroxylamine, mercaptoalkyl, heterocycle, carbamates, carboxylic acids and their salts, sulfonic acids and their salts, sulfonic acid esters, phosphoric acids and their salts, phosphate esters, polyglycol ethers, polyamines, polycarboxylates, polyesters and polythioesters. In preferred embodiments of the present invention, at least one of the polymer monomeric units include a carboxyl group (COOH), an aldehyde group (CHO), a methylol ($CH_2OH$) or a glycol (for example, $CHOH\text{—}CH_2OH$ or $CH\text{—}(CH_2OH)_2$).

"Hydrophilic": The term "hydrophilic" as it relates to the polymers of the invention generally does not differ from usage of this term in the art, and denotes polymers comprising hydrophilic functional groups as defined above. In a preferred embodiment, hydrophilic polymer is a water-soluble polymer. Hydrophilicity of the polymer can be directly measured through determination of hydration energy, or determined through investigation between two liquid phases, or by chromatography on solid phases with known hydrophobicity, such as, for example, C4 or C18.

"Biomolecules": The term "biomolecules", as used herein, refers to molecules (e.g., proteins, amino acids, peptides, polynucleotides, nucleotides, carbohydrates, sugars, lipids, nucleoproteins, glycoproteins, lipoproteins, steroids, etc.) which belong to classes of chemical compounds, whether naturally-occurring or artificially created (e.g., by synthetic or recombinant methods), that are commonly found in cells and tissues. Specific classes of biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, and RNA.

"Physiological conditions": The phrase "physiological conditions", as used herein, relates to the range of chemical (e.g., pH, ionic strength) and biochemical (e.g., enzyme concentrations) conditions likely to be encountered in the extracellular fluids of living tissues. For most normal tissues, the physiological pH ranges from about 7.0 to 7.4. Circulating blood plasma and normal interstitial liquid represent typical examples of normal physiological conditions.

"Polysaccharide", "carbohydrate" or "oligosaccharide": The terms "polysaccharide", "carbohydrate", or "oligosaccharide" are known in the art and refer, generally, to substances having chemical formula $(CH_2O)_n$, where generally n>2, and their derivatives. Carbohydrates are polyhydroxyaldehydes or polyhydroxyketones, or change to such substances on simple chemical transformations, such as hydrolysis, oxydation or reduction. Typically, carbohydrates are present in the form of cyclic acetals or ketals (such as, glucose or fructose). Said cyclic units (monosaccharides) may be connected to each other to form molecules with few (oligosaccharides) or several (polysaccharides) monosaccharide units. Often, carbohydrates with well defined number, types and positioning of monosaccharide units are called oligosaccharides, whereas carbohydrates consisting of mixtures of molecules of variable numbers and/or positioning of monosaccharide units are called polysaccharides. The terms "polysaccharide", "carbohydrate", and "oligosaccharide", are used herein interchangeably. A polysaccharide may include natural sugars (e.g., glucose, fructose, galactose, mannose, arabinose, ribose, and xylose) and/or modified sugars (e.g., 2'-fluororibose, 2'-deoxyribose, and hexose).

"Small molecule": As used herein, the term "small molecule" refers to molecules, whether naturally-occurring or artificially created (e.g., via chemical synthesis) that have a relatively low molecular weight. Preferred small molecules are biologically active in that they produce a local or systemic effect in animals, preferably mammals, more preferably humans. Typically, small molecules have a molecular weight of less than about 1500 g/mol. In certain preferred embodiments, the small molecule is a drug. Preferably, though not necessarily, the drug is one that has already been deemed safe and effective for use by the appropriate governmental agency or body. For example, drugs for human use listed by the FDA under 21 C.F.R. §§330.5, 331 through 361, and 440 through 460; drugs for veterinary use listed by the FDA under 21 C.F.R. §§500 through 589, incorporated herein by reference, are all considered suitable for use with the present hydrophilic polymers.

Classes of small molecule drugs that can be used in the practice of the present invention include, but are not limited to, vitamins, anti-AIDS substances, anti-cancer substances, antibiotics, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anticoagulants and/or antithrombotic agents, local anesthetics, ophthalmics, prostaglandins, anti-depressants, anti-psychotic substances, anti-emetics, imaging agents. Many large molecules are also drugs.

A more complete, although not exhaustive, listing of classes and specific drugs suitable for use in the present invention may be found in "Pharmaceutical Substances: Syntheses, Patents, Applications" by Axel Kleemann and Jurgen Engel, Thieme Medical Publishing, 1999 and the "Merck Index: An Encyclopedia of Chemicals, Drugs, and Biologicals", Edited by Susan Budavari et al., CRC Press, 1996, both of which are incorporated herein by reference.

"Pharmaceutically useful group or entity": As used herein, the term Pharmaceutically useful group or entity refers to a compound or fragment thereof, or an organic moiety which, when associated with the polyal conjugates of the present invention, can exert some biological or diagnostic function or activity when administered to a subject, or enhance the therapeutic, diagnostic or preventive properties of the polyal conjugates in biomedical applications, or improve safety, alter biodegradation or excretion, or is detectable. Examples of suitable pharmaceutically useful groups or entities include hydrophilicity/hydrophobicity modifiers, pharmacokinetic modifiers, biologically active modifiers, detectable modifiers.

"Modifier": As used herein, the term modifier refers to an organic, inorganic or bioorganic moiety that is covalently incorporated into a carrier. Modifiers can be small molecules or macromolecules, and can belong to any chemical or pharmaceutical class, e.g., nucleotides, chemotherapeutic agents, antibacterial agents, antiviral agents, immunomodulators, hormones or analogs thereof, enzymes, inhibitors, alkaloids and therapeutic radionuclides. In certain embodiments, chemotherapeutic agents include, but are not limited to, topoisomerase I and II inhibitors, alkylating agents, anthracyclines, doxorubicin, cisplastin, carboplatin, vincristine, mitromycine, taxol, camptothecin, antisense oligonucleotides, ribozymes, and dactinomycines. In certain embodiments, modifiers according to the invention include, but are not limited to, biomolecules, small molecules, therapeutic agents, pharmaceutically useful groups or entities, macromolecules, diagnostic labels, chelating agents, hydrophilic moieties, dispersants, charge modifying agents, viscosity modifying agents, surfactants, coagulation agents and flocculants, to name a few. A modifier can have one or more pharmaceutical functions, e.g., biological activity and pharmacokinetics modification. Pharmacokinetics modifiers can include, for example, antibodies, antigens, receptor ligands, hydrophilic, hydrophobic or charged groups. Biologically active modifiers include, for example, therapeutic drugs and prodrugs, antigens, immunomodulators. Detectable modifiers include diagnostic labels, such as radioactive, fluorescent, paramagnetic, superparamagnetic, ferromagnetic, X-ray modulating, X-ray-opaque, ultrosound-reflective, and other substances detectable by one of available clinical or laboratory methods, e.g., scintigraphy, NMR spectroscopy, MRI, X-ray tomography, sonotomography, photoimaging, radioimmunoassay. Viral and non-viral gene vectors are considered to be modifiers.

"Macromolecule": As used herein, the term macromolecule refers to molecules, whether naturally-occurring or artificially created (e.g., via chemical synthesis) that have a relatively high molecular weight, generally above 1500 g/mole Preferred macromolecules are biologically active in that they exert a biological function in animals, preferably mammals, more preferably humans. Examples of macromolecules include proteins, enzymes, growth factors, cytokines, peptides, polypeptides, polylysine, proteins, lipids, polyelectrolytes, immunoglobulins, DNA, RNA, ribozymes, plasmids, and lectins. For the purpose of this invention, supramolecular constructs such as viruses and protein associates (e.g., dimers) are considered to be macromolecules. When associated with the polyal conjugates of the invention, a macromolecule may be chemically modified prior to being associated with said biodegradable biocompatible polyal conjugate.

"Diagnostic label": As used herein, the term diagnostic label refers to an atom, group of atoms, moiety or functional group, a nanocrystal, or other discrete element of a composition of matter, that can be detected in vivo or ex vivo using analytical methods known in the art. When associated with a biodegradable biocompatible polyal conjugate of the present invention, such diagnostic labels permit the monitoring of the biodegradable biocompatible polyal conjugate in vivo. On the other hand, constructs and compositions that include diagnostic labels can be used to monitor biological functions or structures. Examples of diagnostic labels include, without limitations, labels that can be used in medical diagnostic procedures, such as, radiopharmaceutical or radioactive isotopes for gamma scintigraphy and Positron Emission Tomography (PET), contrast agent for Magnetic Resonance Imaging (MRI) (for example paramagnetic atoms and superparamagnetic nanocrystals), contrast agent for computed tomography, contrast agent for X-ray imaging method, agent for ultrasound diagnostic method, agent for neutron activation, and moiety which can reflect, scatter or affect X-rays, ultrasounds, radiowaves and microwaves, fluorophores in various optical procedures, etc.

"Effective amount of a glycol-specific oxidizing agent": as it relates to the oxidative cleavage of the polysaccharides referred to in the present invention, the phrase effective amount of a glycol-specific oxidizing agent means an amount of the glycol-specific oxidizing agent that provides oxidative opening of essentially all carbohydrate rings of a polysaccharide.

"Protected hydrophilic group" and "Protected organic moiety" as these terms are used herein, mean a chemical group which will not interfere with a chemical reaction that the carrier or carrier conjugate is subjected to. Examples of protected hydrophilic groups include carboxylic esters, alkoxy groups, thioesters, thioethers, vinyl groups, haloalkyl groups, Fmoc-alcohols, etc.

"Aliphatic": In general, the term aliphatic, as used herein, includes both saturated and unsaturated, straight chain (i.e., unbranched) or branched aliphatic hydrocarbons, which are optionally substituted with one or more functional groups, as defined below. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (substituted, unsubstituted, branched or unbranched) having 1-6 carbon atoms. In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms.

Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents, as previously defined. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

"Alicyclic": The term alicyclic, as used herein, refers to compounds which combine the properties of aliphatic and cyclic compounds and include but are not limited to cyclic, or polycyclic aliphatic hydrocarbons and bridged cycloalkyl compounds, which are optionally substituted with one or more functional groups, as defined below. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —$CH_2$-cyclopropyl, cyclobutyl, —$CH_2$-cyclobutyl, cyclopentyl, —$CH_2$-cyclopentyl-n, cyclohexyl, —$CH_2$-cyclohexyl, cyclohexenylethyl, cyclohexanylethyl, norborbyl moieties and the like, which again, may bear one or more substituents.

"Heteroaliphatic": The term "heteroaliphatic", as used herein, refers to aliphatic moieties in which one or more carbon atoms in the main chain have been substituted with an heteroatom. Thus, a heteroaliphatic group refers to an aliphatic chain which contains one or more oxygen sulfur, nitrogen, phosphorus or silicon atoms, e.g., in place of carbon atoms. Heteroaliphatic moieties may be saturated or unsaturated, branched or linear (i.e., unbranched), and substituted or unsubstituted. Substituents include, but are not limited to, any of the substitutents mentioned below, i.e., the substituents recited below resulting in the formation of a stable compound.

"Heteroalicyclic": The term heteroalicyclic, as used herein, refers to compounds which combine the properties of heteroaliphatic and cyclic compounds and include but are not limited to saturated and unsaturated mono- or polycyclic heterocycles such as morpholino, pyrrolidinyl, furanyl, thiofuranyl, pyrrolyl etc., which are optionally substituted with one or more functional groups. Substituents include, but are not limited to, any of the substitutents mentioned below, i.e., the substituents recited below resulting in the formation of a stable compound.

"Alkyl": the term alkyl as used herein refers to saturated, straight- or branched-chain hydrocarbon radicals derived from a hydrocarbon moiety containing between one and twenty carbon atoms by removal of a single hydrogen atom, which alkyl groups are optionally substituted with one or more functional groups. Substituents include, but are not limited to, any of the substitutents mentioned below, i.e., the substituents recited below resulting in the formation of a stable compound. Examples of alkyl radicals include, but are not limited to, methyl, ethyl, propyl, isopropyl, n-butyl, tert-butyl, n-pentyl, neopentyl, n-hexyl, n-heptyl, n-octyl, n-decyl, n-undecyl, and dodecyl.

"Alkoxy": the term alkoxy as used herein refers to an alkyl groups, as previously defined, attached to the parent molecular moiety through an oxygen atom. Examples include, but are not limited to, methoxy, ethoxy, propoxy, isopropoxy, n-butoxy, tert-butoxy, neopentoxy, and n-hexoxy.

"Alkenyl": the term alkenyl denotes a monovalent group derived from a hydrocarbon moiety having at least one carbon-carbon double bond by the removal of a single hydrogen atom, which alkenyl groups are optionally substituted with one or more functional groups. Substituents include, but are not limited to, any of the substitutents mentioned below, i.e., the substituents recited below resulting in the formation of a stable compound. Alkenyl groups include, for example, ethenyl, propenyl, butenyl, 1-methyl-2-buten-1-yl, and the like.

"Alkynyl": the term alkynyl as used herein refers to a monovalent group derived form a hydrocarbon having at least one carbon-carbon triple bond by the removal of a single hydrogen atom, which alkenyl groups are optionally substituted. Substituents include, but are not limited to, any of the substitutents mentioned below, i.e., the substituents recited below resulting in the formation of a stable compound. Representative alkynyl groups include ethynyl, 2-propynyl (propargyl), 1-propynyl, and the like.

"Amine": the term amine as used herein refers to one, two, or three, respectively, alkyl groups, as previously defined, attached to the parent molecular moiety through a nitrogen atom. The term alkylamino refers to a group having the structure —NHR' wherein R' is an alkyl group, as previously defined; and the term dialkylamino refers to a group having the structure —NR'R", wherein R' and R" are each independently selected from the group consisting of alkyl groups. The term trialkylamino refers to a group having the structure —NR'R"R'", wherein R', R", and R'" are each independently selected from the group consisting of alkyl groups. Additionally, R', R", and/or R'" taken together may optionally be —$(CH_2)_k$— where k is an integer from 2 to 6. Example include, but are not limited to, methylamino, dimethylamino, ethylamino, diethylamino, diethylaminocarbonyl, methylethylamino, iso-propylamino, piperidino, trimethylamino, and propylamino.

"Aryl": The term aryl, as used herein, refers to stable mono- or polycyclic, unsaturated moieties having preferably 3-14 carbon atoms, each of which may be substituted or unsubstituted. Substituents include, but are not limited to, any of the substitutents mentioned below, i.e., the substituents recited below resulting in the formation of a stable compound. The term aryl may refer to a mono- or bicyclic carbocyclic ring system having one or two aromatic rings including, but not limited to, phenyl, naphthyl, tetrahydronaphthyl, indanyl, indenyl and the like.

"Heteroaryl": The term heteroaryl, as used herein, refers to a stable heterocyclic or polyheterocyclic, unsaturated radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms. Heteroaryl moieties may be substituted or unsubstituted. Substituents include, but are not limited to, any of the substitutents mentioned below, i.e., the substituents recited below resulting in the formation of a stable compound. Examples of heteroaryl nuclei include pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will also be appreciated that aryl and heteroaryl moieties, as defined herein may be attached via an aliphatic, alicyclic, heteroaliphatic, heteroalicyclic, alkyl or heteroalkyl moiety and thus also include -aliphatic)aryl, -(heteroaliphatic)aryl, -(aliphatic)heteroaryl, -(heteroaliphatic)heteroaryl, -(alkyl)

aryl, -(heteroalkyl)aryl, -heteroalkyl)aryl, and -(heteroalkyl)heteroaryl moieties. Thus, as used herein, the phrases "aryl or heteroaryl" and "aryl, heteroaryl, -(aliphatic)aryl, -(heteroaliphatic)aryl, -(aliphatic)heteroaryl, (heteroaliphatic) heteroaryl, -alkyl)aryl, -(heteroalkyl)aryl, -(heteroalkyl)aryl, and -(heteroalkyl)heteroaryl" are interchangeable.

"Carboxylic acid": The term carboxylic acid as used herein refers to a group of formula —$CO_2H$.

"Halo, halide and halogen": The terms halo, halide and halogen as used herein refer to an atom selected from fluorine, chlorine, bromine, and iodine.

"Methylol": The term methylol as used herein refers to an alcohol group of the structure $CH_2OH$.

"Hydroxyalkyl": As used herein, the term hydroxyalkyl refers to an alkyl group, as defined above, bearing at least one OH group.

"Mercaptoalkyl": The term mercaptoalkyl as used therein refers to an alkyl group, as defined above, bearing at least one SH group "Heterocyclic": The term heterocyclic, as used herein, refers to a non-aromatic partially unsaturated or fully saturated 3- to 10-membered ring system, which includes single rings of 3 to 8 atoms in size and bi- and tri-cyclic ring systems which may include aromatic six-membered aryl or aromatic heterocyclic groups fused to a non-aromatic ring. Heterocyclic moieties may be substituted or unsubstituted. Substituents include, but are not limited to, any of the substituents mentioned below, i.e., the substituents recited below resulting in the formation of a stable compound. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized.

"Acyl": The term acyl, as used herein, refers to a group comprising a carbonyl group of the formula C=O. Examples of acyl groups include aldehydes, ketones, carboxylic acids, acyl halides, anhydrides, thioesters, amides and carboxylic esters.

"Hydrocarbon": The term hydrocarbon, as used herein, refers to any chemical group comprising hydrogen and carbon. The hydrocarbon may be substituted or unsubstitued. The hydrocarbon may be unsaturated, saturated, branched, unbranched, cyclic, polycyclic, or heterocyclic. Illustrative hydrocarbons include, for example, methyl, ethyl, n-propyl, iso-propyl, cyclopropyl, allyl, vinyl, n-butyl, tert-butyl, ethynyl, cyclohexyl, methoxy, diethylamino, and the like. As would be known to one skilled in this art, all valencies must be satisfied in making any substitutions.

"Substituted": The terms substituted, whether preceded by the term "optionally" or not, and substituent, as used herein, refers to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Heteroatoms such as nitrogen may have hydrogen substituents and/or any permissible substituents of organic compounds described herein which satisfy the valencies of the heteroatoms. Examples of substituents include, but are not limited to aliphatic; alicyclic; heteroaliphatic; heteroalicyclic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R)_2$; —$N(R_x)_2$; —$S(O)_2R_x$; —$NR_x(CO)R_x$ wherein each occurrence of $R_x$ independently includes, but is not limited to, aliphatic, alicyclic, heteroaliphatic, heteroalicyclic, aryl, heteroaryl, alkylaryl, or alkylheteroaryl, wherein any of the aliphatic, alicyclic, heteroaliphatic, heteroalicyclic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted.

The following are more general terms used throughout the present application:

"Animal": The term animal, as used herein, refers to humans as well as non-human animals, at any stage of development, including, for example, mammals, birds, reptiles, amphibians, fish, worms and single cells. Cell cultures and live tissue samples are considered to be pluralities of animals. Preferably, the non-human animal is a mammal (e.g., a rodent, a mouse, a rat, a rabbit, a monkey, a dog, a cat, a primate, or a pig). An animal may be a transgenic animal or a human clone.

"Associated with": When two entities are "associated with" one another as described herein, they are linked by a direct or indirect covalent or non-covalent interaction. Preferably, the association is covalent. Desirable non-covalent interactions include hydrogen bonding, van der Waals interactions, hydrophobic interactions, magnetic interactions, electrostatic interactions, or combinations thereof, etc.

"Effective amount": In general, as it refers to an active agent or drug delivery device, the term "effective amount" refers to the amount necessary to elicit the desired biological response. As will be appreciated by those of ordinary skill in this art, the effective amount of an agent or device may vary depending on such factors as the desired biological endpoint, the agent to be delivered, the composition of the encapsulating matrix, the target tissue, etc. For example, the effective amount of microparticles containing an antigen to be delivered to immunize an individual is the amount that results in an immune response sufficient to prevent infection with an organism having the administered antigen.

"PHF" refers to poly(1-hydroxymethylethylene hydroxymethyl-formal).

DETAILED DESCRIPTION OF CERTAIN PREFERRED EMBODIMENTS OF THE INVENTION

Figure 1:
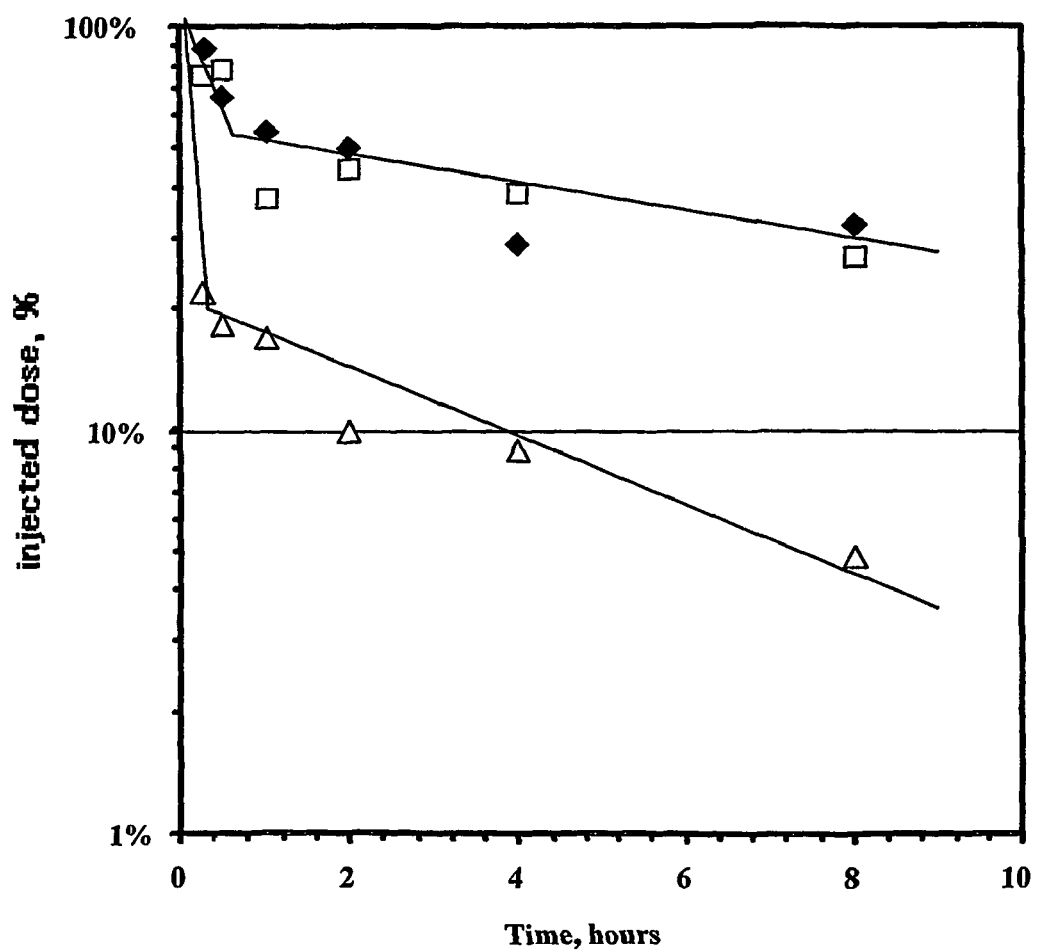
FIG. 1 depicts the blood activity following iv injection of $^{111}$In-labeled trypsin conjugates. (Δ) DTPA-modified trypsin; (□) PHF-SA-Trypsin; and (♦) PHF-AO-Trypsin conjugates.

Certain preferred embodiments of the invention will now be more particularly described and pointed out in the claims. It will be understood that the particular embodiments of the invention are shown by way of illustration and not as limitations of the invention. Principle features of the invention may be employed in various embodiments without departing from the scope of the invention.

In one aspect, the present invention provides conjugates of small and large (bio)molecules and/or other (in)organic moieties (i.e., modifiers) with carriers, wherein the small/larger (bio)molecules and/or other (in)organic moieties are covalently attached to the carrier via oxime-containing linkages. In certain embodiments, the carrier is a macromolecule, a molecular matrix or an interface. In certain other embodiments, the carrier is a fully synthetic, semi-synthetic or naturally-occurring polymer. In certain exemplary embodiments; the conjugates of the invention find use in biomedical applications, such as gene and drug delivery and tissue engineering, and the carrier is biocompatible and biodegradable. In certain other embodiments, the carrier is hydrophilic. In certain exemplary embodiments, the polymer carriers used in the present invention comprise at least one hydrolizable bond in each monomer unit positioned within the main chain. This ensures that the degradation process (via hydrolysis/cleavage of the monomer units) will result in fragmentation of the polymer conjugate to the monomeric components (i.e., degradation), and confers to the polymer conjugates of the invention their biodegradable properties. The properties (e.g., solubility, bioadhesivity and hydrophilicity) of biodegradable biocompatible polymer conjugates can be modified by subsequent substitution of additional hydrophilic or hydrophobic groups.

Non-bioadhesive, fully biodegradable soluble polymer conjugates would be instrumental in such biomedical applications. However, rational development of such materials is hindered by the complexity of macromolecule interactions with the biological milieu. Addressing the need for polymer conjugates having these above characteristics, the present invention provides novel biodegradable biocompatible polyal conjugates, which are chemically modified by covalent attachment of small/large (bio)molecules or other (in)organic moieties (i.e., modifiers) via oxime-containing linkages.

Biodegradable Biocompatible Polyal Conjugates

As discussed above, novel concepts in pharmacology and bioengineering impose new, more specific and more stringent requirements on biomedical polymers. Ideally, advanced macromolecular materials would combine negligible reactivity in vivo with low toxicity and biodegradability. Polymer structure should support an ample set of technologies for polymer derivatization, for example, conjugation with drugs, cell-specific ligands, or other desirable modifiers. Materials combining all the above features would be useful in the development of macromolecular drugs, drug delivery systems, implants and templates for tissue engineering.

On the chemistry level, developing such biocompatible and biodegradable materials translates into developing macromolecules with minimized interactions in vivo, main chains susceptible to hydrolysis (e.g., degradation) in vivo, and readily modifiable functional groups. Another consideration to take into account is that both the main chain and the functional groups interact with an extremely complex biological milieu, and all interactions may be amplified via cooperative mechanisms.

Biomolecule interactions in vivo are mediated by several components of cell surfaces, extracellular matrix, and biological fluids. For example, both biomolecule internalization by cells and cell adhesion to polymer-coated surfaces can be mediated by several cell surface elements, many of which are functionally specialized. Cooperative binding, often referred to as "non-specific interactions", is another major factor of biomolecule (and surface) reactivity in vivo. Cell interactions with polymers and recognition protein-polymer complexes also have an element of cooperativity. The very nature of cooperative interactions in complex systems suggests that any large molecule can significantly interact with a complex substrate for the simple reason that, because the binding energy is additive, the association constant of cooperative binding ($K_a$) would grow with the number of associations exponentially. In other words, any polymer of a sufficient length can be expected to interact with at least one of the various components of a biological system. Even if a molecule of certain size shows low interactions in cell cultures and in vivo, a larger molecule of the same type (or a supra molecular assembly) can have a much higher binding activity.

In summary, even if polymer molecules are assembled of domains that do not interact with cell receptors and recognition proteins, such molecules can be capable of cooperative interactions in vivo; i.e., completely inert polymers may not exist at all. However, several biomolecules and biological interfaces do appear to be functionally inert, except for their specialized signaling domains. For example, plasma proteins are known to circulate for several weeks without uptake in the reticuloendothelial system (RES), unlike artificial constructs of comparable size that have never been reported to have comparable blood half-lives. Without wishing to be bound to any particular theory, we propose that the mutual "inertness" of natural biomolecules and surfaces may relate to their relatively uniform interface structures, where the potential binding sites are always saturated by naturally occurring counter-agents present in abundance. Therefore, emulation of the common interface structures can result in a material that would not actively interact with actually existing binding sites because these sites would be pre-occupied by the natural "prototypes".

Poly- and oligosaccharides are the most abundant interface molecules expressed (as varous glycoconjugates) on cell surfaces, plasma proteins, and proteins of the extracellular matrix. Therefore, the invention encompasses structural emulation of interface carbohydrates in an effort to identify and exclude all structural components that can be recognized, even with low affinity, by any biomolecule, especially by cell receptors and recognition proteins.

All interface carbohydrates have common structural domains which appear to be irrelevant to their biological function. The acetal/ketal group and the adjacent atoms are present in all carbohydrates regardless of biological activity, whereas the receptor specificity of each molecule depends on the structure and configuration of the glycol domains of the carbohydrate rings. Thus it would seem that biologically inert ("stealth") polymers could be obtained using substructures that form the acetal/ketal structures of the carbohydrate rings; i.e., the O—C—O— group and adjacent carbons. Although functional groups that are common in naturally occurring glycoconjugates (e.g., OH groups) can be used as substitutents, the potentially biorecognizable combinations of these groups, such as rigid structures at C1-C2-C3-C4 (in pyranoses) is not desirable.

The present invention is founded on the recognition that the macromolecular products of the cleavage of at least one of the carbon-carbon bonds in the C1-C2-C3-C4 portion in substantially all the carbohydrate rings of a polysaccharide would have the desired properties (e.g., an essentially inert biocompatible hydrophilic polymer). In addition, synthetic strategies designed to position the polysaccharide acetal/ketal groups within the main chain of the resulting macromolecular product would ensure degradability via proton-catalyzed hydrolysis.

Biocompatible biodegradable polyacetals and polyketals according to this concept have been described in U.S. Pat. Nos. 5,811,510; 5,863,990 and 5,958,398; U.S. Provisional Patent Application 60/348,333; European Patent No.:

0820473; and International Patent Application PCT/US03/01017, each of the above listed patent documents is incorporated herein by reference in its entirety.

The present invention encompasses biodegradable biocompatible hydrophilic polyal conjugates, as well as methods of preparation and methods of use thereof. In certain embodiments, it is anticipated that the present invention will be particularly useful in combination with the above-referenced patent documents, as well as U.S. Pat. No. 5,582,172; U.S. Patent Application No.: 60/147,919 and Ser. No. 09/634,320, each of the above listed patent documents is incorporated herein by reference in its entirety.

As described in Examples 3 and 4, we have successfully made biodegradable biocompatible polyal conjugates which are hydrophilic, hydrolyzable and comprise modifiers (e.g., pharmaceutically useful groups) covalently attached to the polymer carrier via oxime-containing linkages. In certain exemplary embodiments, the polyal conjugates of the present invention have at least one acetal/ketal oxygen atom in each monomer unit positioned within the main chain. This ensures that the degradation process (via hydrolysis/cleavage of the polymer acetal/ketal groups) will result in fragmentation of the polyal conjugate to the monomeric components (i.e., degradation), and confers to the polyal conjugates of the invention their biodegradable properties. The properties (e.g., solubility, bioadhesivity and hydrophilicity) of biodegradable biocompatible polyal conjugates can be adjusted by incorporation of suitable hydrophilic or hydrophobic modifiers or by subsequent substitution of additional hydrophilic or hydrophobic groups. The novelty of the present invention relates in part to the structure and properties of polyal conjugates comprising one or more modifiers covalently attached via oxime-containing linkages to a hydrophilic polykal carrier having acetal/ketal groups in the main chain.

Thus, in certain embodiments, the invention provides a conjugate comprising a carrier substituted with one or more occurrences of a moiety having the structure:

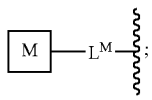

wherein each occurrence of M is independently a modifier; and
each occurrence of $L^M$ is independently an oxime-containing linker.

In certain embodiments, each occurrence of $L^M$ is independently a moiety having the structure:

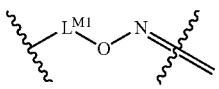

wherein each occurrence of $L^{M1}$ is independently a substituted or unsubstituted, cyclic or acyclic, linear or branched $C_{0-12}$alkylidene or $C_{0-12}$alkenylidene moiety wherein up to two non-adjacent methylene units are independently optionally replaced by CO, $CO_2$, COCO, $CONR^{Z1}$, $OCONR^{Z1}$, $NR^{Z1}NR^{Z2}$, $NR^{Z1}NR^{Z2}CO$, $NR^{Z1}CO$, $NR^{Z1}CO_2$, $NR^{Z1}CONR^{Z2}$, SO, $SO_2$, $NR^{Z1}SO_2$, $SO_2NR^{Z1}$, $NR^{Z1}SO_2NR^{Z2}$, O, S, or $NR^{Z1}$; wherein each occurrence of $R^{Z1}$ and $R^{Z2}$ is independently hydrogen, alkyl, heteroalkyl, aryl, heteroaryl or acyl.

In certain exemplary embodiments, one or more occurrences of $L^M$ independently comprise a crosslinker adapted to facilitate attachment of the modifier M and/or the carrier onto $L^M$. In certain embodiments, $L^M$ comprises a functional group feasible for selective conjugation with a chemical moiety present either in the carrier or in the modifier. For example, $L^M$ may comprise an active ester (e.g., N-hydroxysuccinimide, tetrafluorophenyl, or nitrophenyl ester) useful for conjugation with aminogroups. As another example, $L^M$ may comprise a maleimido group feasible for conjugation with thiols.

Crosslinkers suited for practicing this embodiment of invention are widely known in the art (see, for example, 1994 Pierce Technical Handbook: cross-linking (Appendix A), also available at www.piercenet.com/resources/browse.cfm?fldID=184), including bromoacetic NHS ester, 6-(iodoacetamido)caproic acid NHS ester, maleimidoacetic acid NHS ester, maleimidobenzoic acid NHS ester, etc.

In certain other embodiments, one or more occurrences of $L^{M1}$ independently comprises a maleimide- or N-hydroxysuccinimide ester-containing crosslinker. In yet other embodiments, one or more occurrences of $L^{M1}$ independently comprises a N-maleimidoalkyl carboxylate (1), 4-(N-maleimidomethyl)cyclohexane-1-carboxylate (2), m-maleimidobenzoyl (3), or a 4-(p-maleimidophenyl)butyrate (4) crosslinker.

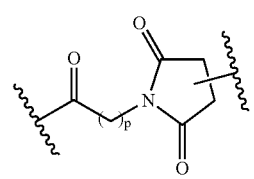

(1)

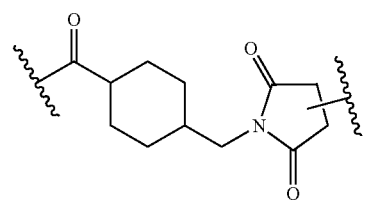

(2)

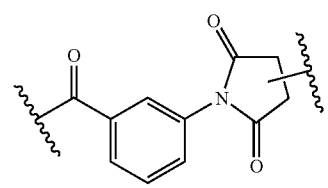

(3)

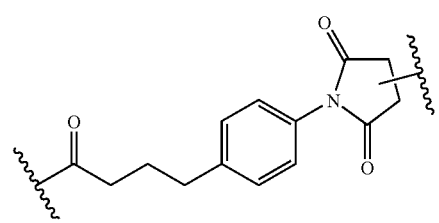

(4)

In still other embodiments, one or more occurrences of $L^{M1}$ independently comprises a carboxysuccinimide crosslinker (5).

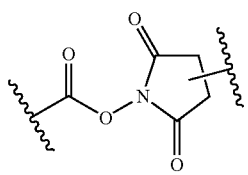

(5)

Carriers

In certain embodiments, biodegradable biocompatible polymer carriers, used for preparation of polymer conjugates of the invention, are naturally occurring polysaccharides, glycopolysaccharides, and synthetic polymers of polyglycoside, polyacetal, polyamide, polyether, and polyester origin and products of their oxidation, fictionalization, modification, cross-linking, and conjugation.

In certain other embodiments, the carrier is a hydrophilic biodegradable polymer selected from the group consisting of carbohydrates, glycopolysaccharides, glycolipids, glycoconjugates, polyacetals, polyketals, and derivatives thereof.

In certain exemplary embodiments, the carrier is a naturally occurring linear and branched biodegradable biocompatible homopolysaccharide selected from the group consisting of cellulose, amylose, dextran, levan, fucoidan, carraginan, inulin, pectin, amylopectin, glycogen and lixenan.

In certain other exemplary embodiments, the carrier is a naturally occurring linear and branched biodegradable biocompatible heteropolysaccharide selected from the group consisting of agarose, hyluronan, chondroitinsulfate, dermatansulfate, keratansulfate, alginic acid and heparin.

In yet other exemplary embodiments, the carrier is a hydrophilic polymer selected from the group consisting of polyacrylates, polyvinyl polymers, polyesters, polyorthoesters, polyamides, polypeptides, and derivatives thereof.

In certain embodiments, the carrier comprises polysaccharides activated by selective oxidation of cyclic vicinal diols of 1,2-, 1,4-, 1,6-, and 2,6-pyranosides, and 1,2-, 1,5-, 1,6-furanosides, or by oxidation of lateral 6-hydroxy and 5,6-diol containing polysaccharides prior to conjugation with one or more modifiers.

In one embodiment, the carriers of the invention comprise activated hydrophilic biodegradable biocompatible polymer carriers comprising from 0.1% to 100% of polyacetal moieties represented by the following chemical structure:

wherein $R_1$ and $R_2$ are independently hydrogen, hydroxyl, carbonyl, carbonyl-containing substituent, a biocompatible organic moiety comprising one or more heteroatoms or a protected hydrophilic functional group; and n is an integer from 1-5000.

In certain exemplary embodiments, the carriers of the present invention are polyals, and comprise acetal/ketal groups within the main chain. Although it is not necessary that the entire acetal/ketal group be positioned within the polymer backbone, it is desirable that at least one of the acetal/ketal oxygen atoms belongs to the main chain.

Accordingly, in still other exemplary embodiments, the carrier comprises a biodegradable biocompatible polyacetal wherein at least a subset of the polyacetal repeat structural units have the following chemical structure:

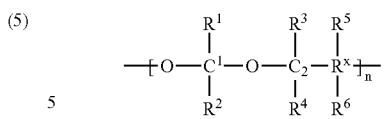

wherein for each occurrence of the n bracketed structure, one of $R^1$ and $R^2$ is hydrogen, and the other is a biocompatible group and includes a carbon atom covalently attached to $C^1$; $R^x$ includes a carbon atom covalently attached to $C^2$; n is an integer; each occurrence of $R^3$, $R^4$, $R^5$ and $R^6$ is a biocompatible group and is independently hydrogen or an organic moiety; and for each occurrence of the bracketed structure n, at least one of $R^1$, $R^2$, $R^3$, $R^4$, $R^5$ and $R^6$ comprises a carbonyl group suitable for oxime formation.

In further exemplary embodiments, the carrier comprises a biodegradable biocompatible polyketal wherein at least a subset of the polyketal repeat structural units have the following chemical structure:

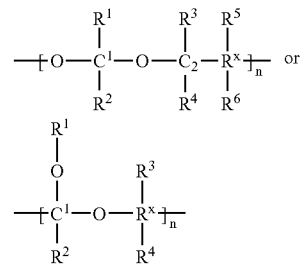

wherein each occurrence of $R^1$ and $R^2$ is a biocompatible group and includes a carbon atom covalently attached to $C^1$; $R^x$ includes a carbon atom covalently attached to $C^2$; n is an integer; each occurrence of $R^3$, $R^4$, $R^5$ and $R^6$ is a biocompatible group and is independently hydrogen or an organic moiety; and for each occurrence of the bracketed structure n, at least one of $R^1$, $R^2$, $R^3$, $R^4$, $R^5$ and $R^6$ comprises a carbonyl group suitable for oxime formation.

Examples of suitable organic moieties are aliphatic groups having a chain of atoms in a range of between about one and twelve atoms, hydroxyl, hydroxyalkyl, amine, carboxyl, amide, carboxylic ester, thioester, aldehyde, nitryl, isonitryl, nitroso, hydroxylamine, mercaptoalkyl, heterocycle, carbamates, carboxylic acids and their salts, sulfonic acids and their salts, sulfonic acid esters, phosphoric acids and their salts, phosphate esters, polyglycol ethers, polyamines, polycarboxylates, polyesters, polythioesters, pharmaceutically useful groups, a biologically active substance or a diagnostic label.

In certain embodiments, in the polyacetals and polyketals described directly above, for each occurrence of the bracketed structure n, at least one of $R^1$, $R^2$, $R^3$, $R^4$, $R^5$ and $R^6$ includes comprises a functional group that increases the polymer hydrophilicity or is adapted for covalent binding to linker $L^M$.

In certain embodiments, in the polyacetals and polyketals described directly above, for each occurrence of the bracketed structure n, at least one of $R^1$, $R^2$, $R^3$, $R^4$, $R^5$ and $R^6$ includes comprises a carbonyl group adapted for covalent binding to linker $L^M$. In certain exemplary embodiments, the polyacetals and polyketals described directly above, wherein at least one of $R^1$, $R^2$, $R^3$, $R^4$, $R^5$ and $R^6$ comprises a carbonyl group, are conjugated with one or more moieties having the structure $H_2N$—O-$L^1$; wherein each occurrence of $L^1$ comprises a modifier or comprises a functional group adapted for covalent binding to a modifier.

In yet another embodiments, at least one of $R^1$, $R^2$, $R^3$, $R^4$, $R^5$ and $R^6$ contains a chiral moiety.

In certain embodiments, the biodegradable biocompatible carriers of the invention can be crosslinked. A suitable crosslinking agent has the formula $X^1$—(R)—$X^2$, where R is a spacer group and $X^1$ and $X^2$ are reactive groups. $X^1$ and $X^2$ can be different or the same. The spacer group R may be an aliphatic, alicyclic, heteroaliphatic, heteroalicyclic, aryl or heteroaryl moiety. Examples of suitable spacer groups include biodegradable or nonbiodegradable groups, for example, aliphatic groups, carbon chains containing biodegradable inserts such as disulfides, esters, etc. The term "reactive group," as it relates to $X^1$ and $X^2$, means functional groups which can be connected by a reaction within the biodegradable biocompatible polyals, thereby crosslinking the biodegradable biocompatible polyals. Suitable reactive groups which form crosslinked networks with the biodegradable biocompatible polyals include epoxides, halides, tosylates, mesylates, carboxylates, aziridines, cyclopropanes, esters, N-oxysuccinimide esters, disulfides, anhydrides etc.

In certain exemplary embodiments, the carrier is a biodegradable biocompatible polyketal that is crosslinked with epibromohydrin, or epichlorohydrin. In certain embodiments, the epibromohydrin or epichlorohydrin is present in an amount in the range of between about one and about twenty five percent by weight of the crosslinked biodegradable biocompatible polyketals.

Alternatively, the term "reactive" group as it relates to $X^1$ and $X^2$ means a nucleophilic group that can be reacted with an aldehyde intermediate of the biodegradable biocompatible polyals, thereby crosslinking the biodegradable biocompatible polykals. Suitable reactive groups for the aldehyde intermediate include amines, thiols, polyols, alcohols, ketones, aldehydes, diazocompounds, boron derivatives, ylides, isonitriles, hydrazines and their derivatives and hydroxylamines and their derivatives, etc.

In one embodiment, the biodegradable biocompatible polyals of the present invention have a molecular weight of between about 0.5 and about 1500 kDa. In a preferred embodiment of the present invention, the biodegradable biocompatible polyals have a molecular weight of between about 1 and about 1000 kDa.

In certain embodiments, the polymer carriers are modified (i.e., conjugated with one or more modifiers) at one or both termini. For example, when the carrier is a polyketal, the carrier may have the structure:

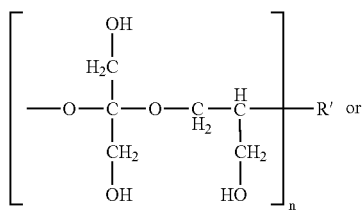

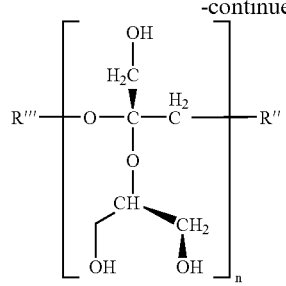

wherein n is an integer and R', R" and R'" may be a modifier. For example, R' can comprise an N-hydroxysuccinimide ester or a maleimide moiety for conjugation with proteins or other biomolecules; R" and R'" can comprise a phospholipid and a target specific moiety, such as antibody, respectively, for liposome modification.

In certain other embodiments, carriers can be substituted at one terminal and one or more non-terminal positions, or at both terminal and one or more non-terminal positions.

In certain embodiments, the carrier is a linear macromolecule, a branched macromolecule, a globular macromolecule, a graft copolymer, a comb copolymer, a nanoparticle or a lipid-based carrier. In certain exemplary embodiments, the lipid-based carrier is a liposome.

Modifiers

In certain embodiments, modifiers according to the invention include, but are not limited to, biomolecules, small molecules, therapeutic agents, microparticles, pharmaceutically useful groups or entities, macromolecules, diagnostic labels, chelating agents, hydrophilic moieties, dispersants, charge modifying agents, viscosity modifying agents, surfactants, coagulation agents and flocculants, to name a few.

Examples of biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, and RNA.

Examples of small molecules include, but are not limited to, drugs such as vitamins, anti-AIDS substances, anti-cancer substances, antibiotics, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anticoagulants and/or antithrombotic agents, local anesthetics, ophthalmics, prostaglandins, anti-depressants, anti-psychotic substances, anti-emetics and imaging agents.

Examples of suitable pharmaceutically useful groups or entities include, but are not limited to, hydrophilicity/hydrophobicity modifiers, pharmacokinetic modifiers, biologically active modifiers and detectable modifiers.

Examples of diagnostic labels include, but are not limited to, diagnostic radiopharmaceutical or radioactive isotopes for gamma scintigraphy and PET, contrast agent for Magnetic Resonance Imaging (MRI) (for example paramagnetic atoms and superparamagnetic nanocrystals), contrast agent for computed tomography, contrast agent for X-ray imaging method, agent for ultrasound diagnostic method, agent for neutron activation, and moiety which can reflect, scatter or affect X-rays, ultrasounds, radiowaves and microwaves, fluorophores in various optical procedures, etc. Diagnostic radiopharmaceuticals include γ-emitting radionuclides, e.g., indium-111, technetium-99m and iodine-131, etc. Contrast agents for MRI (Magnetic Resonance Imaging) include magnetic compounds, e.g. paramagnetic ions, iron, manganese, gadolinium, lanthanides, organic paramagnetic moieties and superparamagnetic, ferromagnetic and antiferromagnetic compounds, e.g., iron oxide colloids, ferrite colloids, etc. Contrast agents for computed tomography and other X-ray based imaging methods include compounds absorbing X-rays, e.g., iodine, barium, etc. Contrast agents for ultrasound based methods include compounds which can absorb, reflect and scatter ultrasound waves, e.g., emulsions, crystals, gas bubbles, etc. Still other examples include substances useful for neutron activation, such as boron and gadolinium. Further, labels can be employed which can reflect, refract, scatter, or otherwise affect X-rays, ultrasounds, radiowaves, microwaves and other rays useful in diagnostic procedures. Fluorescent labels can be used for photoimaging. In certain embodiments a modifier comprises a paramagnetic ion or group.

In certain embodiments, a modifier of the invention comprises at least one functional group suitable for covalent binding with a carbonyl group present on a carrier via an oxime linkage.

Alternatively, or additionally, a modifier may be adapted for covalent binding with a carbonyl group present on a carrier via an oxime linkage. For example, a modifier may be covalently attached to a linker moiety comprising a functional group that can form an oxime linkage with a carbonyl group present on a carrier. For instance, the inventive modifiers may have the structure:

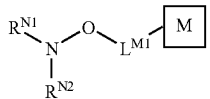

wherein M is a modifier; $L^{M1}$ is a substituted or unsubstituted, cyclic or acyclic, linear or branched $C_{0-12}$alkylidene or $C_{0-12}$alkenylidene moiety wherein up to two non-adjacent methylene units are independently optionally replaced by CO, $CO_2$, COCO, $CONR^{Z1}$, $OCONR^{Z1}$, $NR^{Z1}NR^{Z2}$, $NR^{Z1}NR^{Z2}CO$, $NR^{Z1}CO$, $NR^{Z1}CO_2$, $NR^{Z1}CONR^{Z2}$, SO, $SO_2$, $NR^{Z1}SO_2$, $SO_2NR^{Z1}$, $NR^{Z1}SO_2NR^{Z2}$, O, S, or $NR^{Z1}$; wherein each occurrence of $R^{Z1}$ and $R^{Z2}$ is independently hydrogen, alkyl, heteroalkyl, aryl, heteroaryl or acyl; and $R^{N1}$ and $R^{N2}$ are independently hydrogen, an aliphatic, alicyclic, heteroaliphatic, heterocyclic, aryl or heteroaryl moiety, or a nitrogen protecting group, or $R^{N1}$ and $R^{N2}$, taken together with the nitrogen atom to which they are attached, form a substituted or unsubstituted heterocyclic or heteroaryl moiety.

In certain exemplary embodiments, $L^{M1}$ comprises an NHS ester crosslinker and the compound has the structure:

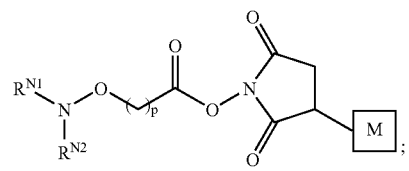

wherein p is 0-5.

In certain other exemplary embodiments, $L^1$ comprises a maleimide crosslinker and the compound has the structure:

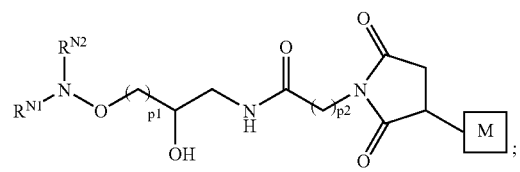

wherein $p_1$ and $p_2$ are independently integers from 1-5.

In certain exemplary embodiments, in the compounds having the structure:

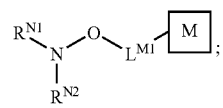

$R^{N1}R^{N2}N$— is a moiety having the structure:

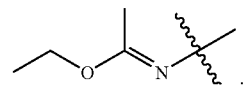

In other exemplary embodiments, $R^{N1}R^{N2}N$— is —$NH_2$.

In another aspect, the invention provides bifunctional compounds suitable for covalently binding a carrier and one or more modifiers via oxime linkages. In certain embodiments, the bifunctional compounds comprise (i) a functional group suitable for covalent binding with a carbonyl group present on a carrier via an oxime linkage; and (ii) a functional group Q suitable for covalent attachment to a modifier.

In certain exemplary embodiments, the inventive bifunctional compounds have the structure $R^{N1}R^{N2}N$—O-$L^1$; wherein $R^{N1}$ and $R^{N2}$ are independently hydrogen, an aliphatic, alicyclic, heteroaliphatic, heterocyclic, aryl or heteroaryl moiety, or a nitrogen protecting group, or $R^{N1}$ and $R^{N2}$, taken together with the nitrogen atom to which they are attached, form a substituted or unsubstituted heterocyclic or heteroaryl moiety; and $L^1$ is an aliphatic, alicyclic, heteroaliphatic, heterocyclic, aryl or heteroaryl moiety comprising a functional group adapted for covalent binding to a modifier.

In certain exemplary embodiments, $L^1$ is a moiety having the structure —$(CR^{L1}R^{L2})_p$-Q-, wherein p is an integer from 0-6, $R^{L1}$ and $R^{L2}$ are independently hydrogen, an aliphatic, alicyclic, heteroaliphatic, heterocyclic, aryl or heteroaryl moiety or $WR^{W1}$ wherein W is O, S, NH, CO, $SO_2$, COO, CONH, and $R^{W1}$ is hydrogen, an aliphatic, alicyclic, heteroaliphatic, heterocyclic, aryl, heteroaryl, alkylaryl or alkylheteroaryl moiety, and Q is a moiety comprising a functional group adapted for covalent binding to a modifier. In certain other exemplary embodiments, $L^1$ is —$(CH_2)_p$— wherein p is an integer from 0-5. In yet other exemplary embodiments, $L^1$ is —$(CH_2)_{p_1}$—CH(OH)CH$_2$NH— wherein $p_1$ is an integer from 1-5.

In certain embodiments, Q comprises an active ester moiety useful for conjugation with amino groups. In certain exemplary embodiments, Q comprises N-hydroxy succinimide ester, tetrafluorophenyl ester or nitrophenyl ester. In certain other exemplary embodiments, Q comprises a succinimidyl ester moiety having the structure:

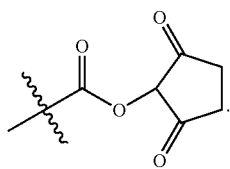

In certain embodiments, Q comprises a maleimido moiety useful for conjugation with thio groups. In certain other exemplary embodiments, Q comprises a succinimidyl ester moiety having the structure:

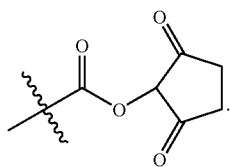

In certain other exemplary embodiments, $L^1$ is —$(CH_2)_p$— wherein p is an integer from 0-5; and Q a maleimidyl moiety having the structure:

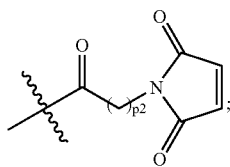

wherein $p_2$ is an integer from 1-5.

In yet other exemplary embodiments, $L^1$ is —$(CH_2)_p$—CH(OH)CH$_2$NH— wherein $p_1$ is an integer from 1-5, and Q is a maleimidyl moiety having the structure:

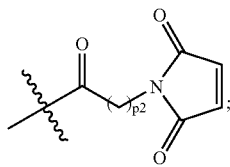

wherein $p_2$ is an integer from 1-5.

In certain embodiments, one of $R^{N1}$ and $R^{N2}$ is a nitrogen protecting group. Nitrogen protecting groups, as well as protection and deprotection methods are known in the art. Guidance may be found in "Protective Groups in Organic Synthesis" Third Ed. Greene, T. W. and Wuts, P. G., Eds., John Wiley & Sons, New York: 1999, the entire contents of which are hereby incorporated by reference. In certain exemplary embodiments, $R^{N1}$ and $R^{N2}$ are each hydrogen.

In certain exemplary embodiments, in the bifunctional compounds of the invention, $R^{N1}R^{N2}N$— is a moiety having the structure:

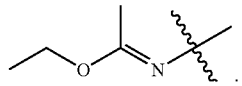

Conjugates

Conjugates of the invention comprise one or more occurrences of M, where M is a modifier, wherein the one or more occurrences of M may be the same or different. In certain embodiments, one or more occurrences of M are biocompatible moieties. In certain embodiments, one or more occurrences of M are hydrophilic moieties.

In certain other embodiment, one or more occurrences of M comprise, or are attached to the carrier through, a biodegradable bond. In certain exemplary embodiments, the biodegradable bond is selected from the group consisting of acetal, ketal, amide, ester, thioester, enamine, inline, imide, dithio, and phosphoester bond.

In other embodiments, in the conjugates of the invention, one or more occurrences of M comprise a biologically active modifier. In certain exemplary embodiments, one or more occurrence of M is selected from the group consisting of proteins, antibodies, antibody fragments, peptides, antineoplastic drugs, hormones, cytokines, enzymes, enzyme substrates, receptor ligands, lipids, nucleotides, nucleosides, metal complexes, cations, anions, amines, heterocycles, heterocyclic amines, aromatic groups, aliphatic groups, intercalators, antibiotics, antigens, immunomodulators, and antiviral compounds.

In certain other embodiments, one or more occurrence of M comprises a detectable label. In certain exemplary embodiments, one or more occurrence of M comprises atoms or groups of atoms comprising radioactive, paramagnetic, superparamagnetic, fluorescent, or light absorbing structural domains.

In certain other embodiments, one or more occurrences of M comprise a diagnostic label. In certain exemplary embodiments, one or more occurrence of M comprises radiopharmaceutical or radioactive isotopes for gamma scintigraphy and PET, contrast agent for Magnetic Resonance Imaging (MRI), contrast agent for computed tomography, contrast agent for X-ray imaging method, agent for ultrasound diagnostic method, agent for neutron activation, moiety which can reflect, scatter or affect X-rays, ultrasounds, radiowaves, microwaves and/or fluorophores.

In certain exemplary embodiments, the inventive conjugate comprises a biologically active modifier and a detectable label.

The biodegradable biocompatible polykal conjugates of the invention can be prepared to meet desired requirements of biodegradability and hydrophilicity. For example, under physiological conditions, a balance between biodegradability and stability can be reached. For instance, it is known that macromolecules with molecular weights beyond a certain threshold (generally, above 50-100 kDa, depending on the physical shape of the molecule) are not excreted through kidneys, as small molecules are, and can be cleared from the body only through uptake by cells and degradation in intracellular compartments, most notably lysosomes. This observation exemplifies how functionally stable yet biodegradable materials may be designed by modulating their stability under general physiological conditions (pH=7.5±0.5) and at lysosomal pH (pH near 5). For example, hydrolysis of acetal and ketal groups is known to be catalyzed by acids, therefore polyals will be in general less stable in acidic lysosomal environment than, for example, in blood plasma. One can design a test to compare polymer degradation profile at, for example, pH=5 and pH=7.5 at 37° C. in aqueous media, and thus to determine the expected balance of polymer stability in normal physiological environment and in the "digestive" lysosomal compartment after uptake by cells. Polymer integrity in such tests can be measured, for example, by size exclusion HPLC. In many cases, it will be preferable that at pH=7.5 the effective size of the polymer will not detectably change over 1 to 7 days, and remain within 50% from the original for at least several weeks. At pH=5, on the other hand, the polymer should preferably detectably degrade over 1 to 5 days, and be completely transformed into low molecular weight fragments within a two-week to several-month time frame. Although faster degradation may be in some cases preferable, in general it may be more desirable that the polymer degrades in cells with the rate that does not exceed the rate of metabolization or excretion of polymer fragments by the cells.

Accordingly, the conjugates of the present invention are expected to be biodegradable, in particular upon uptake by cells, and relatively "inert" in relation to biological systems. The products of degradation are preferably uncharged and do not significantly shift the pH of the environment. It is proposed that the abundance of alcohol groups may provide low rate of polymer recognition by cell receptors, particularly of phagocytes. The polymer backbones of the present invention generally contain few, if any, antigenic determinants (characteristic, for example, for polysaccharides and polypeptides) and generally do not comprise rigid structures capable of engaging in "key-and-lock" type interactions. Thus, the soluble, crosslinked and solid conjugates of this invention are predicted to have low toxicity and bioadhesivity, which makes them suitable for several biomedical applications.

In certain embodiments of the present invention, the biodegradable biocompatible polyal conjugates can form linear or branched structures. The biodegradable biocompatible polyal conjugates of the present invention can be chiral (optically active). Optionally, the biodegradable biocompatible polyal conjugates of the present invention can be racemic.

In yet another embodiment, the conjugates of the present invention are associated with a macromolecule. Examples of suitable macromolecules include, but are not limited to, enzymes, polypeptides, polylysine, proteins, lipids, polyelectrolytes, antibodies, ribonucleic and deoxyribonucleic acids and lectins. The macromolecule may be chemically modified prior to being associated with said biodegradable biocompatible conjugate. Circular and linear DNA and RNA (e.g., plasmids) and supramolecular associates thereof, such as viral particles, for the purpose of this invention are considered to be macromolecules. In certain embodiments, conjugates of the invention are non-covalently associated with macromolecules.

In certain embodiments, the conjugates of the invention are water-soluble. In certain embodiments, the conjugates of the invention are water-insoluble. In certain embodiments, the inventive conjugate is in a solid form. In certain embodiments, the conjugates of the invention are colloids. In certain embodiments, the conjugates of the invention are in particle form. In certain embodiments, the conjugates of the invention are in gel form. In certain embodiments, the conjugates of the invention are in a fiber form. In certain embodiments, the conjugates of the invention are in a film form.

Synthetic Methods

According to the present invention, any available techniques can be used to make the inventive conjugates or compositions including them, and intermediates and components (e.g., carriers and modifiers) useful for making them. For example, semi-synthetic and fully synthetic methods such as those discussed in detail below may be used.

Carriers

Methods for preparing polymer carriers (e.g., biocompatible, biodegradable polymer carriers) suitable for conjugation to modifiers are known in the art. For example, synthetic guidance can be found in U.S. Pat. Nos. 5,811,510; 5,863,990 and 5,958,398; U.S. Provisional Patent Application 60/348,333; European Patent No.: 0820473; and International Patent Application PCT/US03/01017. The skilled practitioner will know how to adapt these methods to make polymer carriers for use in the practice of the invention.

Semi Synthetic Route

For example, semi-synthetic polyals may be prepared from polyaldoses and polyketoses via complete lateral cleavage of carbohydrate rings with periodate in aqueous solutions, with subsequent conjugation of aldehyde groups with one or more modifiers or conversion into hydrophilic moieties, e.g. via borohydride reduction. In an exemplary embodiment, the carbohydrate rings of a suitable polysaccharide can be oxidized by glycol-specific reagents, resulting in the cleavage of carbon-carbon bonds between carbon atoms that are each connected to a hydroxyl group. An example of application of this methodology to dextran B-512 is illustrated below:

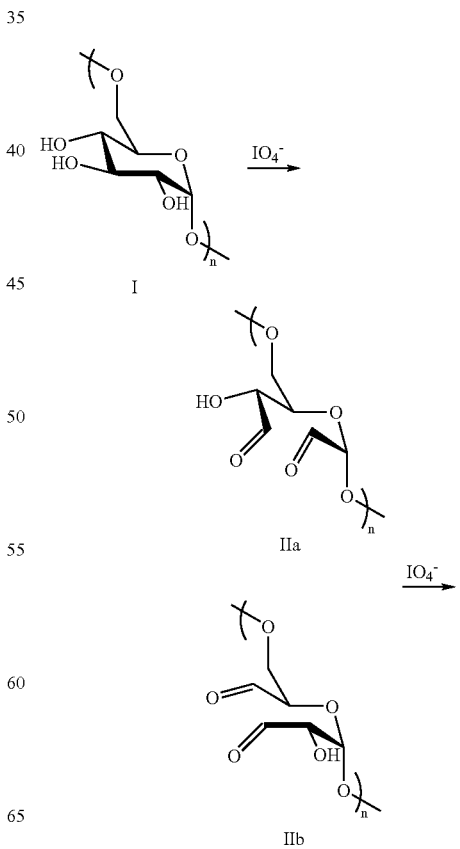

-continued

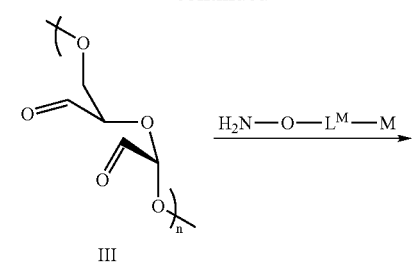
III

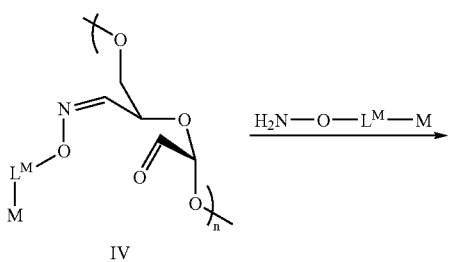
IV

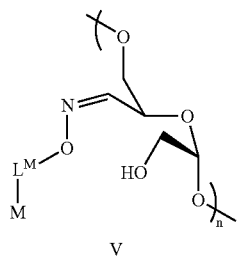
V

A similar approach may be used with Levan:

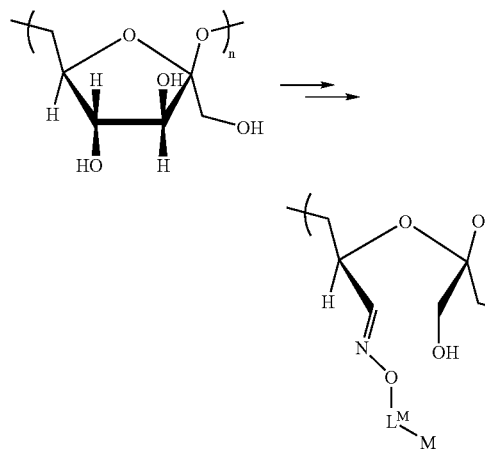

Inulin:

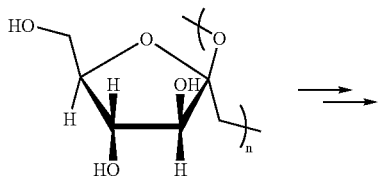

-continued

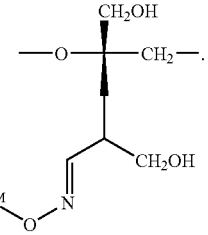

In one embodiment, a method for forming the biodegradable biocompatible polyal conjugates of the present invention comprises a process by which a suitable polysaccharide is combined with an effective amount of a glycol-specific oxidizing agent to form an aldehyde intermediate. The aldehyde intermediate, which is a polyal itself, may then be reacted with one or more suitable modifiers to form a biodegradable biocompatible polyal conjugate comprising oxime-containing linkages.

In certain exemplary embodiments, the carrier is a biodegradable biocompatible polyacetal wherein at least a subset of the polyacetal repeat structural units have the following chemical structure:

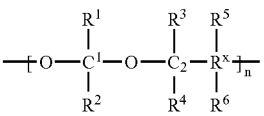

wherein for each occurrence of the n bracketed structure, one of $R^1$ and $R^2$ is hydrogen, and the other is a biocompatible group and includes a carbon atom covalently attached to $C^1$; $R^x$ includes a carbon atom covalently attached to $C^2$; n is an integer; each occurrence of $R^3$, $R^4$, $R^5$ and $R^6$ is a biocompatible group and is independently hydrogen or an organic moiety; and for each occurrence of the bracketed structure n, at least one of $R^1$, $R^2$, $R^3$, $R^4$, $R^1$ and $R^6$ comprises a carbonyl group suitable for oxime formation. In certain embodiments, the carbonyl group is an aldehyde moiety.

In yet another embodiment, the carrier is a biodegradable biocompatible polyketal wherein at least a subset of the polyketal repeat structural units have the following chemical structure:

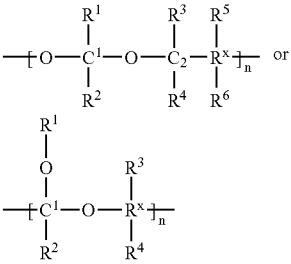

wherein each occurrence of $R^1$ and $R^2$ is a biocompatible group and includes a carbon atom covalently attached to $C^1$; $R^x$ includes a carbon atom covalently attached to $C^2$; n is an integer; each occurrence of $R^3$, $R^4$, $R^5$ and $R^6$ is a biocompatible group and is independently hydrogen or an organic moiety; and for each occurrence of the bracketed structure n, at least one of $R^1$, $R^2$, $R^3$, $R^4$, $R^5$ and $R^6$ comprises a carbonyl group suitable for oxime formation. In certain embodiments, the carbonyl group is an aldehyde moiety.

Examples of suitable organic moieties include, but are not limited to, aliphatic groups having a chain of atoms in a range of between about one and twelve atoms, hydroxyl, hydroxyalkyl, amine, carboxyl, amide, carboxylic ester, thioester, aldehyde, nitryl, isonitryl, nitroso, hydroxylamine, mercaptoalkyl, heterocycle, carbamates, carboxylic acids and their salts, sulfonic acids and their salts, sulfonic acid esters, phosphoric acids and their salts, phosphate esters, polyglycol ethers, polyamines, polycarboxylates, polyesters, polythioesters, pharmaceutically useful groups, a biologically active substance or a diagnostic label.

Structure, yield and molecular weight of the resultant polyaldehyde (i.e., polyal) depend on the initial polysaccharide. Polysaccharides that do not undergo significant depolymerization in the presence of glycol-specific oxidizing agents, for example, poly(2,1) and (2, 6) fructoses, are preferable. Examples of suitable polysaccharides include alpha and beta 2,1 and 2,6 fructans. Other exemplary polysaccharides include Inulin, Levans from plants, and bacterial fructans. Examples of suitable glycol-specific oxidizing agents include sodium periodate, lead tetra-acetate, periodic acid, etc. In certain embodiments, the oxidation system consists of a non-specific oxidizing agent in combination with glycol-specific catalyst or and intermediate oxidizer, or an electrochemical cell. Examples of suitable reducing agents include sodium borohydride, sodium cyanoborohydride, etc. Temperature, pH and reaction duration can affect the reaction rate and polymer hydrolysis rate. The reaction is preferably conducted in the absence of light. One skilled in the art can optimize the reaction conditions to obtain polymers of desired composition. The resultant polymeric aldehyde intermediate may be reacted with suitable $H_2N$—O-containing modifier moieties to generate conjugates comprising one or more modifiers covalently attached to the carrier via oxime linkages, as described in more detail below.

In certain embodiments, under physiological conditions, at least one of the aldehyde groups in the aldehyde-substituted polyal can exist in a hydrated (hem-diol) form. As such, the aldehyde group is considered a hydrophilic group. In another embodiment, the precursor carbohydrate has a chiral atom outside of the cleavage site. Thus the chirality of that atom is retained, and the polyal is chiral or optically active.

In certain embodiments, the polyals of the present invention can contain intermittent irregularities throughout the polyals, such as incompletely oxidized additional groups or moieties in the main chain or in the side chains.

Although it is generally understood that each acetal/ketal unit in a polyal of the present invention can have different $R^1$, $R^2$, $R^3$, $R^4$, $R^5$ and $R^6$ groups, in certain exemplary embodiments, more than 50% of the acetal/ketal units have the same $R^1$, $R^2$, $R^3$, $R^4$, $R^5$, and $R^6$. For example, exemplary polyals for use in this invention include polymers of the general formula:

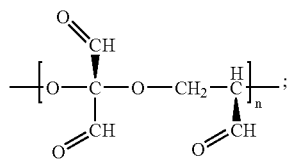

where n is an integer from 1-5000.

Since it is believed that oxidation does not affect configurations at $C^1$ and $C^2$, the polyal retain the configuration of the parent polysaccharide. Thus, the polyals (and corresponding conjugates) can be formed in stereoregular isotactic forms.

Fully Synthetic Route

In another preferred embodiment, the biodegradable biocompatible polyals of the present invention can be prepared by reacting a suitable initiator with a suitable precursor compound, as described, for example in U.S. Pat. Nos. 5,811,510; 5,863,990 and 5,958,398; U.S. Provisional Patent Application 60/348,333; European Patent No.: 0820473; and International Patent Application PCT/US03/01017.

For example, fully synthetic polyals may be prepared by condensation of vinyl ethers with protected substituted diols. Other methods, such as cycle opening polymerization, may be used, in which the method efficacy may depend on the degree of substitution and bulkiness of the protective groups.

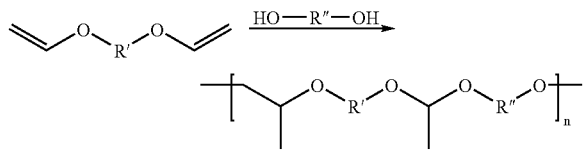

One of ordinary skill in the art will appreciate that solvent systems, catalysts and other factors may be optimized to obtain high molecular weight products.

Modifiers

As discussed above, modifiers useful in the practice of the invention may be adapted for covalent binding with a carbonyl group present on a carrier via an oxime linkage. For example, a modifier may be covalently attached to a linker moiety comprising a functional group that can form an oxime linkage with a carbonyl group present on a carrier. For instance, the inventive modifiers may have the structure:

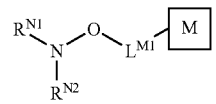

wherein M is a modifier; $L^{M1}$ is a substituted or unsubstituted, cyclic or acyclic, linear or branched $C_{0-12}$alkylidene or $C_{0-12}$alkenylidene moiety wherein up to two non-adjacent methylene units are independently optionally replaced by CO, $CO_2$, COCO, $CONR^{Z1}$, $OCONR^{Z1}$, $NR^{Z1}NR^{Z2}$, $NR^{Z1}NR^{Z2}CO$, $NR^{Z1}CO$, $NR^{Z1}CO_2$, $NR^{Z1}CONR^{Z2}$, SO, $SO_2$, $NR^{Z1}SO_2$, $SO_2NR^{Z1}$, $NR^{Z1}SO_2NR^{Z2}$, O, S, or $NR^{Z1}$; wherein each occurrence of $R^{Z1}$ and $R^{Z2}$ is independently hydrogen, alkyl, heteroalkyl, aryl, heteroaryl or acyl; and $R^{N1}$ and $R^{N2}$ are independently hydrogen, an aliphatic, alicyclic, heteroaliphatic, heterocyclic, aryl or heteroaryl moiety, or a nitrogen protecting group, or $R^{N1}$ and $R^{N2}$, taken together with the nitrogen atom to which they are attached, form a substituted or unsubstituted heterocyclic or heteroaryl moiety.

In certain embodiments, the above-described modifiers may be prepared by nucleophilic addition of an aminooxy reagent (i) with a suitable modifier-containing reagent (ii), as shown below:

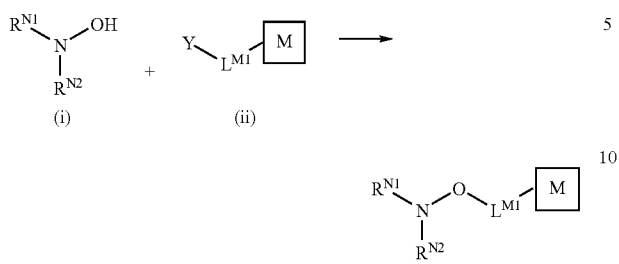

wherein Y is a suitable leaving group.

In certain embodiments, the modifier-containing reagent (ii) may be prepared by nucleophilic addition of a modifier M with a suitable linker (iii), as shown below:

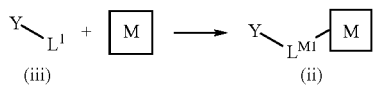

wherein $L^1$ is an aliphatic, alicyclic, heteroaliphatic, heterocyclic, aryl or heteroaryl moiety comprising a functional group adapted for covalent binding to the modifier.

In certain other embodiments, the above-described modifiers may be prepared by nucleophilic addition of an aminooxy reagent (i) with a suitable linker (iii), followed by reaction of the resulting adduct (iv) with a suitable modifier M, as shown below:

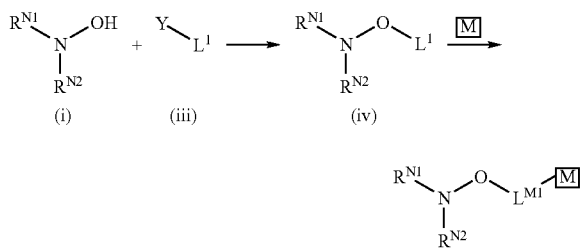

wherein Y is a suitable leaving group; and $L^1$ is an aliphatic, alicyclic, heteroaliphatic, heterocyclic, aryl or heteroaryl moiety comprising a functional group adapted for covalent binding to the modifier.

In certain exemplary embodiments, $L^1$ is a moiety having the structure —$(CR^{L1}R^{L2})_p$-Q-, wherein p is an integer from 0-6, $R^{L1}$ and $R^{L2}$ are independently hydrogen, an aliphatic, alicyclic, heteroaliphatic, heterocyclic, aryl or heteroaryl moiety or $WR^{W1}$ wherein W is O, S, NH, CO, $SO_2$, COO, CONH, and $R^{W1}$ is hydrogen, an aliphatic, alicyclic, heteroaliphatic, heterocyclic, aryl, heteroaryl, alkylaryl or alkylheteroaryl moiety, and Q is a moiety comprising a functional group adapted for covalent binding to a modifier. In certain other exemplary embodiments, $L^1$ is —$(CH_2)_p$ wherein p is an integer from 0-5. In yet other exemplary embodiments, $L^1$ is —$CH_2)_{p1}$—$CH(OH)CH_2NH$— wherein $p_1$ is an integer from 1-5.

In certain embodiments, Q comprises an active ester moiety useful for conjugation with amino groups. In certain exemplary embodiments, Q comprises N-hydroxy succinimide ester, tetrafluorophenyl ester or nitrophenyl ester. In certain other exemplary embodiments, Q comprises a succinimidyl ester moiety having the structure:

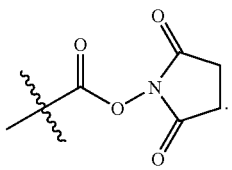

In certain embodiments, Q comprises a maleimido moiety useful for conjugation with thio groups. In certain other exemplary embodiments, Q comprises a succinimidyl ester moiety having the structure:

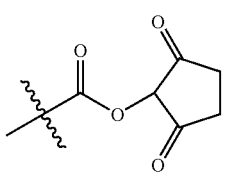

In certain other exemplary embodiments, $L^1$ is —$(CH_2)_p$ wherein p is an integer from 0-5; and Q a maleimidyl moiety having the structure:

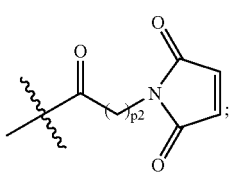

wherein $p_2$ is an integer from 1-5.

In yet other exemplary embodiments, $L^1$ is —$(CH_2)_{p1}$—$CH(OH)CH_2NH$— wherein $p_1$ is an integer from 1-5, and Q is a maleimidyl moiety having the structure:

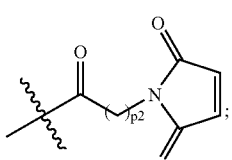

wherein $p_2$ is an integer from 1-5.

In certain embodiments, one of $R^{N1}$ and $R^{N2}$ is a nitrogen protecting group. Nitrogen protecting groups, as well as protection and deprotection methods are known in the art. Guidance may be found in "Protective Groups in Organic Synthesis" Third Ed. Greene, T. W. and Wuts, P. G., Eds., John Wiley & Sons, New York: 1999, the entire contents of which are hereby incorporated by reference.

In certain exemplary embodiments, $R^{N1}R^{N2}N$— is a moiety having the structure:

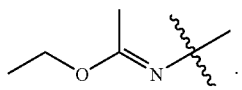

In yet other exemplary embodiments, $L^1$ is —$CH_2)_{p1}$—CH(OH)CH$_2$NH-Q wherein $p_1$ is an integer from 1-5; $R^{N1}R^{N2}N$— is a moiety having the structure:

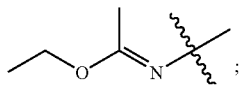

wherein Q is a moiety comprising a functional group adapted for covalent binding to a modifier, and the invention provides compounds having the structure:

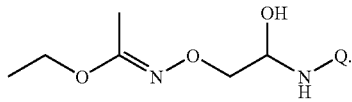

In certain exemplary embodiments, the compounds described directly above may be prepared by reaction of oxime (v) with epichlorohydrine (vi) to form the corresponding epoxide adduct (vii), followed by reacting (vii) with a suitable nucleophile R—ZH to give adduct (viii), wherein Z is a nucleophilic atom (e.g., O, S, NH) and R is hydrogen, an organic moiety comprising Q, or an organic moiety that can be modified to incorporate Q.

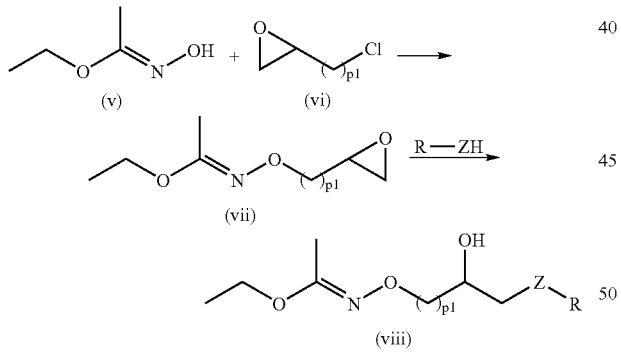

Oxime (viii) can deprotected in mild acidic conditions to give bifunctional compound (ix):

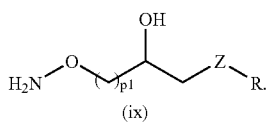

In certain embodiments, R comprises an active ester moiety useful for conjugation with amino groups. In certain exemplary embodiments, R comprises N-hydroxy succinimide ester, tetrafluorophenyl ester or nitrophenyl ester. In certain other exemplary embodiments, R comprises a succinimidyl ester moiety having the structure:

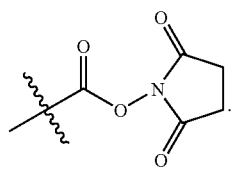

In certain embodiments, R comprises a maleimido moiety useful for conjugation with thio groups. In certain other exemplary embodiments, R comprises a succinimidyl ester moiety having the structure:

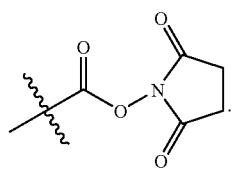

In certain embodiments, R is a carboxyl. In another embodiment, R is a second aminooxy group.

Conjugates

In another aspect, the invention provides a method for preparing a conjugate comprising a carrier substituted with one or more occurrences of a moiety having the structure:

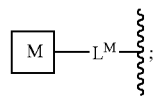

wherein each occurrence of M is independently a modifier; and each occurrence of $L^M$ is independently an oxime-containing linker;

said method comprising steps of:

providing a carrier;

providing one or more modifiers;

providing one or more compounds having the structure: $R^{N1}R^{N2}N$—O-$L^1$; wherein $R^{N1}$ and $R^{N2}$ are independently hydrogen, an aliphatic, alicyclic, heteroaliphatic, heterocyclic, aryl or heteroaryl moiety, or a nitrogen protecting group, or $R^{N1}$ and $R^{N2}$, taken together, form a substituted or unsubstituted alicyclic, aryl or heteroaryl moiety; and each occurrence of $L^1$ is independently an aliphatic, alicyclic, heteroaliphatic, heterocyclic, aryl or heteroaryl moiety comprising a functional group adapted for covalent binding to the modifier; and reacting the one or more compounds of structure $R^{N1}R^{N2}N$—O-$L^1$ with the carrier and the one or more modifiers under suitable conditions so that at least one —O—$NR^{N1}R^{N2}$ moiety is covalently attached to the carrier via an oxime linkage, thereby generating the conjugate.

In another aspect, the invention provides a method for preparing a conjugate comprising a carrier substituted with one or more occurrences of a moiety having the structure:

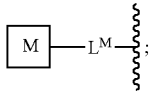

wherein each occurrence of M is independently a modifier; and each occurrence of $L^M$ is independently an oxime-containing linker;

said method comprising steps of:

providing a carrier;

providing one or more compounds having the structure:

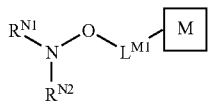

wherein $L^{M1}$ is a substituted or unsubstituted, cyclic or acyclic, linear or branched $C_{0-12}$alkylidene or $C_{0-12}$alkenylidene moiety wherein up to two non-adjacent methylene units are independently optionally replaced by CO, $CO_2$, COCO, $CONR^{Z1}$, $OCONR^{Z1}$, $NR^{Z1}NR^{Z2}$, $NR^{Z1}NR^{Z2}CO$, $NR^{Z1}CO$, $NR^{Z1}CO_2$, $NR^{Z1}CONR^{Z2}$, SO, $SO_2$, $NR^{Z1}SO_2$, $SO_2NR^{Z1}$, $NR^{Z1}SO_2NR^{Z2}$, O, S, or $NR^{Z1}$; wherein each occurrence of $R^{Z1}$ and $R^{Z2}$ is independently hydrogen, alkyl, heteroalkyl, aryl, heteroaryl or acyl; and $R^{N1}$ and $R^{N2}$ are independently hydrogen, an aliphatic, alicyclic, heteroaliphatic, heterocyclic, aryl or heteroaryl moiety, or a nitrogen protecting group, or $R^{N1}$ and $R^{N2}$, taken together with the nitrogen atom to which they are attached, form a substituted or unsubstituted heterocyclic or heteroaryl moiety; and reacting the carrier with the one or more compounds of structure:

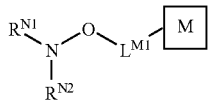

under suitable conditions so that at least one —O—$NR^{N1}R^{N2}$ moiety is covalently attached to the carrier via an oxime linkage, thereby generating the conjugate.

In certain exemplary embodiments, $R^{N1}$ and $R^{N2}$ are each hydrogen. In certain exemplary embodiments, in the one or more compounds of structure $R^{N1}R^{N2}N$—O-$L^1$; at least one of $R^{N1}$ and $R^{N2}$ is a nitrogen protecting group; and the method further comprises the step of hydrolyzing the one or more compounds having the structure $R^{N1}R^{N2}N$—O-$L^1$ to form one or more compounds having the structure $H_2N$—O-$L^1$ prior to reacting with the carrier. In certain exemplary embodiments, in the one or more compounds of structure $R^{N1}R^{N2}N$—O-$L^1$, $R^{N1}R^{N2}N$— has the structure $CH_3CH_2OC(CH_3)$=N—; and the one or more compounds have the following structure:

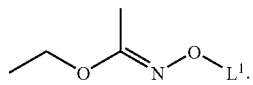

In certain exemplary embodiments, in the one or more compounds of structure

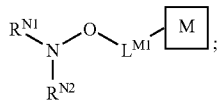

at least one of $R^{N1}$ and $R^{N2}$ is a nitrogen protecting group; and the method further comprises the step of hydrolyzing the one or more compounds having the structure:

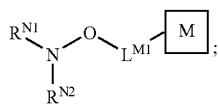

to form one or more compounds having the structure:

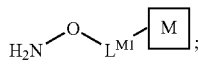

prior to reacting with the carrier.

In certain exemplary embodiments, in the one or more compounds of structure:

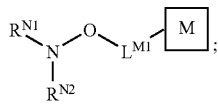

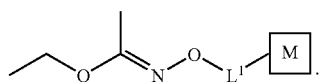

$R^{N1}R^{N2}N$— has the structure $CH_3CH_2OC(CH_3)$=N—; and the one or more compounds have the following structure:

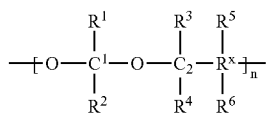

In certain exemplary embodiments, in practicing the method of the invention, the carrier is a biodegradable biocompatible polyacetal wherein at least a subset of the polyacetal repeat structural units have the following chemical structure:

$$+O-\underset{R^2}{\overset{R^1}{C^1}}-O-\underset{R^4}{\overset{R^3}{C_2}}-\underset{R^6}{\overset{R^5}{R^x}}+_n$$

wherein for each occurrence of the n bracketed structure, one of $R^1$ and $R^2$ is hydrogen, and the other is a biocompatible group and includes a carbon atom covalently attached to $C^1$; $R^x$ includes a carbon atom covalently attached to $C^2$; n is an integer; each occurrence of $R^3$, $R^4$, $R^5$ and $R^6$ is a biocompatible group and is independently hydrogen or an organic moiety; and for each occurrence of the bracketed structure n, at least one of $R^1$, $R^2$, $R^3$, $R^4$, $R^5$ and $R^6$ comprises a carbonyl group suitable for oxime formation. In certain embodiments, the carbonyl group is an aldehyde moiety.

In certain exemplary embodiments, in practicing the method of the invention, the carrier is a biodegradable biocompatible polyketal wherein at least a subset of the polyketal repeat structural units have the following chemical structure:

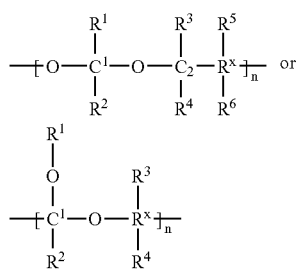

wherein each occurrence of $R^1$ and $R^2$ is a biocompatible group and includes a carbon atom covalently attached to $C^1$; $R^x$ includes a carbon atom covalently attached to $C^2$; n is an integer; each occurrence of $R^3$, $R^4$, $R^5$ and $R^6$ is a biocompatible group and is independently hydrogen or an organic moiety; and for each occurrence of the bracketed structure n, at least one of $R^1$, $R^2$, $R^3$, $R^4$, $R^5$ and $R^6$ comprises a carbonyl group suitable for oxime formation. In certain embodiments, the carbonyl group is an aldehyde moiety.

Bifunctional compounds $R^{N1}R^{N2}N$—O-$L^1$ and modifiers of the structure:

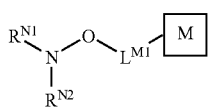

of both protected (i.e., $R^{N1}R^{N2}N$— is a protected nitrogen moiety) and deprotected (i.e., $R^{N1}$ and $R^{N2}$ are each hydrogen) types can be used in conjugation. The latter may be performed in a variety of ways. For example, a protected or deprotected maleimido-aminooxy reagent can be first conjugated with thiol groups present in a modifier (e.g., in a protein or peptide). If a protected form of reagent was used, the protection can be removed under conditions suitable to remove the selected nitrogen protecting group. For example, $R^{N1}R^{N2}N$— is a moiety having the structure:

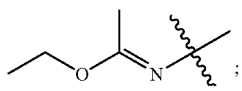

nitrogen deprotection can be effected, in aqueous media at pH<7, preferably from 2 to 4. Then, the resultant aminooxyderivative can be conjugated with a carbonyl-comprising carrier in aqueous media at pH 3 to 6, preferably 4 to 5. Conjugation can be performed using a mixture of bifunctional compounds $R^{N1}R^{N2}N$—O-$L^1$ and/or modifiers of the structure:

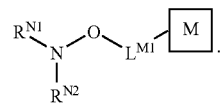

Conversion (conjugation) degree can be monitored by any suitable method, for example HPLC. When the desirable conversion degree has been achieved, the product can be purified (e.g., by gel chromatography) and isolated (e.g., via lyophilization). Conversely, the bifunctional reagent can be first reacted with a carbonyl-comprising carrier, and then the "activated" product can be reacted with the respective modifier.

To obtain a conjugate containing a set of different modifiers, conjugation can be performed in one step in a mixture of aminooxy-containing modifiers having the structure:

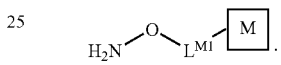

The latter can be synthesized, for example, as described above. Then, all modifiers can be mixed with the carbonyl-containing carrier and the reaction mixture incubated in the described conditions until the desirable conversion degree is achieved. This method can be used, via mixing the modifiers and the carrier at different ratios, to produce, in one step, libraries of conjugates with varying modifier composition and content.

In either one of the above methods, the residual unreacted aminooxy bifunctional reagent and/or modifier, as well as unreacted carbonyl groups on the carrier can be "quenched", if desired, with a suitable reagent. For example, carbonyl groups can be either oxidized into carboxyls (e.g., with iodine), or reacted with a suitable aminooxy-substituted compound, e.g., 1-aminooxy-propanediol-2,3. Unreacted aminooxygroups can be reacted with a suitable aldehyde or ketone (e.g., acetaldehyde).

Compositions

In certain embodiments, there is provided a composition comprising any one or more of the conjugates disclosed herein and a pharmaceutically suitable carrier or diluent.

In certain embodiments, the invention provides a composition in the form of a gel of the inventive biodegradable biocompatible polyal conjugate and a biologically active compound disposed within the gel. Alternatively or additionally, a diagnostic label can be disposed within the gel or bound to the gel matrix.

In another embodiment, the invention provides a composition in the form of a solution of the biodegradable biocompatible polyal conjugate and a pharmaceutically useful entity, a drug or a macromolecule dissolved within the solution. Alternatively or additionally, a diagnostic label can be dissolved within the solution.

In certain embodiments, there is provided a composition comprising a biodegradable biocompatible polyal conjugate of the invention associated with an effective amount of a therapeutic agent; wherein the therapeutic agent is incorporated into an released from said biodegradable biocompatible polyal conjugate matrix by degradation of the polymer matrix or diffusion of the agent out of the matrix over a period of time. In certain embodiments, polyal conjugate is non-covalently associated with an effective amount of a therapeutic agent. In certain embodiments, the therapeutic agent is selected from the group consisting of vitamins, anti-AIDS substances, anti-cancer substances, antibiotics, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anticoagulants and/or antithrombotic agents, local anesthetics, ophthalmics, prostaglandins, anti-depressants, anti-psychotic substances, anti-emetics, imaging agents, and combination thereof.

In variations of these embodiments, it may be desirable to include other pharmaceutically active compounds, such as antiinflammatories or steroids which are used to reduce swelling, antibiotics, antivirals, or antibodies. Other compounds which can be included are preservatives, antioxidants, and fillers, coatings or bulking agents which may also be utilized to alter polymer matrix stability and/or drug release rates.

Additives Used to Alter Properties of Conjugate Compositions:

In a preferred embodiment, only polyal conjugate and drugs to be released are incorporated into the delivery device or construct, although other biocompatible, preferably biodegradable or metabolizable, materials can be included for processing, preservation and other purposes.

Buffers, acids and bases are used to adjust the pH of the composition. Agents to increase the diffusion distance of agents released from the implanted polymer can also be included.

Fillers are water soluble or insoluble materials incorporated into the formulation to add bulk. Types of fillers include sugars, starches and celluloses. The amount of filler in the formulation will typically be in the range of between about 1 and about 90% by weight.

Methods of Use

The present invention encompasses polymer conjugates for use in biomedical applications, primarily (but not exclusively) in the fields of pharmacology, bioengineering, wound healing, and dermatology/cosmetics. In certain embodiments, the polymer conjugates are biodegradable polyal conjugates. In particular, medical applications for the conjugates of the invention include tablet coatings, plasma substitutes, gels, contact lenses, surgical implants, systems for controlled drug release, as ingredients of eyedrops, wound closure applications (sutures, staples), orthopedic fixation devices (pins, rods, screws, tacks, ligaments), dental applications (guided tissue regeneration), cardiovascular applications (stents, grafts), intestinal applications (anastomosis rings), and as long circulating and targeted drugs. Conjugates of the present invention can be employed as components of biomaterials, drugs, drug carriers, pharmaceutical formulations, medical devices, implants, and can be associated with small molecules, pharmaceutically useful entities, drugs, macromolecules and diagnostic labels.

Methods of Treating

In certain preferred embodiments of the invention, the conjugates of the invention are used in methods of treating animals (preferably mammals, most preferably humans). In one embodiment, the conjugates of the present invention may be used in a method of treating animals which comprises administering to the animal a biodegradable biocompatible conjugates of the invention. For example, conjugates in accordance with the invention can be administered in the form of soluble linear polymers, copolymers, conjugates, colloids, particles, gels, solid items, fibers, films, etc. Biodegradable biocompatible conjugates of this invention can be used as drug carriers and drug carrier components, in systems of controlled drug release, preparations for low-invasive surgical procedures, etc. Pharmaceutical formulations can be injectable, implantable, etc.

In yet another aspect, the invention provides a method of administering to a patient in need of treatment, comprising administering to the subject an effective amount of a suitable therapeutic agent; wherein said therapeutic agent is associated with and released from a conjugate of the invention by degradation of the conjugate matrix or diffusion of the agent out of the matrix over a period of time.

In certain embodiments, the therapeutic agent is locally delivered by implantation of said conjugate matrix incorporating the therapeutic agent.

In certain embodiments, the therapeutic agent is selected from the group consisting of: vitamins, anti-AIDS substances, anti-cancer substances, antibiotics, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anticoagulants and/or antithrombotic agents, local anesthetics, ophthalmics, prostaglandins, anti-depressants, anti-psychotic substances, anti-emetics, imaging agents, and combinations thereof.

In certain other exemplary embodiments, the method further comprises administering with the therapeutic agent additional biologically active compounds selected from the group consisting of vitamins, anti-AIDS substances, anti-cancer substances, antibiotics, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anticoagulants and/or antithrombotic agents, local anesthetics, ophthalmics, prostaglandins, anti-depressants, anti-psychotic substances, anti-emetics, imaging agents, and combination thereof.

In certain embodiments, in practicing the method of the invention, the conjugate further comprises or is associated with a diagnostic label. In certain exemplary embodiments, the diagnostic label is selected from the group consisting of: radiopharmaceutical or radioactive isotopes for gamma scintigraphy and PET, contrast agent for Magnetic Resonance Imaging (MRI), contrast agent for computed tomography, contrast agent for X-ray imaging method, agent for ultrasound diagnostic method, agent for neutron activation, moiety which can reflect, scatter or affect X-rays, ultrasounds, radiowaves and microwaves and fluorophores. In certain exemplary embodiments, the conjugate is further monitored in vivo.

In another aspect, the invention provides a method of administering a conjugate of the invention to an animal, comprising preparing an aqueous formulation of said conjugate and parenterally injecting said formulation in the animal. In certain exemplary embodiments, the conjugate comprises a biologically active modifier. In certain exemplary embodiments, the conjugate comprises a detectable modifier.

In another aspect, the invention provides a method of administering a conjugate of the invention to an animal, comprising preparing an implant comprising said conjugate, and implanting said implant into the animal. In certain exemplary embodiments, the implant is a biodegradable gel matrix.

In another aspect, the invention provides a method for treating of an animal in need thereof, comprising administering a conjugate according to the methods described above, wherein said conjugate is associated with a biologically active component.

In another aspect, the invention provides a method for treating of an animal in need thereof, comprising administering a conjugate according to the methods described above, wherein said conjugate comprises a biologically active modifier. In certain exemplary embodiments, the biologically active component is a gene vector.

In another aspect, the invention provides a method for eliciting an immune response in an animal, comprising administering a conjugate as in the methods described above, wherein said conjugate comprises an antigen modifier.

In another aspect, the invention provides a method of diagnosing a disease in an animal, comprising steps of:
  administering a conjugate as in the methods described above, wherein said conjugate comprises a detectable modifier; and
  detecting the detectable modifier.

In certain exemplary embodiments, the step of detecting the detectable modifier is performed non-invasively. In certain exemplary embodiments, the step of detecting the detectable modifier is performed using suitable imaging equipment.

In one embodiment, a method for treating an animal comprises administering to the animal the biodegradable biocompatible conjugates of the invention as a packing for a surgical wound from which a tumor or growth has been removed. The biodegradable biocompatible conjugate packing will replace the tumor site during recovery and degrade and dissipate as the wound heals.

In certain embodiments, the conjugate is associated with a diagnostic label for in vivo monitoring.

The conjugates described above can be used for therapeutic, preventative, and analytical (diagnostic) treatment of animals. The conjugates are intended, generally, for parenteral administration, but in some cases may be administered by other routes.

In one embodiment, soluble or colloidal conjugates are administered intravenously. In another embodiment, soluble or colloidal conjugates are administered via local (e.g., subcutaneous, intramuscular) injection. In another embodiment, solid conjugates (e.g., particles, implants, drug delivery systems) are administered via implantation or injection.

In one embodiment, conjugates comprising a biologically active substance (e.g., a drug or a gene vector) are administered to treat disease responsive to said substance.

In another embodiment, conjugates comprising a detectable label are administered to study the patterns and dynamics of label distribution in animal body.

In another embodiment, conjugates comprising an antigen or an antigen-generating component (e.g., a plasmid) are administered to develop immunity to said antigen.

Applications to Drug Delivery Methods

Polyal-small-molecule-drug conjugates: In one embodiment, pharmaceutical agents are associated with the biodegradable biocompatible conjugate of the invention to form a biodegradable biocompatible gel or mass of conjugate in which the drug is entrapped or bound to gel matrix, or a soluble conjugate of a drug and a polyal conjugate. This can be achieved, for example, by coupling the conjugate of the invention with a drug modifier via oxime-containing linkages (for example, taxol or camptothecin (CPT)). Alternatively, the drug can be entrapped by dissolution of the drug in the presence of the biodegradable biocompatible conjugate during removal of a solvent, or during crosslinking. When soluble polyal-drug conjugates are administered (e.g., injected) into an animal, they can circulate and accumulate at a desirable site, and slowly release the drug either in circulation, or at the accumulation site, either intracellularly or extracellularly. When gels or masses are implanted into an animal, slow hydrolysis of the biodegradable biocompatible conjugate mass or gel occurs with continuous slow release of the agent in the animal at the location where its function is required. Such polymer-drug pharmaceutical compositions may afford release of the physiologically active substance into physiological fluids in vivo over a sustained period (for an example of polymer-drug conjugate, see Li, et al. "Water soluble paclitaxel prodrugs" U.S. Pat. No. 6,262,107, 2001, the entire contents of which are incorporated herein by reference). In addition, the hydrophilic conjugates of the invention may be used to stabilize drugs, as well as to solubilize otherwise insoluble compounds. For example, Paclitaxel, an anti-microtubule agent that has shown a remarkable anti-neoplastic effect in human cancer in Phase I studies and early Phase II and III trials (Horwitz et al., "Taxol, mechanisms of action and resistance," J. Natl. Cancer Inst. Monographs No. 15, pp. 55-61, 1993), has limited solubility in water, which has hampered its development for clinical trial use. The polyal-drug conjugate pharmaceutical compositions of the invention could provide water soluble taxoids to overcome the drawbacks associated with the insolubility of the drugs themselves, and also provide the advantages of accumulation in tumors, targeting to cancer cells and controlled release so that tumors may be eradicated more efficiently. Association of chemotherapeutic drugs to the conjugates of the invention may also be an attractive approach to reduce systemic toxicity and improve the therapeutic index. In particular, it is known in the art that polymers with molecular mass larger than 30 kDa do not readily diffuse through normal capillaries and glomerular endothelium, thus sparing normal tissue from irrelevant drug-mediated toxicity (Maeda and Matsumura, "Tumoritropic and lymphotropic principles of macromolecular drugs", Critical Review in Therapeutic Drug Carrier Systems, 6:193-210, 1989; Reynolds, T., "Polymers help guide cancer drugs to tumor targets—and keep them there," J. Natl. Cancer Institute, 87:1582-1584, 1995). On the other hand, it is well established that malignant tumors often have altered capillary endothelium and greater permeability than normal tissue vasculature (Maeda and Matsumura, 1989; Fidler, et al., "The biology of cancer invasion and metastasis," Adv. Cancer Res., 28:149-250, 1987). Thus, a polymer-drug conjugate, such as those described in the present invention, that would normally remain in the vasculature, may selectively leak from blood vessels into tumors, resulting in tumor accumulation of active therapeutic drug. The methods described herein could also be used to make water soluble conjugate complexes of other therapeutic agents, contrast agents and drugs.

protein-modified carriers: In certain embodiments, carriers may be associated to a protein or peptide (for example enzymes or growth factors) to form a protein/peptide-modified conjugate. Improved chemical and genetic methods have made many enzymes, proteins, and other peptides and polypeptides available for use as drugs or biocatalysts having specific catalytic activity. However, limitations exist to the use of these compounds. For example, enzymes that exhibit specific biocatalytic activity sometimes are less useful than they otherwise might be because of problems of low stability and solubility. During in vivo use, many proteins are cleared from circulation too rapidly. Some proteins have less water solubility than is optimal for a therapeutic agent that circulates through the bloodstream. Some proteins give rise to immunological problems when used as therapeutic agents. Immunological problems have been reported from manufactured proteins even where the compound apparently has the same basic structure as the homologous natural product. The use of protein/peptide-modified conjugates may help protect the protein/peptide from chemical attack, limit its adverse side effects when injected into the body, increase its size, and may thus potentially improve its therapeutic profile in vivo (e.g., safety, efficacy and stability in biological media). See for example Harris et al. "Multiarmed, monofunctional, polymer for coupling to molecules and surfaces" U.S. Pat. No. 5,932,462, 1999. Examples of proteins that may be used in this context are enzymes, recognition proteins, carrier proteins, and signaling proteins and polypeptides, such as, urokinase, catalase, hemoglobin, granulocyte colony stimulating factor (G-CSF), interferons, cytokines, leptins, insulin, etc.

Although there is no theory that predicts the optimal composition, size and shape of a macromolecule conjugate, it can be expected that, for some applications, conjugates consisting of one protein molecule and one polyal molecule will be desirable, whereas in other applications conjugates comprising several identical or different protein or peptide molecules per polyal molecule can be preferable. In one preferred embodiment, a protein is conjugated with a polyal of the invention via a terminal group of the latter. In another embodiment, one or more protein or peptide molecules are conjugated to the polyal molecule of the invention at random points.

Cationized polyal: In another embodiment, the polyals of the present invention may find use as a nucleic acid carrier vehicle for delivery of nucleic acid material to target cells in biological systems (for example in applications using adducts with DNA or Polyal-modified virus). Such material may find applications for in vivo delivery of genes or therapeutic DNA to a patient in carrying out gene therapy or DNA vaccination treatment (See for example Schacht et al. "Delivery of nucleic acid material" U.S. Pat. No. 6,312,727, 2001; German et al. "Enhanced adenovirus-assisted transfection composition and method" U.S. Pat. No. 5,830,730, 1998). For example, the polyal may be synthesized or modified so as to form a "cationized" material whereby one or more cationic sites are included or incorporated in the polyal molecule. Association or binding of this cationized hydrophilic polymer with a polyanionic nucleic acid component results in a material that may function as a DNA or nucleic acid delivery device. The nucleic acid component may comprise a polynucleotide, plasmid DNA, linear double-helical DNA, RNA or a virus. In another embodiment, the cationic polyal core may be associated, directly or indirectly, to other molecular entities or moieties, especially bioactive molecules, that modify the biological and/or physico-chemical characteristics of the complex to improve suitability or specificity for use in delivering the nucleic acid material to target cells. These other molecular entities or moieties may comprise cell-receptor targeting moieties and/or other specific bioactive agents providing, for example, membrane disrupting agents, agents capable of promoting endocytic internalization following binding to cell surface molecules, and nuclear-homing agents, useful for facilitating entry and delivery of the nucleic acid material, e.g. DNA, into cells.

Polyal-modified liposomes: In yet another embodiment, the polyals of the present invention may be associated with a liposome (see for example Dadey "Polymer-associated liposomes for drug delivery and method of manufacturing the same" U.S. Pat. No. 5,935,599, 1999). In certain embodiments, the polyal-associated liposome is formulated with a drug or a therapeutic agent to provide a drug composition that treats an underlying disease or complications associated with the disease. The polyal-associated liposome may be formulated with either water-soluble or water-insoluble drugs, or both. Therefore, a drug composition containing a polyal-associated liposome and a drug can be administered in a variety of dosage forms. A liposome is a mono- or multilamellar vesicle prepared from a phospholipid or other suitable lipids or mixtures thereof. Structurally, lamellae are bilayer membranes having polar ends of lipids in one layer forming the external surface of the spherical membrane and the polar ends of lipids in a second layer forming the internal surface of the spherical membrane. Membranes can include hydrophobic additives, such as cholesterol. The nonpolar, hydrophobic tails of the lipids in the two layers self-assemble to form the interior of the bilayer membrane. Liposomes can microencapsulate compounds, and transport the compounds through environments wherein they are normally degraded. The liposome can be prepared by conventional techniques from phosphatidylethanolamine, phosphatidylcholine, phosphatidylserine, phosphatidylinositol, phostidylglycerol, sphingomyelin, and mixtures thereof. The outer layer of a liposome can be modified with a polyal to either prevent liposome aggregation, or to prolong liposome circulation in blood, or for other purposes. Preferably, polyal molecules are chemically linked to lipid molecules constituting the outer membrane. In certain embodiments, polyal molecules are chemically linked to lipid molecules constituting the outer membrane via oxime linkages. Some or all polyal molecules can be further modified with targeting moieties that assist liposome binding to target cells or tissues. In a preferred embodiment, polyal molecules are linked to lipid molecules through terminal groups, forming lipid-polyal conjugates. The latter can be incorporated into liposomes during the process of liposome formation, e.g. by extrusion. Alternatively, polyals can be chemically bound to pre-formed liposomes comprising suitable functional groups on the outer surface (e.g., amino, mercapto, or carboxygroups).

Polyal-modified nano- and microparticles: In a further embodiment of the present invention, the polyal conjugates of the invention may be designed so as to have properties suitable for manufacturing by various processes into nanoparticles, microparticles and microspheres for applications in drug delivery systems. Polyal conjugates can be utilized in such applications as interface components, particle matrix components, or both. Where polyal conjugates are used as interface components, the (inner) particle can be a nanoparticle (e.g., iron oxide nanocrystal or combination thereof), a latex particle (e.g., polystyrene nanosphere or microsphere), a gel particle (e.g., crosslinked polyketal, polyacetal or polysaccharide gel sphere), etc. Where the polyal conjugate is used as a matrix component, alone or along with other macromolecular components or particulates, the polytal molecules can be chemically crosslinked or non-chemically associated to form a gel or a solid, and can be chemically or physically associated with a drug. The latter becomes, therefore, incorporated or entrapped in the particle, and can subsequently be released via diffusion or degradation mechanisms.

The slow-release characteristic of the polymer microparticles may also have use in the field of pharmacology where the microparticles can be used, for example, to deliver pharmacological agents in a slow and continual manner (see for example Sokoll et al. "Biodegradable targetable microparticle delivery system" U.S. Pat. No. 6,312,732, 2001). A wide range of drugs such as anti-hypertensives, analgesics, steroids and antibiotics can be used in accordance with the present invention to provide a slow release drug delivery system. Large molecules, such as proteins, can also be entrapped in micro- and nanoparticles, using methods of particle formation that do not inactivate the large molecule. Microspheres may be prepared by known methods in the art, for example, using a single emulsification process (U.S. Pat. No. 4,389,330 to Tice et al.; U.S. Pat. No. 3,691,090 to Kitajima et al.), a double emulsification process (Edwards et al., Science 276: 1868-1871, 1997), a phase inversion microencapsulation process (Mathiowitz et al., Nature 386: 410-413, 1997), or an atomization-freeze process (Putney and Burke, Nature Biotechnology 16: 153-157, 1998). In the single emulsification process, a volatile organic solvent phase containing a biodegradable polymer, an aqueous solution containing an emulsifier such as polyvinyl alcohol, and a physiologically active substance are homogenized to produce an emulsion. The solvent is evaporated and the resulting hardened microspheres are freeze-dried. In the double emulsification process, an aqueous solution which may contain a physiologically active substance and a volatile organic solvent phase containing a biodegradable polymer are homogenized to form an emulsion. The emulsion is mixed with another aqueous solution, which contains an emulsifier such as polyvinyl alcohol. Evaporation of the solvent and freeze-drying produces microspheres. In the phase inversion microencapsulation process, the drug is added to a dilute polymer solution in a solvent (e.g. dichloromethane) which is then poured rapidly into an unstirred bath of another liquid (e.g. petroleum ether) causing nano- and microspheres to form spontaneously. In the atomization-freeze process, the micronized solid physiologically active substance is suspended in a solvent phase containing a biodegradable polymer that is then atomized using sonication or air-atomization. This produces droplets that are then frozen in liquid nitrogen. Addition of another solvent in which both the polymer and the drug are insoluble extracts the solvent from the microspheres. In such processes, polyal conjugates can be used as interface components formed during or after particle formation. Preferably, the process is engineered such that polyal conjugates form a monolayer on the particle surface, which is dense enough to modify the particle surface hydrophilicity, and/or to prevent direct contact of cells and/or recognition proteins with the particle surface. This can be achieved, for example, by chemical coupling of the polyal to the surface of the pore-formed particles, or through addition of polyal-matrix polymer conjugates into technological solutions. Such conjugates (e.g., block copolymers) will, in appropriately optimized conditions, incorporate into particles such that the matrix polymer block will incorporate into the particle body, while the polyal conjugate block will be exposed on the particle surface. Similar approaches can be used for the modification of inorganic particles (such as colloids and nanocrystals) with ketals during or after their formation. Polyal conjugates can be attached to the surfaces of such particles either chemically (conjugation or grafting) or physically (adsorption). A further description of polyal conjugate use as an interface component is given in one of the following sections.

In another embodiment, the biodegradable biocompatible polyal conjugates of the present invention can be monitored in vivo by suitable diagnostic procedures. Such diagnostic procedures include nuclear magnetic resonance imaging (NMR), magnetic resonance imaging (MRI), ultrasound, X-ray, scintigraphy, positron emission tomography (PET), etc. The diagnostic procedure can detect, for example, polyal conjugate disposition (e.g., distribution, localization, density, etc.) or the release of drugs, prodrugs, biologically active compounds or diagnostic labels from the biodegradable biocompatible polyal conjugate over a period of time. Suitability of the method largely depends on the form of the administered polyal conjugate and the presence of detectable labels. For example, the size and shape of polyal conjugate implants can be determined non-invasively by NMR imaging, ultrasound tomography, or X-ray ("computed") tomography. Distribution of soluble polyal conjugate preparation comprising a gamma emitting or positron emitting radiotracer can be performed using gamma scintigraphy or PET, respectively. Microdistribution of polyal conjugate preparation comprising a fluorescent label can be investigated using photoimaging.

It is understood, for the purpose of this invention, that transfer and disposition of polyal conjugates in vivo can be regulated by modifying groups incorporated into the polyal conjugate structure, such as hydrophobic and hydrophilic modifiers, charge modifiers, receptor ligands, antibodies, etc. Such modification, in combination with incorporation of diagnostic labels, can be used for development of new useful diagnostic agents. The latter can be designed on a rational basis (e.g., conjugates of large or small molecules binding known tissue components, such as cell receptors, surface antigens, etc.), as well as through screening of libraries of polyal conjugate molecules modified with a variety of moieties with unknown or poorly known binding activities, such as synthetic peptides and oligonucleotides, small organic and metalloorganic molecules, etc.

Interface Component

In one embodiment of the present invention, the biodegradable biocompatible polyal conjugate can be used as an interface component. The term "interface component" as used herein, means a component, such as a coating or a layer on an object, to alter the character of object interaction with biological interaction with biological milieu, for example, to suppress foreign body reactions, decrease inflammatory response, suppress clot formation, etc. It should be understood that the object can be microscopic or macroscopic. Examples of microscopic objects include macromolecules, colloids, vesicles, liposomes, emulsions, gas bubbles, nanocrystals, etc. Examples of macroscopic objects include surfaces, such as surfaces of surgical equipment, test tubes, perfusion tubes, items contacting biological tissues, etc. It is believed that interface components can, for example, provide the object protection from direct interactions with cells and opsonins and, thus, to decrease the interactions of the object with the biological system.

Surfaces can be modified by the biodegradable biocompatible polyal conjugate of the present invention by, for example, conjugating functional groups of the biodegradable biocompatible polyal conjugate with functional groups present on the surface to be modified. For example, aldehyde groups of the biodegradable biocompatible polyal precursors can be linked with aminooxy groups to form oxime linkages. Alternatively, carboxyl groups of the biodegradable biocompatible polyals can be conjugated with amino, hydroxy, sulphur-containing groups, etc. In another embodiment, a biodegradable biocompatible polyal conjugate of the invention which includes a suitable terminal group can be synthesized, such as a polyalcohol having a terminal carboxylic group. A polymer can be connected to a surface by reaction of the terminal group. Examples of suitable polymers include those formed, for example, by oxidation of a reducing-end acetal group into a carboxyl group, such as by using iodine or bromine. The remainder of the polysaccharide is then oxidized by employing an effective amount of a glycol-specific oxidizing agent to form an aldehyde. The aldehydes can be selectively modified by, for example, reduction into hydroxyl groups. The resulting polymer will generally have one terminal carboxyl group that can be used for one-point modification, such as by employing a carbodiimide.

In still another embodiment, a suitable polysaccharide can be linked with a surface by reaction of a reducing or non-reducing end of the polysaccharide or otherwise, by subsequent oxidation and further conversion of the remainder of the polysaccharide to produce a polyal conjugate.

It is to be understood that the biodegradable biocompatible polyal conjugates of this invention can be conjugated with macromolecules, such as enzymes, polypeptides, proteins, etc., by the methods described above for conjugating the biodegradable biocompatible polyal conjugates with functional groups present on a surface.

The biodegradable biocompatible polyal conjugates of the invention can also be conjugated with a compound that can physically attach to a surface via, for example, hydrophobic, van der Waals, and electrostatic interactions. For example, the biodegradable biocompatible polyal precursors can be conjugated with lipids, polyelectrolytes, proteins, antibodies, lectins, etc.

It is believed that interface components can prolong circulation of macromolecular and colloidal drug carriers. Therefore, small molecules, biologically active compounds, diagnostic labels, etc., being incorporated in such carriers, can circulate throughout the body without stimulating an immunogenic response and without significant interactions with cell receptors and recognition proteins (opsonins). Further, interface components can be used to modify surfaces of implants, catheters, etc. In other embodiments of the present invention, biomedical preparations of the biodegradable biocompatible polyal conjugates of the invention can be made in various forms. Examples include implants, fibers, films, etc.

Throughout this document, various publications are referred to, each of which is hereby incorporated by reference in its entirety in an effort to more fully describe the state of the art to which the invention pertains.

The invention will now be further and specifically described by the following examples. All parts and percentages are by weight unless otherwise stated.

EQUIVALENTS

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

EXEMPLIFICATION

The practitioner has a well-established literature of polymer chemistry to draw upon, in combination with the information contained herein, for guidance on synthetic strategies, protecting groups, and other materials and methods useful for the synthesis of the conjugates of this invention.

The various references cited herein provide helpful background information on preparing polymers similar to the inventive compounds described herein or relevant intermediates, as well as information on formulation, uses, and administration of the conjugates of the invention, which may be of interest.

Moreover, the practitioner is directed to the specific guidance and examples provided in this document relating to various exemplary conjugates and intermediates thereof.

The conjugates of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

According to the present invention, any available techniques can be used to make or prepare the inventive polyal conjugates or compositions including them. For example, a variety of solution phase synthetic methods such as those discussed in detail below may be used. Alternatively or additionally, the inventive conjugates may be prepared using any of a variety combinatorial techniques, parallel synthesis and/or solid phase synthetic methods known in the art.

It will be appreciated as described below, that a variety of inventive conjugates can be synthesized according to the methods described herein. The starting materials and reagents used in preparing these compounds are either available from commercial suppliers such as Aldrich Chemical Company (Milwaukee, Wis.), Bachem (Torrance, Calif.), Sigma (St. Louis, Mo.), or are prepared by methods well known to a person of ordinary skill in the art following procedures described in such references as Fieser and Fieser 1991, "Reagents for Organic Synthesis", vols 1-17, John Wiley and Sons, New York, N.Y., 1991; Rodd 1989 "Chemistry of Carbon Compounds", vols. 1-5 and supps, Elsevier Science Publishers, 1989; "Organic Reactions", vols 1-40, John Wiley and Sons, New York, N.Y., 1991; March 2001, "Advanced Organic Chemistry", 5th ed. John Wiley and Sons, New York, N.Y.; Larock 1990, "Comprehensive Organic Transformations: A Guide to Functional Group Preparations", $2^{nd}$ ed. VCH Publishers; and other references more specifically drawn to polymer chemistry. The methods described below are merely illustrative of some methods by which the polyal conjugates of this invention can be synthesized, and various modifications to these methods can be made and will be suggested to a person of ordinary skill in the art having regard to this disclosure.

The starting materials, intermediates, and conjugates of this invention may be isolated and purified using conventional techniques, including filtration, distillation, crystallization, chromatography, and the like. They may be characterized using conventional methods, including physical constants and spectral data.

Materials

Bovine pancreatic trypsin (EC 3.4.21.4) Type III, chymotrypsin, Nα-benzoyl-L-arginine ethyl ester (BAEE), acetyltyrosine ethyl ester (ATEE), dextran B-512 (Mn 188,000 Da) were obtained from Sigma Chemical Company (St Louis, Mo.). Sodium borohydride, sodium cyanoborohydride, sodium metaperiodate, 1-[3-(dimethylamino)propyl-3-ethyl-carbodiimide hydrochloride (EDC), diethylenetriaminepentacetic acid (DTPA), 4-dimethylaminopyridine (DMAP) and succinic anhydride were from Aldrich, St Louis, Mo. InCl$_3$ [In-111] was from Perkin Elmer Life Sciences (Boston, Mass.). Anhydrous pyridine, ethyl alcohol, and other solvents were obtained from Sigma-Aldrich and used without further purification.

Equipment and Methods

Size exclusion chromatography in aqueous media was carried out using Varian-Prostar HPLC system equipped with BIO-RAD model 1755 Refractive Index detector and LDC/Milton Roy SpectoMonitor 3000 UV detector. HPSEC columns, Biosil SEC-125 and Biosil SEC-400 (BIO-RAD), and low pressure Superose-6 column (Pharmacia), were used for studying MW/MWD of polymers and polymer-protein conjugates. SEC column calibration was performed using protein standards and broad molecular weight dextran standards. Unless otherwise stated, elution was performed isocratically in 50 mM pH=7.0 phosphate buffer with 0.9% NaCl. $^1$H and $^{13}$C NMR were carried out on Varian Mercury-300, Bruker DPX-300, and Bruker Aspect 3000 NMR spectrometers using solvent peak as reference standard. Cary 300Bio UV/visible spectrophotometer equipped with Peltier-thermostated multi-cell block was used for spectroscopic measurements and enzyme kinetics studies. Radioactivity measurements were carried out using Wallac Wizard 1480 gamma counter (Perkin Elmer). Gamma scintigraphy was performed using Ohio Nuclear gamma camera with medium energy collimator.

Example 1

Exemplary Synthesis of Bifunctional Compounds of the Invention (Scheme 1)

General Methods. $^1$H NMR spectra were recorded with a Varian XL-500 spectrometer. Chemical shifts are expressed in parts per million (ppm) on the δ scale relative to a TMS internal reference standard. In general, CDCl$_3$ was used for the free bases and DMSO-d$_6$ was used for salts. Coupling constants (J values) were given in Hz. Thin layer chromatography (TLC) was performed on 250 µm thickness silica gel plates or alumina precoated plates (Whatman, AL SIL G/UV or J. T. Baker, Baker-flex, SILICA GEL IB-F) containing fluorescent indicator (2×8 cm). Column chromatography was performed on silica gel (Baker, 40 µm Flash chromatography). Fractions were analyzed using TLC and compounds were visualized using ninhydrin (0.5 g in 100 mL of methanol) for primary and secondary amine(s), ultraviolet light and/or iodine vapor.

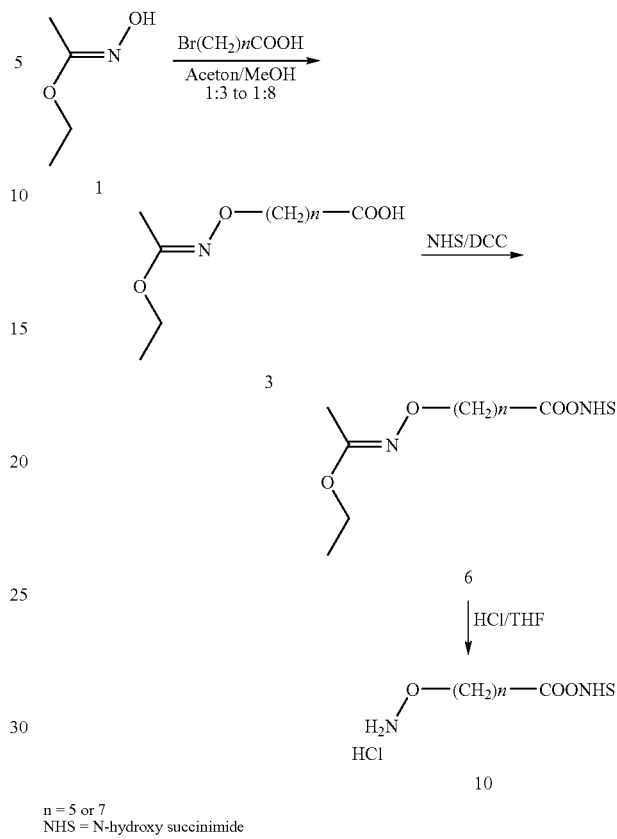

Scheme 1 n = 5 or 7
NHS = N-hydroxy succinimide

8-[1-Ethoxyethylideneaminooxy]octanoic acid 2,5-dioxo-pyrrolidin-1-yl ester (6). To a mixture of ethyl N-hydroxy-acetimidate 1 (6.2 g, 60 mmol) and 8-bromooctanoic acid (15 g, 67 mmol) in 150 mL of solvent mixture (methanol 8: acetone 1) was added drop wise 22 mL of 10N NaOH and heated at 50° C. for 12 h. The reaction mixture was cooled, the organic solvent was removed by rotary evaporation. The dilute HCl solution was added to adjust pH down to 6. The resulting turbid mixture was extracted with CHCl$_3$ and EtOAc. The extract was washed with brine, dried, filtered, and solvent was evaporated to crude oil (3, 12 g, 49 mmol, 82%). A mixture of 3 (12 g, 49 mmol) and N-hydroxysuccinimide (5 g, 50 mmol) in 100 mL of THF was treated with 50 mL of DCC (1.0 M solution in CH$_2$Cl$_2$). The solids were filtered, and the clear filtrate was evaporated. The resultant brown oil was purified on a silica gel column. Elution with 20% ethyl acetate/hexane afforded 5.8 g (17 mmol, 34%) of the product as a wet solid. $^1$H NMR (DMSO-d$_6$): δ 1.21 (3H, t, J=7.0), 1.28-1.38 (6H, m), 1.57 (2H, p, J=6.8), 1.64 (2H, p, J=7.4), 1.86 (3H, s), 2.65 (2H, t, J=7.5), 2.81 (4H, s), 3.82 (2H, t, J=6.5), 3.94 (2H, q, J=7.0)

8-Aminooxy-octanoic acid 2,5-dioxo-pyrrolidin-1-yl ester HCl salt (10). To a solution of 6 (5.8 g, 17 mmol) in THF (30 mL) was added a mixture of HCl and THF (4 mL, 2 mL of c.HCl and 2 mL of THF. The reaction mixture was stirred for 4 h, concentrated to a wet solid and washed with 5% EtOAc/hexane. The product solidified (hygroscopic) under vacuum was used without further purification. $^1$H NMR (DMSO-d$_6$): δ 1.28-1.37 (6H, m), 1.57-1.65 (4H, m), 2.65 (2H, t, J=7.3), 2.82 (4H, s), 4.02 (2H, t, J=6.3), 11.09 (3H, br s).

Example 2

Synthesis of Maleimidyl Bifunctional Linkers for Polymer Conjugates

Using the same protecting group, aminooxy alkyl maleimide was synthesized as shown in Scheme 2.

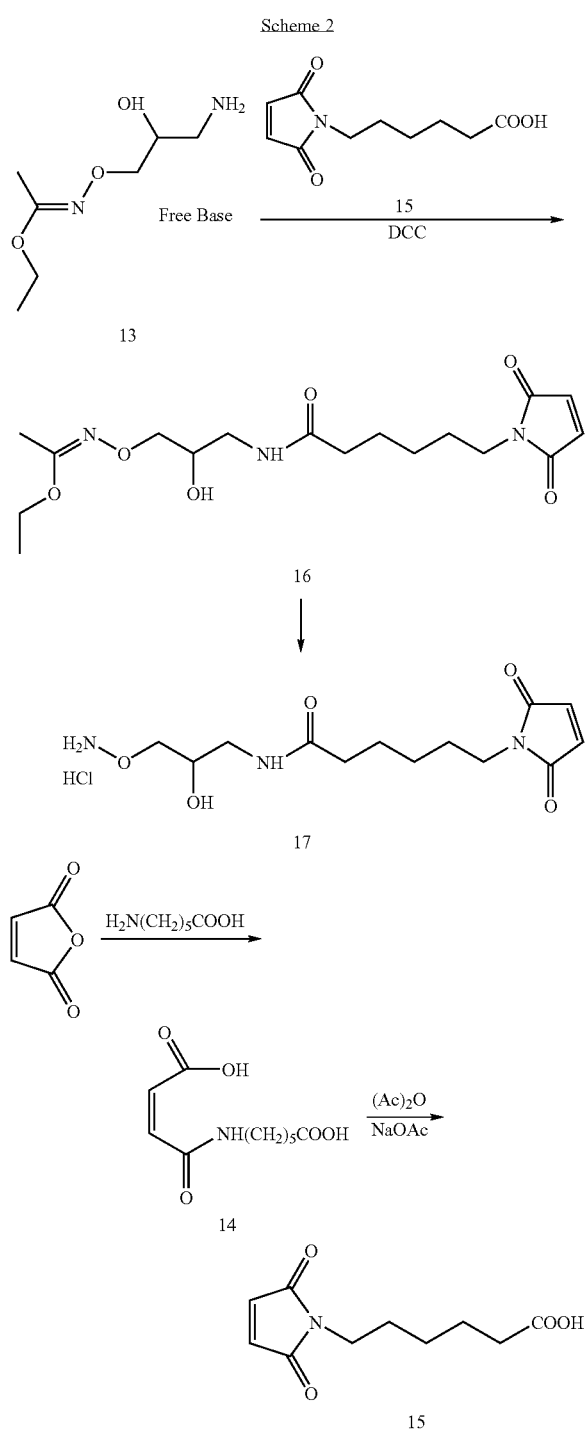

3-[5-Carboxypentylcarbamoyl]acrylic acid (14). 6-Aminocaproic acid (10.1 g, 81.6 mmol) was added to maleic anhydride (8.09 g, 82.6 mmol), in 100 mL of anhydrous DMF. The mixture was stirred at room temperature for 24 h and poured into 250 mL of water. White precipitate was filtered, washed with ether and dried (15 g, 86%). $^1$H NMR (DMSO-$d_6$): δ 1.27-1.33 (2H, m), 1.45-1.54 (4H, m), 2.21 (2H, t, J=7.3), 3.18 (2H, q, J=6.7), 6.24 (1H, d, J=13.0), 6.42 (1H, d, J=12.5), 9.11 (1H, br s), 13.6 (1H, br).

6-[2,5-Dioxo-2,5-dihydro-pyrrol-1-yl]hexanoic acid (15). The acid 14 (4.5 g, 21 mmol) was refluxed in 60 mL of $(Ac)_2O$ with NaOAc (1.72 g, 21 mmol) for 3 h. After cooling, the reaction mixture was concentrated. The residue was dissolved in EtOAc, washed with brine, dried over $MgSO_4$, filtered and evaporated to give a deep red oil that was purified by silica gel column chromatography ($CHCl_3$:MeOH/99:1). The maleimide product 15 was isolated as a white solid (1.4 g, 32%). $^1$H NMR (DMSO-$d_6$): δ 1.18-1.24 (2H, m), 1.45-1.52 (4H, m), 2.18 (2H, t, J=7.5), 3.38 (2H, t, J=7.0), 7.01 (2H, s).

N-{3-[6-[2,5-Dioxo-2,5-dihydro-pyrrol-1-yl]-hexanoylamino]-2-hydroxy-propyl}-acetimidic acid ethyl ester (16). The amine 13 (1.6 g, 10 mmol), in 30 mL of anhydrous THF was added dropwise to a solution of 10 mL of DCC (10 mmol, 1M solution of DCC in $CH_2Cl_2$) and acid 15 (2.1 g, 10 mmol). The mixture was stirred at room temperature for 24 h. The reaction mixture was concentrated. The residue was dissolved in EtOAc, washed with brine, dried over $MgSO_4$, filtered and evaporated to give a colorless oil that was purified by silica gel column chromatography ($CHCl_3$:MeOH/99:1). The amide product 16 was isolated as a wet solid (1.5 g, 42%). $^1$H NMR ($CDCl_3$): δ 1.27 (3H, t, J=7.3), 1.30-1.35 (2H, m), 1.60 (2H, p, J=7.3), 1.67 (2H, p, J=7.8), 1.94 (3H, s), 2.20 (2H, t, J=7.5), 3.20-3.25 (1H, m), 3.51 (2H, t, J=7.3), 3.48-3.55 (1H, m), 3.87 (1H, dd, J=6.3, 11.8), 3.92-4.01 (5H, m), 4.04 (1H, br s), 6.34 (1H, t, J=5.5), 6.71 (2H, s).

6-[2,5-Dioxo-2,5-dihydro-pyrrol-1-yl]-hexanoic acid [3-aminooxy-2-hydroxy-propyl]-amide HCl salt (17) was prepared as described for 10 to give the title compound 17 as a white solid.

REFERENCES (1) Stanek et. al. *J. Med. Chem.* 1992, 35, 1339-1344.
(2) Buehler et. Al. *J. Am. Chem. Soc.* 1967, 89, 261-265

Example 3

Biodegradable Hydrophilic Polyals for Protein Modification

As discussed above, biodegradation of macromolecular therapeutics is an important but incompletely studied issue, even for most widely used polymers. For example, there is a potential risk that extended clinical use of conjugates containing non- or slow-biodegradable polymer fragments can lead to long-term cell vacuolization (see, for example, Bendele A. Seely J. Richey C. Sennello G. Shopp G. (1998) Short communication: renal tubular vacuolation in animals treated with polyethylene-glycol-conjugated proteins. *Toxicological Sciences*. 42, 152-7) and overload, development of lysosomal disease syndrome (see, for example, Christensen, M., Johansen, P., Hau C., (1978) Storage of polyvinylpirrollidone (PVP) in tissue following long-term treatment with a PVP-containing Vasopressin preparation. *Acta Med Scand.*, 204, 295-298), and, at higher doses, to other pathological metabolic alterations (see, for example, Miyasaki K. (1975) Experimental Polymer Storage Disease in Rabbits. *Virchows Arch. A. Path. Anat. And Histol.*, 365, 351-365). The predominant clearance route of relatively large (>10-15 nm) long circulating conjugates, regardless of the size of the polymer component, is through uptake by cells (mostly in RES, but also in other tissues) followed by intracellular degradation and metabolization. Reducing the molecular weight of the polymer component, e.g. to 30-40 kDa, which is an effective strategy for enabling renal clearance of small molecule drug conjugates (see, for example, Duncan, R., Gac-Breton, S., Keane, R., Musila, R., Sat, Y. N., Satchi, R., Searle, F. (2001) Polymer-drug conjugates, PDEPT and PELT: basic principles for design and transfer from laboratory to clinic, *J. Controlled Release*, 74, 135-146), is not a feasible solution for protein conjugates or other large (>5-7 nm) constructs. Conjugates degrading upon cell uptake with release of smaller but still non-biodegradable fragments, such as PEG telomers with degradable linkages between PEG blocks (See, for example, Tomlinson R, Klee M, Garrett S, Heller J, Duncan R and Brocchini S. (2002) Pendent Chain Functionalized Polyacetals That Display pH-Dependent Degradation: A Platform for the Development of Novel Polymer Therapeutics, *Macromolecules*, 35, 473-480), would most unlikely not solve the problem because no efficient cellular mechanisms transporting such fragments back to the extracellular space have been identified. Development of essentially completely biodegradable polymers, preferably degrading with formation of low-toxicity, readily clearable or metabolizable products, appear to be the predominant possible radical solution of the problem of long-term intracellular deposition. The type of protein-polymer linkage and the degree of polymer modification can also alter both conjugate degradability and biological properties (see, for example, Danauser-Reidl, S., Hausmann, E., Schinck, H., Bender, R., Dietzfilbinger, H., Rastetter, J., Hanauske, A. (1993) Phase-I clinical and pharmacokinetic trial of Dextran conjugated Doxorubicin (AD-70, DOX-OXD). *Invest. New Drugs*, 11, 187-195). This necessitates the selection of a polymer backbone structure and conjugation strategies that would not interfere, or minimally interfere, with biological functions of the protein component, nor (where applicable) adversely alter protein properties upon release from the conjugate. A combination of a macromolecular material and a cross-linking reagent enabling sufficient conjugate stability in the normal extracellular environment and, on the other hand, acceptable rate of conjugate disintegration upon endocytosis, would be most beneficial.

Hydrophilic essentially fully degradable polyals, e.g., poly [1-hydroxymethylethylene hydroxymethyl-formal] (PHF), have been developed and reported as acyclic mimetics of polysaccharides (see, for example, (1) Papisov M I, Garrido L, Poss K, Wright C, Weissleder R, Brady T J. (1996) A long-circulating polymer with hydrolizable main chain. 23-rd *International Symposium on Controlled Release of Bioactive Materials*, Kyoto, Japan, 1996; Controlled Release Society, Deerfield, Ill.; 107-108; and (2) Papisov M. I. (1998) Theoretical considerations of RES-avoiding liposomes. *Adv. Drug Delivery Rev.*, 32, 119-138). These materials, which can be prepared synthetically and by lateral cleavage of some polysaccharides, were shown to be essentially (i) non-bioreactive, (ii) non-toxic and (iii) fully degradable, and, thus, proved to have potential in various pharmaceutical applications (see, for example, (1) Papisov M I, Babich J W, Dotto P, Barzana M, Hillier S, Graham-Coco W, Fischman A J. (1998) Model cooperative (multivalent) vectors for drug targeting. *25th Int. Symp. on Controlled Release of Bioactive Materials*, 1998, Las Vegas, Nev., USA; Controlled Release Society, Deerfield, Ill., 170-171; and (2) Papisov M I. (2001) Acyclic polyacetals from polysaccharides. (Biopolymers from polysaccharides and agroproteins), *ACS Symposium Series* 786, pp. 301-314). Polyals contain pH-sensitive acetal or ketal groups within the main chain, which provides the desired combination of polymer stability in neutral and alkaline media and destabilization in acidic environment.

In certain embodiments, the present invention further expands the scope of potential applications for hydrophilic polyals, and demonstrates suitability of these materials for preparation of essentially fully degradable protein conjugates with preservation of protein functionality. In certain exemplary embodiments, a hydrophilic polyal (PHF) is used to obtain and characterize conjugates of well-known model proteases, trypsin and α-chymotrypsin. Conjugation techniques include the use of new bifunctional coupling reagents containing an aminooxy (O-hydroxylamino) group; these reagents were also developed in our laboratory and specifically tailored for conjugations involving aldehyde-bearing molecular modules in aqueous media. The main model protein of this study, trypsin, was selected as a relatively small protein with readily measurable activity and fast blood clearance. Trypsin was also well characterized in immobilization reactions involving various soluble and solid carriers and conjugation techniques.

Experimental Section

Materials

Bovine pancreatic trypsin (EC 3.4.21.4) Type III, chymotrypsin, N□-benzoyl-L-arginine ethyl ester (BAEE), acetyl-tyrosine ethyl ester (ATEE), dextran B-512 (Mn 188,000 Da) were obtained from Sigma Chemical Company (St Louis, Mo.). Sodium borohydride, sodium cyanoborohydride, sodium metaperiodate, 1-[3-(dimethylamino)propyl-3-ethyl-carbodiimide hydrochloride (EDC), diethylenetriaminepentacetic acid (DTPA), 4-dimethylaminopyridine (DMAP) and succinic anhydride were from Aldrich, St Louis, Mo. $InCl_3$ [In-111] was from Perkin Elmer Life Sciences (Boston, Mass.). Anhydrous pyridine, ethyl alcohol, and other solvents were obtained from Sigma-Aldrich and used without further purification.

Equipment and Methods

Size exclusion chromatography in aqueous media was carried out using Varian-Prostar HPLC system equipped with BIO-RAD model 1755 Refractive Index detector and LDC/Milton Roy SpectoMonitor 3000 UV detector. HPSEC columns, Biosil SEC-125 and Biosil SEC-400 (BIO-RAD), and low pressure Superose-6 column (Pharmacia), were used for studying MW/MWD of polymers and polymer-protein conjugates. SEC column calibration was performed using protein standards and broad molecular weight dextran standards. Unless otherwise stated, elution was performed isocratically in 50 mM pH=7.0 phosphate buffer with 0.9% NaCl. $^1$H and $^{13}$C NMR were carried out on Varian Mercury-300, Bruker DPX-300, and Bruker Aspect 3000 NMR spectrometers using solvent peak as reference standard. Cary 300Bio UV/visible spectrophotometer equipped with Peltier-thermostated multi-cell block was used for spectroscopic measurements and enzyme kinetics studies. Radioactivity measurements were carried out using Wallac Wizard 1480 gamma counter (Perkin Elmer). Gamma scintigraphy was performed using Ohio Nuclear gamma camera with medium energy collimator.

Polymer Synthesis

PHF is a semi-synthetic acyclic polyacetal which can be prepared via lateral cleavage of Dextran B-512 with periodate. Dextran B512, a product of *Leuconostoc Mesenteroides* strain B-512, is a nearly linear (1->6)-poly-α-D-glucose with ca. 5% (1→3; β) branching, of which 95% are only one or two residues long (see, for example, Jeanes A. (1986) Immunochemical and related interactions with dextrans reviewed in terms of improved structural information. *Molecular*

*Immunology* 23, 999-1028). Periodate oxidation of (1->6)-polyglycoside in controlled conditions starts with breaking up ether C2-C3 or C3-C4 bond, resulting in the formation of dialdehydes IIa and IIb (see, for example, Ishak M. F., Painter T. J., (1978) Kinetic evidence for hemiacetal formation during the oxidation of dextran in aqueous periodate. *Carbohyd. Res.*, 64, 189-97). The slower oxidation stage, cleavage of C3, leads to dialdehyde III (Scheme 3).

The Dextran solution was treated with 47.95 g (224.2 mmol) of metaperiodate dissolved in 350 ml of deionized water at 0-5° C. in a light protected reactor for 3 hours. The precipitated sodium iodate was removed by filtering the reaction mixture through 1μ glass filter. The pH of the filtrate was adjusted to 8.0 with 5N NaOH, and the resultant solution was treated with sodium borohydride (7.4 g, 200 mmol, dissolved in 100 ml of deionized water) for 2 hours. Then, the pH of the

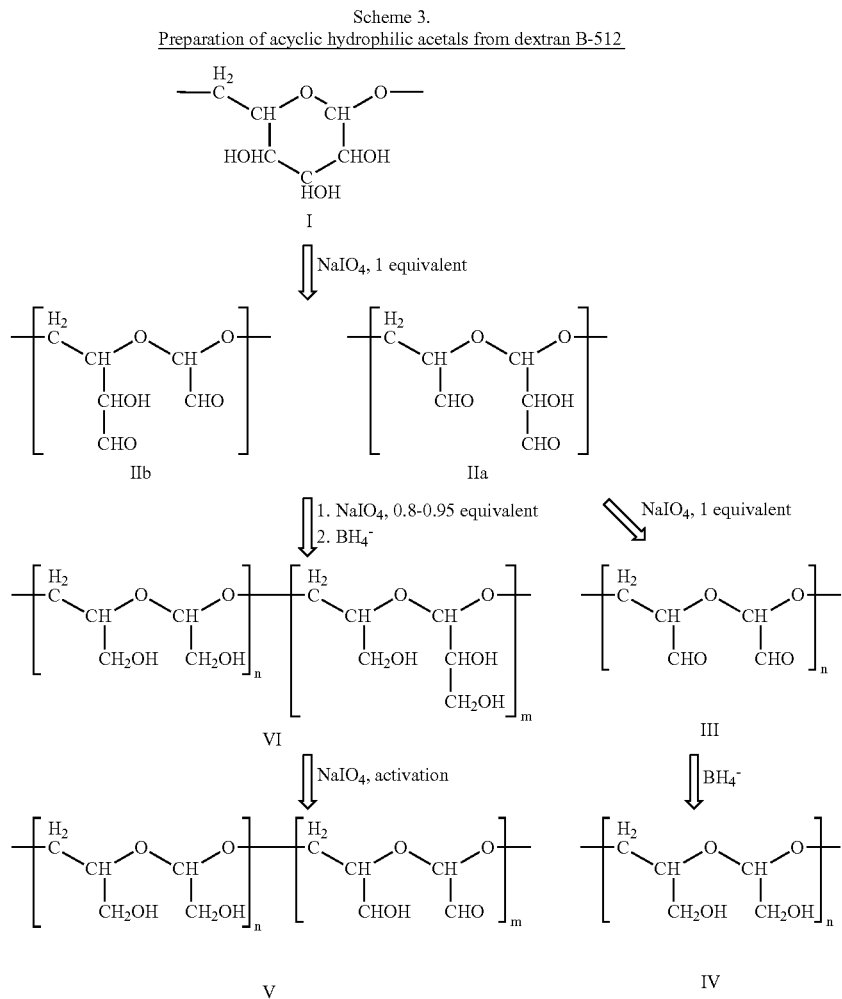

Borohydride reduction of aldehyde groups of dialdehydes IIa, IIb and III gives polyals with pendant hydroxymethyl groups IV and (from IIa and IIb) vicinal glycol groups V. Accurate control of oxidizer/substrate stoichiometry and reaction conditions enables generation of polymers with a desirable amount of vicinal diol, which can be subsequently used as selective reactive sites for further polymer modification and conjugation. In certain embodiments, both PHF and PHF-diols with vicinal diol content ranging from 2 to 20% (mol) were prepared and used as protein carriers. In most cases, dextran with number average molecular weight (Mn) of 188 kDa was used as starting material.

Poly-1-hydroxymethylethylene hydroxymethyl-formal, IV (PHF). In certain embodiments, PHF was prepared via exhaustive lateral cleavage of carbohydrate rings by periodate oxidation. Dextran of Mn 188,000 Da (15.15 g, 93.4 mmol of glycopyranoside) was dissolved in 300 ml of deionized water.

reaction medium was adjusted to approximately 6.5 with 1 N HCl. The obtained macromolecular product was purified and concentrated on CH2PR flow dialysis system (Amicon, Beverly, Mass.) equipped with hollow fiber cartridge, cutoff 30 kDa, by passing approximately 4 volumes of deionized water through the polymer solution. Alternatively, the product was purified on G-25 preparative column using deionized water as an eluent. PHF was recovered from aqueous solutions by lyophilization. Average polymer yields ranged from 70% to 80%. SEC analysis of a typical PHF prepared from Dextran 188 kDa showed peak molecular weight at 130,000 Da, Mn 92,000 Da, and polydispersity index (Mw/Mn) of 2.5. The structures of all obtained polymers, as examined by $^{13}$C and $^1$H NMR, were consistent with the expected acyclic polyacetal structure. The typical synthetic procedures for PHF and PHF-glycol preparation described below.

PHF-glycol. In certain embodiments, PHF-glycol was prepared by controlled dextran cleavage that was stopped at stage II. Polymers comprising vicinal diol structural units were obtained as a result of subsequent reduction from intermediates IIa and IIb. Glycol-substituted polymers were prepared as described above for PHF, except that the starting (glucopyranoside)/(periodate) molar ratio was 1.00 to 0.95. The presence of PHF-diol structure VI in the resultant polymer was confirmed by $^1$H NMR spectroscopy. Polymer spectrum registered in DMSO-$d_6$:$D_2O$ (95:5 v/v) has shown the specific for structure IV signal of C1-H at δ 4.62 (t, J=5.2 Hz) and the signal of C1 acetal hydrogen at δ 4.49 (d, J=5.2 Hz) characteristic for structure V. At the same time, no C4-H signals at δ 3.10-3.20 (m) were registered, indicating the absence of $C_3$-$C_4$ diols in reduced IIb. The amount of PHF-diol structures (V), as determined by NMR, was approximately 2%. SEC analysis has shown no substantial difference between MW/MWDs of the starting Dextran and the resultant PHF-glycol.

PHF succinate (PHF-SA). PHF (100 mg), succinic anhydride (7.5 mg, 0.075 mmol) and DMAP (1.2 mg, 0.01 mmol) were dissolved in 5 ml of anhydrous pyridine. After 18 hours of agitation at 40° C., pyridine was removed in vacuum. The residue was suspended in deionized water, and the pH was adjusted to 7.0 by addition of 1 N NaOH. The succinylated PHF was purified on a Sephadex G-25 column with deionized water an eluent, and recovered from aqueous solution via lyophilization. The succinic acid content, as determined by potentiometric titration, was 11.3%. The $^1$H NMR spectrum of the polymer ($D_2O$) contained signals of characteristic methylene protons of succinic acid ester at δ 2.62 (t) and δ 2.46 (t).

Protein Conjugates

In certain embodiments, Protein conjugates with PHF-SA were prepared via EDC mediated coupling reaction PHF-SA with model proteins.

PHF-diol conjugates were prepared by conventional reductive amination (see, for example, Dottavio-Martin, D. and Ravel, J. M., (1978) Radiolabeling of proteins by reductive alkylation with [14C]-formaldehyde and sodium cyanoborohydride. *Analyt. Biochem.*, 87, 562) of polymeric aldehydes generated from vicinal glycol groups present in PHF-diol, as well as by non-reductive amination utilizing the aminooxy (O-hydroxylamino)-containing bifunctional agents of the invention.

Two types of aminooxy-reagents were developed (see examples 1 and 2 above) and tested, containing a protected aminooxy-group and either a maleimide group for thiol modification (N-(5-(2,5-dioxo-2,5-dihydro-pyrrol-1-yl)-5-oxohexenyloxy)-acetimidic acid ethyl ester, VII), or N-hydroxysuccinimide ester group for aminogroup modification (N-(3-(3-(2,5-dioxo-pyrrol-1-yl)-propionylamino)-2-hydroxypropoxy)-acetimidic acid ethyl ether, VIII). Non-reductive coupling of the aminooxy coupling reagents, or their unprotected analogs, with carbonyl containing compounds was conducted at pH 3-4, which enabled preservation of N-oxysuccinimido- and maleimido-functions for the subsequent stage of protein coupling. Representative procedures illustrating the process of PHF conjugation are given below for trypsin.

PHF-trypsin conjugates (reductive amination). The solution of PHF-diol with Mn 150 kDa (200 mg) and diol content 10% (mol/mol monomer) was dissolved in 2 ml of deionized water and combined on ice with 30.1 mg (0.14 mmol) of $NaIO_4$ in 0.25 ml of deionized water. After a 1 hour incubation, the activated polymer was combined with 31.8 mg of trypsin in 6.0 ml of 0.1 M phosphate buffer pH 5.5 and 18 mg (0.29 mmol) sodium cyanoborohydride, incubated on ice for 1 hour, then at 8° C. for 18 hours. The macromolecular product was recovered by gel filtration on Sephadex G25 column equilibrated with deionized water, and separated from unreacted trypsin on Superose-6 column. Trypsin conversion was 61% (HPSEC BioSil-125, detected by UV at 280 m).

PHF-SA-trypsin conjugates. PHF-SA solution with Mn=176 kDa, 100 mg in 2.0 ml of deionized water, was combined with 3.0 ml of 5.0 mg/ml trypsin solution in 0.1M phosphate buffer, pH 7.4. Then, EDC (20 mg) was added to the reaction mixture in 500 µl of cold (0-5° C.) deionized water. Trypsin conversion after 3 hours of incubation, according to HPLC (UV at 280 nm), was 97%. The reaction mixture was separated from low molecular weight components and concentrated to approximately 10 mg/ml on PM-30 ultrafiltration membrane using 0.05 M PBS pH 7.0. The conjugate was separated from residual unbound trypsin on Superose-6 column with 0.5M PBS, pH 7.0, as a running buffer. The resultant conjugate was aliquoted and stored frozen at −40° C. SEC analysis of this conjugate gave Mn=245 kDa, PI=1.8, and peak polymer MW=260 kDa. Trypsin conjugate content estimated by HPLC and spectroscopically at 280 nm was 10.7% w/w.

PHF-AO(NHS)-trypsin conjugates. The solution of PHF-diol with Mn ~150 kDa (200 mg) and diol content 2% (mol/mol monomer) was dissolved in 2 ml of deionized water and combined on ice with 15 mg (0.07 mmol) of $NaIO_4$ in 0.125 ml deionized water. After a 1 hour incubation, the polymer product was purified by gel filtration on Sephadex G-25, using deionized water as an eluent. The resulting solution was diluted with 3.0 ml of ethyl alcohol and combined with 92.6 mg of VIII. in 2 ml of ethanol. The pH of the mixture was adjusted to 3.0 by addition of 1M $NaHSO_4$, and agitated for 2 hours on ice. The pH was adjusted to approximately 7.0, and the product was purified on a Sephadex G-25 column equilibrated with deionized water. The resulting product was combined with 32 mg of trypsin dissolved in phosphate buffer pH 8.6, and the mixture was incubated on ice for 3 hours. HPSEC (UV at 280 nm) analysis of the reaction mixture showed 98% trypsin bonding to the polymer. The reaction mixture was desalted and concentrated to approximately 10 mg/ml on PM-30 ultrafiltration membrane using 0.05 M PBS pH 7.0. The conjugate was separated of residual unbound trypsin on Superose-6 column (Pharmacia) with 0.5M PBS pH 7.0 as a running buffer. The resultant conjugate was aliquoted and stored frozen at −40° C.

PHF-AO(MI)-trypsin conjugates. PHF-aldehyde was prepared as described above from PHF diol, Mn ~150 kDa. The PHF diol, 100 mg in 5.0 ml of deionized water, was combined with 46 mg of VII. The pH of the mixture was adjusted to 3.0 by addition of 1M $NaHSO_4$ and agitated for 2 hours on ice. Then, the pH was adjusted to 6.5, and the polymer was desalted on Sephadex G-25 column equilibrated with deionized water. The obtained product was combined with 16 mg of trypsin dissolved in phosphate buffer, pH 8.6, and incubated for 2 hours on ice and for 18 hours at 8° C. HPSEC (UV at 280 nm) analysis of the reaction mixture showed 75% trypsin bonding to polymer carrier. The reaction mixture was desalted and concentrated to approximately 10 mg/ml on a PM-30 ultrafiltration membrane, using 0.05 M PBS, pH 7.0. The conjugate was separated from the residual unbound trypsin on Superose-6 column with 0.5M PBS, pH 7.0, as a running buffer, the desalted on Sephadex G-25 column equilibrated with deionized water, and lyophilized. SEC analysis of this conjugate (Biosil 400) showed substantial presence of a high molecular weight fraction eluted with void volume. Peak MW ~500 kDa.

Trypsin Conjugate Modification with DTPA and [111]In Labeling.

For animal studies, protein conjugates were labeled with $^{111}$In after modification of the trypsin portion of conjugates with DTPA. EDC mediated coupling was carried out in aqueous solution at DTPA/EDC/Trypsin lysine residue ratio 500: 50:1 at pH 7.5. The resultant DTPA-labeled conjugates were purified by gel chromatography on Sephadex G-25. DTPA to protein molar ratio, as determined by Cu(II) colorimetric assay at 775 nm was approximately 1:4. Unmodified proteins were labeled analogously.

Labeling was performed by transchelation from $^{111}$In citrate. The labeling solution was prepared by mixing carrier-free $^{111}$In indium chloride in 0.05 M HCl with a 20-fold volume excess of 0.5 M sodium citrate, pH=5.6. The resultant $^{111}$In indium citrate solution was added to unbuffered solutions of DTP-modified polymers at 0.2 to 1 mCi of $^{111}$In per 1 mg of dry substance. The labeled conjugates were separated by gel chromatography on Sephadex G-25, with simultaneous media replacement to sterile isotonic saline. Labeling efficacy after transchelation, as estimated by HPLC equipped with gamma detector, on average exceeded 90%. Radiochemical purity after desalting was >99%.

Blood Clearance and Biodistribution Study

Animal experiments were performed in accordance with institutional guidelines. Adult male CD1 mice (weight in a range 28 g to 34 g, Charles River Laboratories, Wilmington, Mass.) were injected with labeled conjugates and unmodified proteins via the tail vein (150 μL per injection, containing approximately 10 μCi of $^{111}$In).

Mice were euthanized at 0.25, 0.5, 1, 2, 4, and 8 hours (n=2). Blood samples and harvested organs (hart, lungs, liver, spleen, kidneys, adrenal glands, stomach, GI, testes, muscle, bone, brain and tail) were analyzed on gamma counter. The amount of radioactivity per organ was expressed as a percentage of the injected dose per gram tissue. For the PHF-AO-Trypsin (2:1) conjugate, blood clearance data were adjusted for unbound trypsin content (15% mol) using unmodified trypsin clearance profile for background correction.

Enzyme Activity

Esterase activity of model enzymes was measured with BAEE (trypsin), ATEE (α-chymotrypsin), and BSA as substrates at pH 7.4, following published techniques (see, for example, Foucault, G., Seydoux, F., Yon, J. (1974) Comparative kinetic properties of alpha, beta and psi form of trypsin. *Eur. J. Biochem.* 47, 295-302).

Hydrolytic Stability of Conjugates

Hydrolytic degradation of PHF and PHF-trypsin conjugates was studied at 37° C. in PBS at pH 7.4 and 5.5. The pH of the media remained constant over the course of the experiment. HPSEC analysis (Biosil 400) of the reaction mixture aliquots taken at 24, 72 and 144 hours was carried out to monitor the MW/MWD and composition of degradation products. The content of unbound and PHF-associated trypsin were estimated by monitoring absorbance at 280 nm.

PHF Conjugation with Proteins.

In certain embodiments, model proteins, trypsin and α-chymotrypsin, were used as models for development and characterization of protein-polyal conjugates. Conjugates were prepared utilizing three different crosslinking approaches.

The first approach was based on acylation of primary alcohol functionality present in PHF with succinic anhydride. Protein conjugation was subsequently conducted via by carbodiimide mediated coupling of the carboxy-modified polymer with the model protein (the method is targeted to coupling through, predominantly, lysine moieties). In the conditions used, approximately four of eight lysine moieties per trypsin and 14 moieties per chymotrypsin molecule were expected to be reactive. This approach was found to be productive, giving up to 95-98% protein conjugation and 90-95% preservation of protein activity in the conjugates.

Another conjugation technique used herein was based on activation of pendant glycol groups introduced into PHF structure via reduction of the intermediate oxidation products IIa/IIb (Scheme 3). Diols are readily transformed into active aldehyde groups immediately prior to conjugation. In one example, PHF-diol polyal protein conjugate was prepared by conventional method of reductive amination of polymeric aldehydes (conjugate 1, Table 1). Protein conversion, even at high aldehyde content in the polymer, was relatively low (~60%).

TABLE 1

Composition and MW/MWD of PHF-protein conjugates

| # | Carrier | Crosslinker | Enzyme | Enzyme to PHF ratio (mol) | Protein conversion, % |
|---|---------|-------------|--------|---------------------------|-----------------------|
| 1 | PHF-diol | Direct amination | Trypsin | 1 | 61 |
| 2 | PHF | SA | Trypsin | 1 | 97 |
| 3 | PHF-diol | AO-NHS (VIII) | Trypsin | 1 | 98 |
| 4 | PHF-diol | AO-NHS (VIII) | Trypsin | 2 | 85 |
| 5 | PHF-diol | AO-NHS (VIII) | Trypsin | 4 | 72 |
| 6 | PHF-AO-NHS* | N/a | Trypsin | 1 | 87 |
| 7 | PHF-diol | AO-MI (VII) | Trypsin | 1 | 75 |
| 8 | PHF-diol | SA | Chymotrypsin | 1 | 95 |
| 9 | PHF-diol | AO | Chymotrypsin | 1 | 93 |

*PHF-glycol with 2,3-diol content 2% was modified with VIII. Isolated and lyophilized PHF-AO-NHS was used sequentially for preparation of protein conjugate in one step without additional activation.

Alternatively, conjugates 2-7 and 9 were prepared utilizing the inventive aminooxy-group containing bifunctional reagents VII and VIII developed for conjugation of carbonyl containing compounds with molecules containing amino and sulfhydryl groups, respectively (Scheme 4).

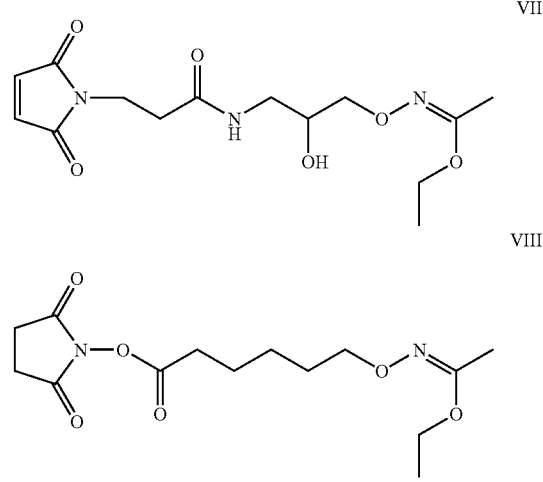

The method was developed as a replacement for the widely used non-reductive coupling of aldehydes and hydrazones. Amination with aminooxy-reagents requires milder conditions, e.g., at pH as high as 6 if necessary, and results in a more stable oxime bond (the stability of hydrazone conjugates are Scheme 4. Conjugation of Proteins with PHF Using Aminooxy-NHS and Aminooxy-Maleimide Crosslinkers.

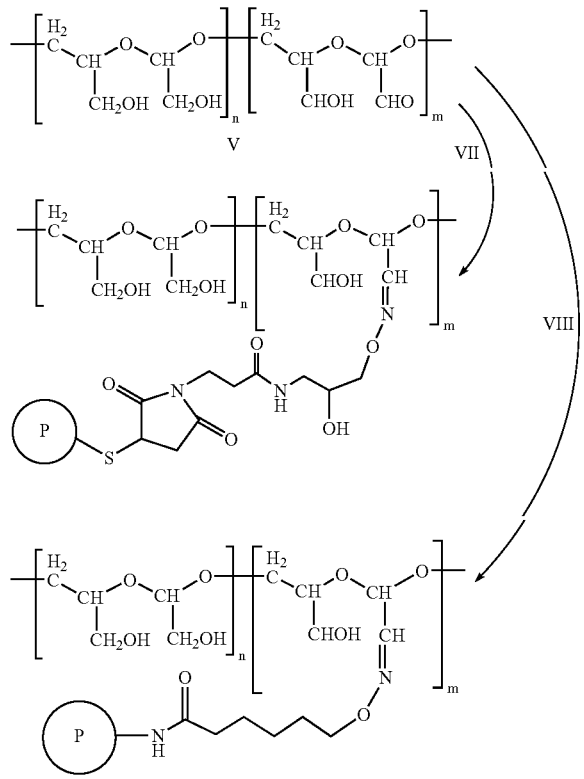

Application of aminooxy compounds for fast, one-step coupling through carbonyl groups (ketones, aldehydes) with formation of oxime bonds is widely used in medicinal chemistry and, in bioconjugate chemistry, was described, for example, for coupling glycosylated proteins with amino (see, for example, Berninger, R. W. Aminooxy-containing linker compounds and their application in conjugates. PCT WO 96/40662) and sulfhydryl group containing ligands (see, for example, Webb, R. R., II, and Kancko, E. (1990) Synthesis of 1-(aminooxy)-4-[(3-nitro-2-pyridyl)dithio]butane hydrochloride and of 1-(aminooxy)-4-[(3-nitro-2-pyridyl)dithio] but-2-ene. Novel heterofunctional cross-linking reagents, *Bioconjugate chem.*, 1, 96). The bifunctional reagents of the invention contain a free or protected aminooxy-group and either a thiol reactive maleimide group (VII) or an amino reactive N-hydroxysuccinimide ester group (VIII). Non-reductive coupling of these aminooxy coupling reagents with aldehydes was conducted in water at pH 3 for 2 hours. When unprotected analogs of VII and VIII or their hydrochloride salts were used, the pH of the reaction mixture during the coupling was maintained in the range of 3.5-4.5. Mild acidic conditions in both cases enabled preservation of N-oxysuccinimido- and maleimido-functions for the subsequent stage of protein coupling. Glycol content in PHF-diol as low as 2% mol. (or approximately 20 diol moieties per PHF molecule of MW=150 kDa) was sufficient to achieve quantitative coupling of proteins at PHF to protein 1:1 mol/mol.

Conjugates with molar protein to polymer ratio in the range from 1:1 to 4:1 were successfully prepared utilizing the above mentioned strategies; in most cases, the desirable degree of modification was achieved with high yields (85-95%). Conjugates prepared in one step using aminooxy-NHS coupling reagent VIII and via EDC mediated coupling to PHF-SA gave the highest conjugate yields (up to 95-98% for 1:1 conjugates) with respect to protein precursor. Both aminooxy reagents have shown high degree of flexibility with respect to the conjugation sequence and conditions. Different activation conditions, and sufficient stability of aminooxy, NHS and maleimido coupling groups, allowed to change the reaction order at will, or, if required, to work with isolated and purified aminooxy containing proteins or polyal intermediates. HPSEC data indicated that, in spite of the acidic conditions at the polyal/aminooxy coupling step, protein adducts were obtained without substantial depolymerization of PHF backbone and with nearly theoretical yields.

Without wishing to be bound to any particular theory, we proposed that the observed conjugate MW (in many cases 1.5 to 2 times higher than expected) may be the result of partial crosslinking of polyal chains via protein modifier. This process, however, had no noticeable effects on enzymatic activity of conjugates.

Comparative evaluation of enzymatic activity was performed using conjugates with approximately 1:1 carrier/protein molar ratio (conjugates 2, 3, and 8, Table 1). No significant changes in the Michaelis-Menten parameters ($K_M$, $k_{kat}$) and no pH optimum shifts were observed, as compared to native enzymes. Conjugates retained from 85% to 95% of the native enzyme activity when tested with synthetic substrates. As expected, a somewhat more significant decrease in enzyme activity was observed using BSA as a substrate, most likely due to expected steric hindrance. Thus, the obtained data are in agreement with earlier literature data on trypsin conjugates, e.g., with partially oxidized sucrose polymers (see, for example, R. Vankatesh and P. V. Sundaram. (1998) Modulation of stability properties of bovine trypsin after in vitro structural changes with a variety of chemical modifiers. *Protein Engineering*, 11, 8, 691-698).

pH-Dependent Hydrolytic Degradation of PHF-protein conjugates.

All PHF and PHF-diol based conjugates exhibited a pH-dependent profile of hydrolytic degradation, being essentially stable at neutral and slightly basic pH (7.0-10.5).

Hydrolytic degradation of PHF and two different PHF-trypsin conjugates, PHF-SA-Trypsin (protein content 10%, Mn=250 kDa) and PHF-AO-Trypsin (protein content 25%, Mn 350 kDa), was studied at pH 7.4 and 5.5. Indeed, neither substantial changes in polymer MW/MWD nor noticeable accumulation of unbound trypsin were observed at 37° C. pH 7.4 over a 144-hour period. On the contrary, incubation of polyals at 37° C., pH 5.5, for the same time period, showed steady and slow decrease in Mn and broadening of molecular weight distribution for all three preparations, and protein release for both conjugates (see Table 2). The data on i) the rate of Mn decrease, ii) the amount of trypsin released, and iii) the percentage of polymer fraction recovery, suggests that the oxime linked conjugate (PHF-AO-Trypsin) has a higher degradation rate then PHF and the succinic acid cross-linked PHF conjugate (PHF-SA-Trypsin).

TABLE 2

Degradation of PHF and PHF-trypsin conjugates in PBS at pH 5.5

| Time, h | Mn | Peak MW | PI | Polymer recovery, % | Trypsin release, % |
|---|---|---|---|---|---|
| PHF | | | | | |
| 0 | 92,000 | 130,000 | 2.6 | 100.0 | n/a |
| 72 | 86,000 | 99,000 | 2.0 | 98.5 | " |
| 144 | 66,000 | 97,000 | 3.6 | 89.2 | " |
| PHF-AO-Trypsin (1:2) | | | | | |
| 0 | 344,000 | 429,000 | 2.5 | 100.0 | n/a |
| 72 | 270,000 | 363,000 | 2.8 | 96.1 | 5.4 |
| 144 | 174,000 | 255,000 | 4.6 | 89.8 | 10.5 |
| PHF-SA-Trypsin (1:1) | | | | | |
| 0 | 246,000 | 260,000 | 1.8 | 100.0 | n/a |
| 72 | 177,000 | 209,000 | 2.0 | 99.8 | 4.7 |
| 144 | 153,000 | 176,000 | 3.1 | 98.6 | 5.4 |

Biokinetics and biodistribution of [$^{111}$In] DTPA labeled model PHF-protein conjugates. Biokinetics of PHF-SA-Trypsin, PHF-AO-Trypsin (protein content 10% and 25%, and Mn 250=kDa and 350 kDa respectively) and unmodified trypsin (26 kDa) were studied to determine the effect of PHF modification on protein biokinetics and biodistribution. The data showed significant improvements in blood half-life of PHF modified trypsin, as compared to the unmodified protein (FIG. 1).

The unmodified radiolabeled trypsin preparation showed clearance of 80% of activity from blood within 15 minutes after administration (initial blood half life ca. 7 min), followed by an apparently monoexponential clearance with 4±0.8 hour half-life. Considering the relatively small protein size and the character of final biodistribution, the first (main) phase is consistent with renal clearance and extravasation. The secondary phase can be related to redistribution back from the tissues and prolong circulation of trypsin complexes with macromolecular protease inhibitors present in plasma.

Both PHF-Trypsin conjugates also showed a biphasic blood clearance pattern, although of a different character and length. After approximately 40% of activity was cleared from blood within 1 hour, the rest (main fraction) remained in circulation with a half-life time of 8 hours. Here, the first phase is consistent with extravasation (and, possibly, partial renal clearance) of the smaller fraction of the unfractionated conjugates, whereas the second phase is consistent with long circulation of the main fraction of the conjugate. Notably, the long circulation also indicates preservation of conjugate integrity within the timeframe of the experiment.

The final biodistribution data (Table 3) showed an up to one order of magnitude reduction in label accumulation in kidneys, and a significant reduction in hepatic accumulation for polyal conjugates versus unmodified trypsin. No notable increase of accumulation in spleen (which is sometimes observed for high molecular weight polymers and microparticles) was observed for PHF conjugates as compared to trypsin control.

Note that animals were not perfused, and therefore the higher label content in lung tissue (both PHF-AO- and PHF-SA-Trypsin) and hart (PHF-AO-Trypsin) is consistent with higher residual conjugate content in the blood pool of these organs.

TABLE 3

Biodistribution of radiolabeled conjugates at 8 hours following iv administration

| | Label accumulation, % dose/g tissue | | |
|---|---|---|---|
| Tissue | PHF-SA-Trypsin | PHF-AO-Trypsin | Trypsin |
| Blood | 7.4 | 13.0 | 2.2 |
| Hart | 1.1 | 2.8 | 0.8 |
| Lung | 4.2 | 6.6 | 2.4 |
| Liver | 5.3 | 5.0 | 7.9 |
| Spleen | 2.5 | 2.9 | 2.1 |
| Kidney | 3.1 | 7.7 | 35.8 |
| Adrenals | 1.2 | 2.5 | 1.3 |
| Stomach | 0.5 | 1.0 | 0.5 |
| GI | 0.7 | 1.0 | 0.8 |
| Testes | 0.4 | 0.6 | 0.8 |
| Muscle | 0.3 | 0.5 | 0.2 |
| Bone | 1.5 | 2.0 | 1.1 |
| Brain | 0.2 | 0.4 | 0.1 |

A detailed in this Example, model protein conjugates of PHF, a hydrophilic polyals, have been successfully prepared. Along with the conventional conjugation techniques employing acylation-based crosslinking, the bifunctional reagents of the invention allowing the formation of oxime bonds were used. Linkages formed by such reagents have the same pH sensitivity profile as the PHF backbone. PHF is a highly hydrophilic, essentially non-toxic semi-synthetic polymer (no toxicity in mice at 4 g/kg iv; See, for example, M Papisov et al. Semi-synthetic hydrophilic polyals. Under review (2002)) stable in physiological conditions but undergoing non-enzymatic hydrolysis at lysosomal pH. All previously tested PHF-containing preparations with MW exceeding 70 kDa exhibited long circulation in vivo, without significant RES uptake. The blood half-life of unmodified 500 kDa PMF was found to be more then 24 hours.

At 1:1 polymer:protein ratio, two conjugation techniques gave the highest coupling yields (95-98% by protein): the one-step method utilizing aminooxy-NHS coupling reagent VIII, and polymer succinylation followed by EDC mediated acylation. Protein adduct formation was accompanied with, on average, 1.5 to 2.0 fold increase in the number-average molecular weight (Mn). This can be an indication of crosslinking as the result of protein coupling with more than one polymer chain, which can be expected considering the reaction conditions. The conjugation process caused no noticeable effect on enzymatic activity of the conjugated proteins; from 85% to 95% of the original activity of native enzymes (synthetic substrates) was preserved in the conjugates. Other conjugation methods tested, such as reductive amination or coupling with aminooxy-maleimido coupling reagent VII, showed lower yields with respect to the model protein (trypsin), but might provide efficient coupling routes for other proteins.

The high site specificity of aminooxy reagents, mild coupling conditions (pH range 3-6), and high reaction rate (reaction half time less then 10 minutes for unprotected oximes at pH 5.5) all show that this group of compounds has a significant potential for preparation of protein conjugates. As expected, of the two crosslinker types tested the oxime linked conjugate showed higher degradation rate.

Animal data demonstrated PHF feasibility for designing long-circulating protein conjugates. Basic biokinetics data were obtained for two model PHF-Trypsin conjugates with Mn of ~250 kDa and ~350 kDa (SEC estimated particle size of approximately 14 nm and 15 nm and protein load of 10% and 25%, respectively). A 70-fold increase in the main fraction blood half-life was observed for both PHF-Trypsin conjugates, as compared to the unmodified trypsin (8 hours vs. 7 minutes), with reduced hepatic and renal uptake and no noticeable organ-specific accumulation. This data, notably obtained for unoptimized and unfractionated conjugates, is comparable with the average 35-fold blood half-life prolongation reported for circulation of PEG conjugates in rodents (see, for example, (1) Delgado C, Francis G, Fisher D. (1992) The uses and properties of PEG-linked proteins. *Crit. Rev. in Ther. Drug Carrier Syst.* 9, 249-304; and (2) Nucci M, Shorr R, Abuchovski A. (1991) The therapeutic value of poly(ethylene glycol) modified proteins. *Adv. Drug Del. Rev.* 6, 133-151).

The results suggest that both the oxime and ester modified polyals are feasible for preparation of fully functional biodegradable protein conjugates. The reversible, pH-sensitive character of the oxime linkage can be especially useful when pH dependent (e.g., lysosomal) drug release is desired.

Thus, all aspects of the obtained data suggest that PHF (and, likely, other semi-synthetic and fully synthetic hydrophilic polyals; See, for example, M. Yin et al. Fully synthetic hydrophilic polyacetals. Under review (2002)) have a significant potential as a platform for protein modification. In light of the present disclosure, PHF can be considered a viable and potentially superior biodegradable replacement for polyethylene glycol, especially in applications requiring chronic and/or high dose administration. The dependence of conjugate stability on the degree of PHF chain modification, protein load, crosslinker length and structure, as well as long term hydrolytic stability of the conjugates, is a subject of ongoing research. The work is being extended to prototype conjugates of clinically relevant proteins.

Bioconjugates comprising hydrophilic, essentially fully degradable polyacetal modules and model enzymes were successfully prepared with high yields and preservation of activity, utilizing conjugation strategies based on acylation as well as reductive and non-reductive amination. New aminooxyreagents enabling one step protein modification were developed to address the problem of preparation of essentially fully biodegradable bioconjugates. The data suggests several potential applications for both essentially fully degradable hydrophilic polyacetals and aminooxyreagents (e.g., bifunctional reagents of the invention) in protein modification, in particular where chronic or high dose administration is required.

Example 4

Hydrophilic Polyals: Biomimetic Biodegradable Stealth Materials for Pharmacology and Bioengineering As discussed above, acyclic hydrophilic polyals can be prepared via either polymerization of suitable monomers, or lateral cleavage of cyclic polyals (e.g., polysaccharides). Both fully synthetic and semi-synthetic polyals of various types were prepared and characterized in vitro and in vivo as model structural and interface components of bioconjugates, nanoparticles and other macromolecular and supramolecular constructs.

Experimental

Semi-Synthetic Polyals. In certain embodiments, semi-Synthetic Polyals were prepared from polyaldoses and polyketoses via complete lateral cleavage of carbohydrate rings with periodate in aqueous solutions, with subsequent conversion of aldehyde groups into hydrophilic or other pharmaceutically useful moieties, e.g. via borohydride reduction:

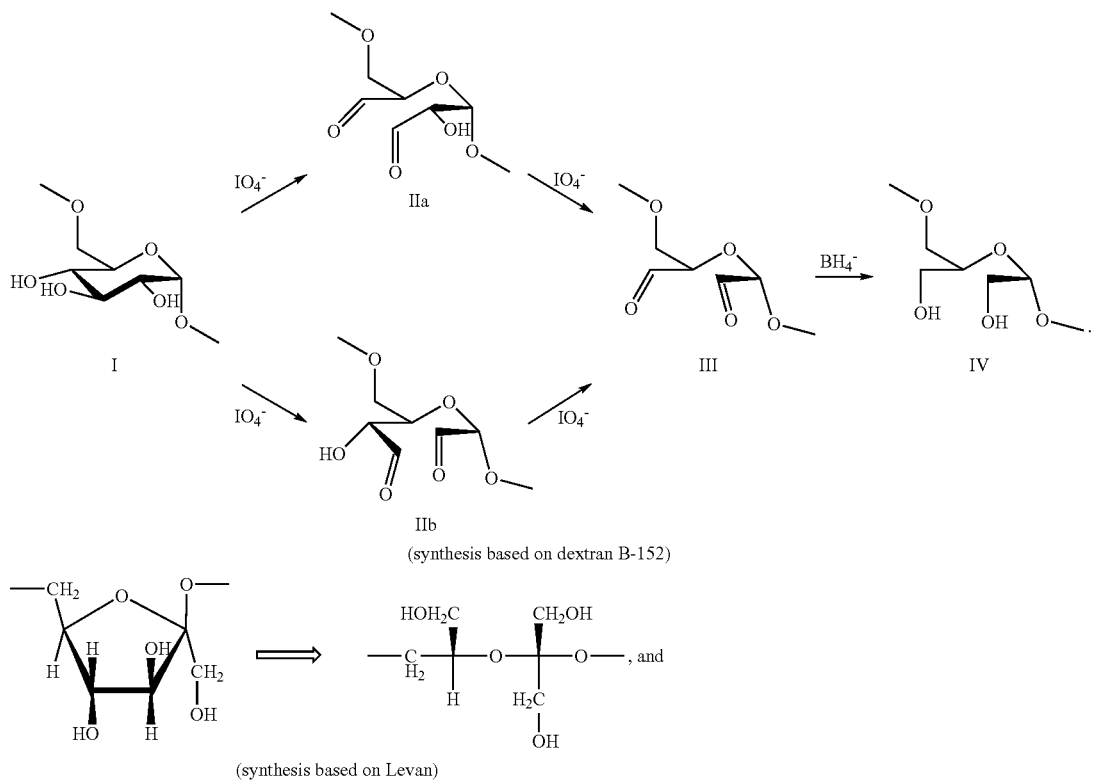

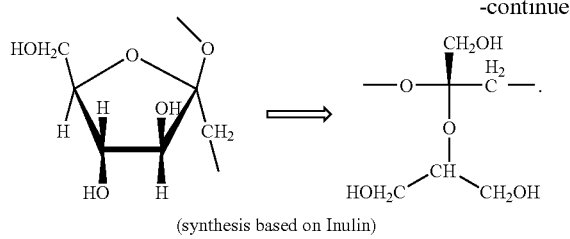

(synthesis based on Inulin)

Fully Synthetic Polyals. Condensation of vinyl ethers with protected substituted diols was found to be an affective method for hydrophilic polyal formation. Efficacy of other methods, such as cycle opening polymerization, depended on the degree of substitution and bulkiness of the protective groups.

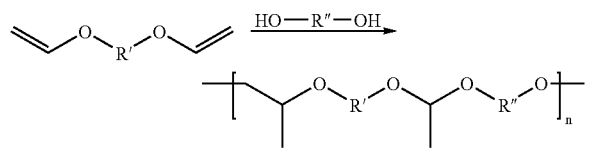

Solvent systems, catalysts and other factors were optimized to obtain high molecular weight products.

Model Derivatives. Synthetic and semisynthetic polyals were derivatized through either terminal or pendant functional groups to obtain model drug carriers and bioconjugates of various types.

Protected fully synthetic polyal with vinyl terminal groups (a product of condensation of mono-Fmoc-tris(hydroxymethyl)methane and ethylene glycol divinyl ether) was grafted to modified controlled pore glass, terminally modified with 1,2-Dipalmitoyl-sn-Glycero-3-Phosphothioethanol (PTE), then deprotected and cleaved from the support.

Semi-synthetic poly-(hydroxymethylethylene hydroxymethyl-formal) (PHF) was modified through the terminal vicinal glycol group present on one of the termini via periodate oxidation with either (a) subsequent reductive amination with 1,2-Dipalmitoyl-sn-Glycero-3-Phosphoethanolamine (PEA) or (b) non-reductive amination with aminooxyacetic acid.

Pendant hydroxyl groups in both synthetic and semi-synthetic polyals were modified via direct acylation or alkylation (e.g., with succinic anhydride or epichlorohydrine). Alternatively, semi-synthetic polymers with pendant 1,2-glycol groups were produced and derivatized through periodate oxidation followed by either reductive or non-reductive amination.

Terminal derivatives were further used to obtain polyal-modified liposomes, polyal-modified proteins and graft copolymers (model long-circulating nanocarriers). Pendant-modified polyal derivatives were used as structural backbones in various small molecule and protein conjugates.

Radiolabeling. For biokinetics studies, polyals, their derivatives and conjugates were labeled with $^{111}$In. Trace amounts of chelating diethylene triamine pentaacetate (DTPA) groups were introduced by direct acylation with DTPA dicycloanhydride. DTPA derivatives were labeled with $^{111}$In by transchelation from [$^{111}$In] indium citrate at pH=5.5 and purified by size exclusion HPLC.

In Vitro Characterization. Proton and $^{13}$C NMR were performed to characterize the structures of the obtained polyals and their derivatives. Hydrodynamic sizes were determined by size exclusion HPLC and, where appropriate, photon correlation light scattering. Hydrolytic depolymerization was studied in unbuffered and phosphate buffered aqueous media as a function of pH. Solubilities were studied in water and commonly used organic solvents. Activities of model polyal-modified enzymes (e.g., trypsin) were studied using synthetic substrates. Interaction of PHF with antibodies specific to the PHF precursor (dextran B-512) were studied by size exclusion HPLC and (using fluorophore-labeled antibodies) by fluorescence polarization lifetime investigation.

Cell Culture Models. Activities of clinically relevant model conjugates of interferon α (IFN) were studied in IFN-sensitive cell cultures (TF-1, A375). Binding of formylpeptide conjugates to white blood cells was performed using white blood cells isolated from rodent blood and conjugates co-labeled with a fluorophore (FITC).

Animal Models. Acute toxicity of the lead polyal (PHF) was studied in outbred mice at 0.1 mg/kg to 4 g/kg. Large molecular weight (>160 kDa) polymer preparations were used to avoid renal clearance that would mask the possible toxic effects.

Biokinetics and biodistributions were studied by blood and tissue sampling in rats, mice and rabbits using $^{111}$In labeled prepartations at clinically relevant doses. Fast initial stages (if present) were studied by dynamic gamma-scintigraphy in anesthetized animals.

Biokinetics of unmodified polyals of various molecular weights were studied in normal mice, rats and rabbits. Biokinetics of model nanocarriers (PHF graft copolymers) and polyal-modified liposomes were studied in rats. Biokinetics of formylpeptide conjugates were studied in normal rabbits and rabbits with focal bacterial inflammation. Protein conjugates were studied in mice and rats.

Toxicities and biological activities of model conjugates (IFN, G-CSF, antineoplastic small molecules) were studied in mice, using relevant models (Cytoxan challenge for G-CSF; cancer xenografts in nude mice for antineoplastic preparations)

Synthesis and characterization. In the semi-synthetic polyal syntheses, yields and molecular weights of the products were found to vary depending on the precursor polysaccharide. Polyals from polysaccharide precursors of high regularity and low branching, such as dextran B-512 and inulin, were obtained practically without depolymerization and with nearly theoretical yields. SEC HPLC elution profiles of the products practically reproduced the profiles of the respective precursor polysaccharides (e.g., from 3 kDa to 1,500 kDa for PHF). Dextran B-512-specific antibodies did not bind PHF.

In the vinyl ether condensation-based syntheses, several protected diol derivatives were tested and found to be equally effective at the polymerization stage. However, Fmoc protection was found to enable better yields at the subsequent derivatization and deprotection stages. Fully synthetic polyals with 5-15 kDa main fraction were produced with high yields. Large molecular weight preparations (>35 kDa) were isolated by fractionation.

All obtained polymers were examined by $^{13}$C and $^1$H NMR, and were found to be in agreement with the expected fully acyclic polyal structures. Polyals showed the expected profile of hydrolytic degradation, being essentially stable at pH from 7 to ca. 10.5, and hydrolyzable at lysosomal pH of 5. Large molecular weight polyals (MW>50 kDa) were soluble in water and several organic solvents (e.g. DMF, DMSO, Py). Lower MW fractions were also soluble in methanol and Py/methanol and other solvents and mixtures.

Polyals tested to date in animals were found to be essentially non-toxic. The most extensively studied PHF showed no signs of toxicity and no weight loss even after intravenous administration of 4 gram per kg of body weight.

Biokinetics and biodistribution of $^{111}$In labeled PHF was studied in rats. Low molecular weight fractions were found to be rapidly excreted through kidneys without significant accumulation in any tissue. For a 50 kDa preparation, blood half-life was 2 hours with label content in tissues below 0.05% injected dose/g (24 hours post injection). High molecular weight fractions (e.g., 500 kDa) had long blood half-lives (25 hours), with no preferential accumulation in any tissue (generally, below 0.2% dose/g at 72 hours). Hepatic, splenic and lymphatic accumulation levels were not much higher than in other tissues (0.4±0.1% dose/g), suggesting spontaneous liquid phase endocytosis, rather than phagocyte recognition, as the main uptake mechanism.

Derivatives. Terminal and pendant group derivatives were successfully prepared for in vitro and in vivo characterization.

Protein conjugates. Succinyl-PHF was used to prepare model protein conjugates (trypsin, IFN, G-CSF) with protrein:polymer ratio from ca. 1:1 to 1:2 with nearly theoretical yields (by protein). The conjugates showed the expected increase in hydrodynamic diameter (to ca. 10-11 nm) and insignificant (0%-5%) loss of specific activity, as measured in vitro or in cell culture models. All protein conjugates showed dramatic improvements in biokinetics, e.g., blood half-life increases from 7 and 11 minutes to 8 and 13 hours (trypsin and IFN, respectively), and a 5-10 fold reduction in renal accumulation upon both IV and SC administration. The G-CSF conjugate was found to retain the in vivo activity, and had a potentially superior activity dynamics. The initial data obtained with model hemoglobin and other conjugates suggested that protein-polyal conjugates, unlike analogous conjugates of PEG, caused a much less significant or no renal vacuolization, probably depending on the dose and timeframe (work in progress).

Small Peptide. Formylpeptide N-formyl-Met-Leu-Phe-Lys) conjugates were found to have high affinity to white blood cells (via formylpeptide receptor). Administration of such (labeled) conjugates in rats and rabbits resulted in efficient in vivo labeling of white blood cells and their invasions in focal bacterial inflammations. While inflammation labeling efficacy was equal to that of unmodified formylpeptide, renal accumulation (and, respectively, radiation does) was reduced by 81-88%, depending on the molecular weight, and hepatic and splenic accumulations were reduced by 40% for low molecular weight (15 kDa) preparations.

Liposomes. Polyal-modified 100 nm DPPC/Cholesterol liposomes showed a significantly prolonged circulation upon IV administration in rats vs. unmodified liposomes, e.g., 50% clearance during 30 min. vs. 90% clearance during 15 min., respectively. Work is in progress to optimize polyal content and molecular weight in order to obtain fully biodegradable long-circulating liposomes.

Drug carriers. Model sterically protected nanocarriers (hydrodynamic diameter 16±4 nm) assembled using 20 kDa poly-L-lysine as a backbone and 10 kDa PHF as protective graft showed strong correlation of blood half-life (rat) with the number of PHF chains per backbone. While unprotected polylysine has blood half-life of ca. 20 seconds, PHF-modified carriers with 10 and 20 graft molecules per backbone had half-lives of 9.8 and 25.3 hours, respectively.

Small molecule conjugates. Being strongly hydrophilic (in some cases even hygroscopic) polymers, polyals are suitable for solubilizing strongly hydrophobic small molecules. Several small molecule conjugates were prepared through either direct acylation of polyals (DTPA cycloanhydride, succinic anhydride) or alkylation (epichlorohydrine), or through non-reductive amination using bifunctional aminooxy-reagents developed in our laboratories ($H_2N$—O—R—X, where X is a functional group, e.g., N-maleimide or N-hydroxysuccinimide ester). Conjugates of model antineoplastic drugs were soluble at drug content from at least ca. 5-7% w/w (most hydrophobic substances) to ca. 15% (anthracyclines, such as doxorubicine). One of such conjugates was tested in mouse xenograft models (LS174t and HT26 in nude mice) and demonstrated lower toxicity and higher antineoplastic activity than the respective unmodified drug. For example, animal survival 55 days post treatment start was 80% in the conjugate-treated group vs. 40% in the group treated with unmodified drug (same dose), and 20% in the untreated control group. Optimization of conjugate size, composition and conjugation/release chemistry is a subject of our ongoing work.

One goal of this study was to determine whether a macromolecular material built of the common acyclic structures of carbohydrates would have the set of features necessary for advanced pharmacological engineering. These include "inertness" in vivo (non-bioadhesiveness, or "stealth" properties), biodegradability of the main chain, low toxicity, and technological flexibility.

The polyal main chain was found to be stable at physiological conditions (pH=7 and above) but sensitive to proton-catalyzed hydrolysis at pH<7. Low pH is characteristic for the intracellular lysosomal and caveolar compartments. Therefore, cellular uptake of polyal-based preparations can be expected to result in complete non-enzymatic hydrolysis of the main chain at a moderate rate. The constitutive units of polyals have low toxicity and can be metabolized via major metabolic pathways and/or excreted. As compared to hydrolysis-resistant polymers, e.g., polyethyleneglycol, this appears to be a significant advantage, especially in preparations intended for high dose or chronic administration, where long-term cell vacuolization, intracellular polymer storage, and the associated functional abnormalities can result in significant safety risks.

For particles and large macromolecules, blood half-life is a mathematically exact measure of the overall polymer reactivity [Papisov M. I., *Adv. Drug Delivery Rev.*, 1995, 16:127-137]. The results of in vivo evaluation of the lead polyal (PHF) showed that neither linear nor highly branched derivatives were recognized by reticuloendothelial cells. The obtained biokinetics data provides a clear evidence that the central goal of this study, developing of biodegradable materials with minimized interactions with biological milieu, have been achieved.

Hydrophilic polyals of various structures have been successfully synthesized. These polymers demonstrated excellent technological flexibility and biological properties. The obtained data suggests several potential applications for these hydrophilic, essentially fully biodegradable polymers, in particular in advanced drug delivery systems, protein and small molecule modification, and drug carrier engineering.

Pierce Chemical Technical Library cross-linking

Applications for Use of Cross-linkers

Cell Surface Cross-linking

To ensure cell-surface specific cross-linking for identification of surface receptors or their ligands, it is best to use membrane-impermeable cross-linkers. In the past, researchers used water-insoluble cross-linkers and carefully controlled the amount of cross-linker and the cross-linking duration. This prevented penetration of the membrane by the cross-linker and subsequent reaction with membrane proteins. Many references cite the use of membrane-permeable cross-linkers for cell surface cross-linking. Staros developed water-soluble sulfo-NHS analogs as alternatives to membrane permeable, homobifunctional NHS-ester and imidoester cross-linkers.[26] The sulfo-NHS-ester, homobifunctional cross-linker $BS_3$ (Product #21579) is very useful for cell surface cross-linking of ligands to receptors through primary amines on each. The sulfonyl groups attached to the succinimidyl rings of sulfo-NHS cross-linkers make them membrane-impermeable and non-reactive with inner membrane proteins. Therefore, cross-linking time and quantity of cross-linker are less critical when using sulfo-NHS-esters. Pierce offers a variety of sulfo-NHS-ester cross-linkers, both homobifunctional and heterobifunctional. Homobifunctional sulfo-NHS-esters, heterobifunctional sulfo-NHS-esters and photoreactive phenyl azides are good choices for cross-linking on the surface of a cell. See Tables 3, 5 and 9 for specific characteristics and selection of cross-linkers for cell surface applications.

Telephone: 800.874.3723 or 815.968.0747   Fax: 800.842.5007 or 815.968.7316
Internet: http://www.piercenet.com   E-mail: TA@piercenet.com

Pierce Chemical Technical Library cross-linking

Table 3: Homobifunctional NHS-Ester Cross-linkers (Continued)

| Cross-linker | Product # | M.W. | Spacer Arm Length | Reactivity/Characteristics | Applications/References |
|---|---|---|---|---|---|
| DSP<br>Dithiobis(succinimidyl propionate)<br>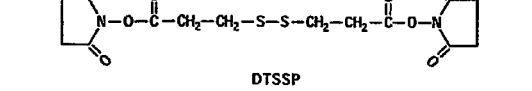DSP | 22585 | 404.42 | 12 Å | One of the most widely used cross-linkers, also known as Lomant's Reagent.[71] Water-insoluble, thiol-cleavable—can be cleaved with 10-50 mM DTT at 37°C for 30 minutes or with 5% β-mercaptoethanol in SDS-PAGE sample buffer (2% SDS, 6.25 mM Tris base, 10% glycerol) at 100°C for 5 minutes. | • Examining spatial relationships of the capsid polypeptides of the mengo virion[91]<br>• Studying renal Na+ and K+-ATPase[92]<br>• Nearest neighbor relationships of bovine mitochondrial H+-ATP[93]<br>• Producing interactions between protein components of the chemotaxis mechanism in E. coli[94]<br>• Chemical cross-linking of a-CPI[95]<br>• Identifying cross-linked cytochrome P-450 in rat liver microsomes[96]<br>• Studying the influence of metal ions on prothrombin self-association[97]<br>• Studying glycoprotein topology on intact human red blood cells[98]<br>• Molecular identification of receptors for vasoactive intestinal peptide in rat intestinal epithelium[99]<br>• Characterization of a cell surface receptor for colony-stimulating factor (CSF-2a)[100]<br>• Determining membrane antigens by covalent cross-linking to monoclonal antibodies[101] |
| DTSSP [3,3'-Dithiobis(sulfosuccinimidyl propionate)]<br>DTSSP | 21577 | 608.51 | 12 Å | Water-soluble analog of DSP[88] | • Cross-linking the extracytoplasmic domain of the anion exchange channel in intact human erythrocytes[68]<br>• Cross-linking studies on Novikoff ascites hepatoma cytokeratin filaments[89]<br>• Characterization of the B lymphocyte Fc receptor for IgE[90]<br>• Cross-linking platelet glycoprotein Ib[102]<br>• Characterization of a membrane-ribosome complex in B. subtilis[103] |

Pierce Chemical Technical Library cross-linking

Table 3: Homobifunctional NHS-Ester Cross-linkers (Continued)

| CROSS-LINKER | PRODUCT # | M.W. | SPACER ARM LENGTH | REACTIVITY/ CHARACTERISTICS | APPLICATIONS/ REFERENCES |
|---|---|---|---|---|---|
| EGS Ethylene glycobis (succinimidylsuccinate) | 21565 | 456.37 | 16.1 Å | Water-insoluble hydroxylamine. Cleavable—cleaved by incubating with 1 M hydroxylamine for 3-6 hours at 37°C at pH 8.5. Lactose dehydrogenase retained 60% of its activity after cross-linking with EGS.[64] | • Cross-linking studies of cytochrome P-450 and reduced nicotinamide adenine dinucleotide phosphate-cytochrome P-450 reductase[105]<br>• Tumor necrosis factor (TNF) and lymphotoxin LT cross-linking[106]<br>• Converting a gonadotropin-releasing hormone antagonist to an agonist[107]<br>• Preparing the EGS dimer of the GnRH agonist D-Lys-GnRH[108]<br>• Covalent cross-linking of vasoactive peptide to its receptors on intact human lymphoblasts[75]<br>• Binding and cross-linking of $^{125}$I-gastrin releasing peptid (GRP)[109] |
| Sulfo-EGS Ethylene glycobis(sulfo-succinimidylsuccinate) | 21566 | 660.47 | 16.1 Å | Water-soluble analog of EGS. Reactions similar to EGS.[104] | 104 |
| DST Disuccinimidyl tartarate | 20590 | 344.24 | 6.4 Å | Water-insoluble sample cross-linked with DST in first-dimensional gel. Cleavable by soaking in 0.015 M sodium periodate, 0.1% SDS, 0.02 M sodium phosphate, pH 7.0 for 2 hours (with several changes) at room temperature.[110] | • Cross-linking of ubiquinone cytochrome c reductase (complex III)[110]<br>• Characterization of the cell surface receptor for colony-stimulating factor (CSF-2a)[111]<br>• Cross-linking study of the Ca²⁺, Mg²⁺ activated adenosine triphosphate of E. coli[80]<br>• Human promyelocytic cell line cross-linking of cell lysate with DST[112] |
| Sulfo-DST Disulfosuccinimidyl tartarate | 20591 | 548.34 | 6.4 Å | Water-soluble analog of DST | 100, 110-112 |

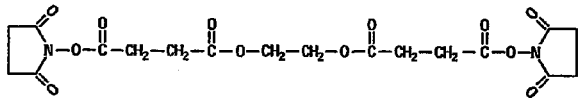
EGS

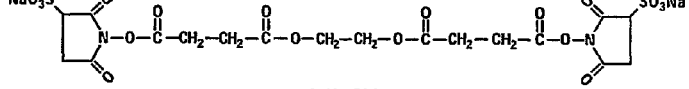
Sulfo-EGS

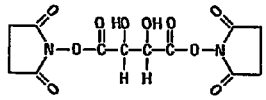
DST

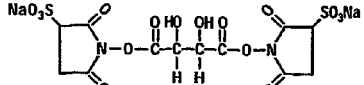
Sulfo-DST

Pierce Chemical Technical Library cross-linking

Table 3: Homobifunctional NHS-Ester Cross-linkers (Continued)

| CROSS-LINKER | PRODUCT # | M.W. | SPACER ARM LENGTH | REACTIVITY CHARACTERISTICS | APPLICATIONS/ REFERENCES |
|---|---|---|---|---|---|
| EGS<br>Ethylene glycobis(succinimidylsuccinate) | 21565 | 456.37 | 16.1 Å | Water-insoluble hydroxylamine. Cleavable—cleaved by incubating with 1 M hydroxylamine for 3-6 hours at 37°C at pH 8.5. Lactose dehydrogenase retained 60% of its activity after cross-linking with EGS.[104] | • Cross-linking studies of cytochrome P-450 and reduced nicotinamide adenine dinucleotide phosphate-cytochrome P-450 reductase[105]<br>• Tumor necrosis factor (TNF) and lymphotoxin LT cross-linking[106]<br>• Converting a gonadotropin-releasing hormone antagonist to an agonist[107]<br>• Preparing the EGS dimer of the GnRH agonist D-Lys-GnRH[108]<br>• Covalent cross-linking of vasoactive peptide to its receptors on intact human lymphoblasts[a]<br>• Binding and cross-linking of $^{125}$I-gastrin releasing peptid (GRP)[109] |
| Sulfo-EGS<br>Ethylene glycobis(sulfo-succinimidylsuccinate) | 21566 | 660.47 | 16.1 Å | Water-soluble analog of EGS. Reactions similar to EGS.[104] | 104 |
| DST<br>Disuccinimidyl tartarate | 20590 | 344.24 | 6.4 Å | Water-insoluble sample cross-linked with DST in first-dimensional gel. Cleavable by soaking in 0.015 M sodium periodate, 0.1% SDS, 0.02 M sodium phosphate, pH 7.0 for 2 hours (with several changes) at room temperature.[110] | • Cross-linking of ubiquinone cytochrome c reductase (complex III)[110]<br>• Characterization of the cell surface receptor for colony-stimulating factor (CSF-2a)[111]<br>• Cross-linking study of the Ca$^h$, Mg$^h$ activated adenosine triphosphate of E. coli[80]<br>• Human promyelocytic cell line cross-linking of cell lysate with DST[112] |
| Sulfo-DST<br>Disulfosuccinimidyl tartarate | 20591 | 548.34 | 6.4 Å | Water-soluble analog of DST | 100,110-112 |

Telephone: 800.874.3723 or 815.968.0747   Fax: 800.842.5007 or 815.968.7316
Internet: http://www.piercenet.com   E-mail: TA@piercenet.com

Pierce Chemical Technical Library cross-linking

Table 5: NHS-Ester-Maleimide Heterobifunctional Cross-linkers

| CROSS-LINKER | PRODUCT # | M.W. | SPACER ARM LENGTH | REACTIVITY/ CHARACTERISTICS | APPLICATIONS/ REFERENCES |
|---|---|---|---|---|---|
| SMCC<br>Succinimidyl 4-(N-maleimidomethyl) cyclohexane-1-carboxylate<br>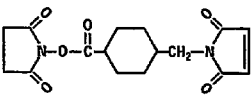 | 22320 | 334.33 | 11.6 Å | Water-insoluble, noncleavable, very stable. Maleimide-reactive group. | • Conjugation of glucose oxidase from Aspergillus niger to rabbit antibodies[45]<br>• Conjugating Fab' to horseradish peroxidase[116-119, 125]<br>• Conjugating affinity-purified antidigoxin F(ab')$_2$ fragments to β-galactosidase[120]<br>• Enzyme labeling of antibodies and antibody fragments[121]<br>• Conjugating alkaline phosphatase and human IgG F(ab')$_2$ fragments for phase change immunoassays[122]<br>• Preparing immunogens[123,124] |
| Sulfo-SMCC<br>Sulfo-succinimidyl 4-(N-maleimidomethyl) cyclohexane-1-carboxylate<br>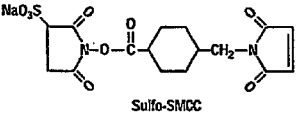 | 22322 | 436.37 | 11.6 Å | Water-soluble analog of SMCC; very stable maleimide-reactive group. This noncleavable cross-linker is membrane impermeable. | • A comparison of maleimide containing heterobifunctional cross-linkers in the conjugation of Fab' fragments to horseradish peroxidase[126]<br>• Preparation of enzyme-antibody conjugates[127] |
| MBS<br>m-Maleimidobenzoyl-N-hydroxysuccinimide ester<br>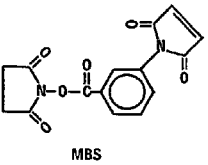 | 22310 | 314.2 | 9.9 Å | Water-insoluble, noncleavable cross-linker | • Preparing an insulin-β-galactosidase conjugate[128]<br>• Conjugating hen egg ovalbumin with thiolated synthetic copolymers of D-glutamic acid and D-lysine[129]<br>• Preparing antibody-β-galactosidase conjugates[130]<br>• Producing ricin immunotoxins[131,142]<br>• Preparing hapten-carrier protein conjugates from peptides[132,137,138,140,141]<br>• Coupling blasticidin S to bovine serum albumin[133]<br>• Preparing Fab'-β-galactosidase conjugates[134]<br>• Preparing synthetic peptide antigens for making antibodies to detect oncogene-related proteins[135]<br>• Investigating the mechanism of cytotoxicity of diphtheria toxin coupled to anti-CD3 MAb[136]<br>• Preparing enzyme labeled viomycin[139] |

Pierce Chemical Technical Library cross-linking

Table 5: NHS-Ester-Maleimide Heterobifunctional Cross-linkers (Continued)

| CROSS-LINKER | PRODUCT # | M.W. | SPACER ARM LENGTH | REACTIVITY/ CHARACTERISTICS | APPLICATIONS/ REFERENCES |
|---|---|---|---|---|---|
| Sulfo-MBS<br>m-Maleimidobenzoyl-N-hydroxysulfosuccinimide ester<br>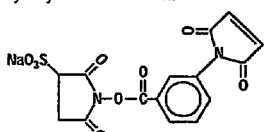<br>Sulfo-MBS | 22312 | 416.24 | 9.9 Å | Water-soluble analog of MBS; noncleavable, membrane impermeable. | • An alternative method utilizing small quantities of ligand for affinity purification of monospecific antibodies[143]<br>• Coupling of antibody to ß-D-galactosidase[144] |
| SMPB<br>Succinimidyl 4-(p-maleimidophenyl)-butyrate<br>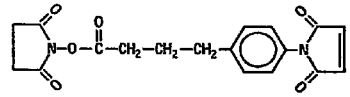<br>SMPB | 22315 | 356.32 | 14.5Å | Water-insoluble, extended spacer arm to limit steric hindrance; noncleavable. | • Conjugation of preformed vesicles and Fab' fragments in a study of liposomes as a carrier system[144]<br>• Attaching insulin molecules to reconstituted Sendai virus envelopes[145]<br>• Targeting of loaded Sendai virus envelopes by covalently attached insulin molecules to virus receptor-depleted cells[146]<br>• Forming alkaline phosphatase-Fab' fragment conjugates for an enzyme immunoassay system[147]<br>• Preparing peptide-protein immunogens[148] |
| Sulfo-SMPB<br>Sulfosuccinimidyl 4-(p-maleimidophenyl)-butyrate<br>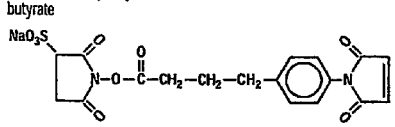<br>Sulfo-SMPB | 22319 | 458.36 | 14.5Å | Water-soluble analog of SMPB. Extended spacer arm to limit steric hindrance; non-cleavable, membrane impermeable. | • Studying the transport of the varient surface glycoprotein of Trypanosome brucia[149]<br>• Using aromatic cross-linkers such as Sulfo-SMPB to improve the yield of immunotoxin conjugates[142] |
| BMH<br>Bismaleimidohexane<br>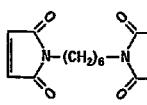<br>BMH | 22319 | 276.29 | 16.1Å | Water-insoluble homobifunctional cross-linker employing two maleimide functional groups; noncleavable. | • Structural and functional studies of cross-linked $Go_{150}$ protein subunits[150]<br>• Studies of lymphocyte function-associated antigen-3 (LFA-3)[151]<br>• Producing multimeric forms of CD4[152] |

Telephone: 800.874.3723 or 815.968.0747   Fax: 800.842.5007 or 815.968.7316
Internet: http://www.piercenet.com   E-mail: TA@piercenet.com

Pierce Chemical Technical Library cross-linking

Table 5: NHS-Ester-Maleimide Heterobifunctional Cross-linkers (Continued)

| CROSS-LINKER | PRODUCT # | M.W. | SPACER ARM LENGTH | REACTIVITY/ CHARACTERISTICS | APPLICATIONS/ REFERENCES |
|---|---|---|---|---|---|
| GMBS<br>N-(g-maleimidobutyryloxy) succinimide ester<br>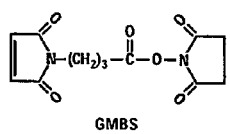<br>GMBS | 22314 | 280.24 | 10.2 Å | Water-insoluble, noncleavable. | • Acylation of antibody to introduce maleimide groups[153] |
| Sulfo-GMBS<br>N-(g-maleimidobutyryloxy) sulfosuccinimide ester<br>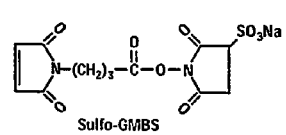<br>Sulfo-GMBS | 22324 | 382.28 | 10.2 Å | Water-soluble analog of GMBS; noncleavable, membrane impermeable. | 154-155 |

Pierce Chemical Technical Library cross-linking

Table 9: Photoreactive Cross-linkers

| CROSS-LINKER | PRODUCT # | M.W. | SPACER ARM LENGTH | REACTIVITY | APPLICATIONS/ REFERENCES |
|---|---|---|---|---|---|
| ABH Azidobenzoyl Hydrazide | 21510 21509 | 177.17 | | • Hydrazide • Phenylazide | • Glycoprotein receptor studies[168] |
| ANB-NOS N-5-Azido-2-nitrobenzoyloxysuccinimide | 21551 | 305.21 | 7.7 Å | • NHS-ester • Phenylazide | • Cross-linking cobra venom phospholipase A2 aggregation state[169] • Photo-cross-linking of the signal sequence of nascent preprolactin to a polypeptide of the signal recognition particle[170] |
| APDP N-[4-(p-azidosalicylamido) butyl]-3'(2'-pyridyldithio) propionamide | 27720 | 446.55 | | • Pyridyl disulfide • Phenylazide | • Cross-linking of protein subunits and ligand by introduction of disulfide bonds[171] |
| APG p-Azidophenyl glyoxal monohydrate | 20107 | 193.16 | 9.3 Å | • Phenylazide • Phenyl glyoxal | • Inhibiting bovine heart lactic dehydrogenase, eggwhite lysozyme, horse liver alcohol dehydrogenase, and yeast alcohol dehydrogenase[172] • Cross-linking ribonucleic acid-protein in E. coli ribosomes[173] • Identifying regions of brome mosaic virus coat protein chemically cross-linked in situ to viral RNA[174] |

Telephone: 800.874.3723 or 815.968.0747  Fax: 800.842.5007 or 815.968.7316
Internet: http://www.piercenet.com  E-mail: TA@piercenet.com

Pierce Chemical Technical Library cross-linking

Table 9: Photoreactive Cross-linkers (Continued)

| CROSS-LINKER | PRODUCT # | M.W. | SPACER ARM LENGTH | REACTIVITY | APPLICATIONS/REFERENCES |
|---|---|---|---|---|---|
| ASBA<br>4-(p-Azidosalicyl-amido)butylamine<br>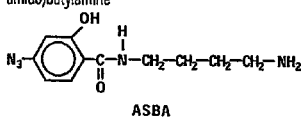<br>ASBA | 21512 | 249.27 | 16.3 Å | • Carbonyl reactive<br>• Phenylazide | |
| ASIB<br>1-(p-Azidosalicyl-amido)-4-(iodo-acetamido)butane<br>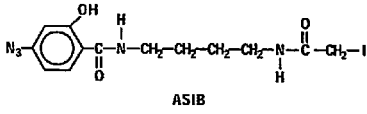<br>ASIB | 21511 | 417.21 | 18.8 Å | • Iodoacetyl<br>• Phenylazide | |
| BASED<br>Bis-[β-4-azidosalicylamido)ethyl]disulfide<br>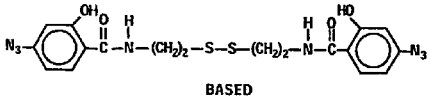<br>BASED | 21564 | 474.54 | | • Phenylazide<br>(homobifunctional) | • Receptor location<br>• Near neighbor analysis<br>• Protein structural studies<br>• Appropriate in the absence of primary amines and thiols |
| HSAB<br>N-Hydroxysuccinimidyl-4-azidobenzoate<br>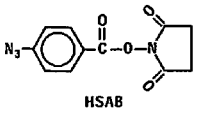<br>HSAB | 21560 | 260.21 | 8.0 Å | • NHS-ester<br>• Phenylazide | • Photoaffinity labeling of peptide hormone binding sites[175]<br>• Photoaffinity labeling of insulin receptor with an insulin analog[176]<br>• Identifying nerve growth factor receptor proteins in sympathetic ganglia membranes[177]<br>• Photoaffinity labeling the hormone receptor of both α and β subunits of human choriogonadotropin[178]<br>• Isolating *in situ* cross-linked ligand-receptor complexes[179]<br>• Cross-linking vasoactive intestinal polypeptide to its receptors on intact human lymphocytes[74] |

Telephone: 800.874.3723 or 815.968.0747   Fax: 800.842.5007 or 815.968.7316
Internet: http://www.piercenet.com   E-mail: TA@piercenet.com

Pierce Chemical Technical Library cross-linking

Table 9: Photoreactive Cross-linkers (Continued)

| CROSS-LINKER | PRODUCT # | M.W. | SPACER ARM LENGTH | REACTIVITY | APPLICATIONS/REFERENCES |
|---|---|---|---|---|---|
| Sulfo-HSAB<br>N-Hydroxysulfo-succinimidyl 4-azidobenzoate | 21561 | 362.25 | 9.0 Å | • NHS-ester<br>• Phenylazide | • Photoaffinity labeling of peptide hormone binding sites[175]<br>• See applications for HSAB |
| NHS-ASA<br>N-Hydroxysuccinimidyl-4-azidosalicylic acid | 27715 | 276.21 | 8.0 Å | • NHS-ester<br>• Phenylazide | • Photoaffinity labeling of [125]I-AS-Con A to erythrocyte ghosts[180]<br>• Derivatizing human choriogonadotropin with $^{125}$I-NHS-ASA and photo-cross-linking the αβ dimer[181]<br>• Radiolabeling D-glucose and cross-linking the sugar to the human erythrocyte mono saccharide transporter[182]<br>• Photoaffinity labeling of a bacterial sialidase[183] |
| Sulfo-NHS-ASA<br>N-Hydroxysulfo-succinimidyl-4-azidosalicylic acid | 27725 | 378.25 | 8.0 Å | • NHS-ester<br>• Phenylazide | • See applications/references for NHS-ASA |
| Sulfo-NHS-LC-ASA<br>Sulfosuccinimidyl-(4-azidosalicylamido)-hexanoate | 27735 | 491.41 | 18 Å | • NHS-ester<br>• Phenylazide | • See applications/references for NHS-ASA |

Telephone: 800.874.3723 or 815.968.0747   Fax: 800.842.5007 or 815.968.7316
Internet: http://www.piercenet.com   E-mail: TA@piercenet.com

Pierce Chemical Technical Library cross-linking

Table 9: Photoreactive Cross-linkers (Continued)

| CROSS-LINKER | PRODUCT # | M.W. | SPACER ARM LENGTH | REACTIVITY | APPLICATIONS/REFERENCES |
|---|---|---|---|---|---|
| PNP-DTP<br>p-Nitrophenyl-<br>2-diazo-3,3,3-trifluoropropionate<br><br>$F_3C-\underset{\underset{N_2}{\|\|}}{C}-\underset{\underset{O}{\|\|}}{C}-O-\langle\text{phenyl}\rangle-NO_2$<br><br>PNP-DTP | 20669 | 276.15 | | • Diazo | • Photoaffinity labeling of thyroid hormone nuclear receptors in intact cells[184,185] |
| DTP<br>2-Diazo-3,3,3,-trifluoro-<br>propionylchloride<br><br>$F_3C-\underset{\underset{N_2}{\|\|}}{C}-\underset{\underset{O}{\|\|}}{C}-Cl$<br><br>DTP | 20670 | | | • Sulfhydryls<br>• Amines | • Pierce offers this product for researchers who require the acid chloride precursor of PNP-DTP |
| SADP<br>N-succinimidyl-<br>(4-azidophenyl)<br>1,3'-dithiopropionate<br><br>$N_3-\langle\text{phenyl}\rangle-S-S-CH_2-CH_2-\underset{\underset{O}{\|\|}}{C}-O-N\langle\text{succinimidyl}\rangle$<br><br>SADP | 21552 | 352.38 | 13.9 Å | • NHS-ester<br>• Phenylazide | • Cross-linking concanavalin A to receptors on the human erythrocyte membrane[186]<br>• Preparing photoactivatable glycopeptide reagents for site-specific labeling of lectins[187]<br>• Attaching a Sendai virion envelope and a mouse surface membrane polypeptide on newly infected cells[188]<br>• Cross-linking platelet glycoprotein 1b[189] |
| Sulfo-SADP<br>Sulfosuccin<br>(4-azidophenyldithio)<br>propionate<br><br>$N_3-\langle\text{phenyl}\rangle-S-S-CH_2-CH_2-\underset{\underset{O}{\|\|}}{C}-O-N\langle\text{succinimidyl-}SO_3Na\rangle$<br><br>Sulfo-SADP | 21553 | 454.45 | 13.9 Å | • NHS-ester<br>• Phenylazide | • See applications/references for SADPimidyl- |

Pierce Chemical Technical Library cross-linking

Table 9: Photoreactive Cross-linkers (Continued)

| CROSS-LINKER | PRODUCT # | M.W. | SPACER ARM LENGTH | REACTIVITY | APPLICATIONS/REFERENCES |
|---|---|---|---|---|---|
| SAED<br>Sulfosuccinimidyl 2-(7-azido-4-methylcoumarin-3-acetamide) ethyl-1,3'-dithiopropionate | 33030 | 621.60 | 23.6 Å | • NHS-ester<br>• Phenylazide<br>• Fluorescent | • Functionally directed region specific fluorescent labeling of proteins[189]<br>• Assessing conformational changes in the foot protein of the sarcoplasmic reticulum by site-directed fluorescent labeling[190] |

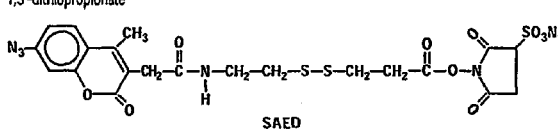

SAED

| Sulfo-SAMCA<br>Sulfosuccinimidyl 7-azido-4-methylcoumarin-3-acetate | 33025 | 458.34 | 12.8 Å | • NHS-ester<br>• Phenylazide<br>• Fluorescent | • Specific fluorescent labeling |

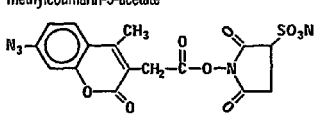

Sulfo-SAMCA

| SAND<br>Sulfosuccinimidyl 2-(m-azido-o-nitrobenzamido)-ethyl-1,3'-dithiopropionate | 21549 | 570.52 | 18.5 Å | • NHS-ester<br>• Phenylazide | • Demonstration of the aggregation state of Phospholipase $A_2$[165] |

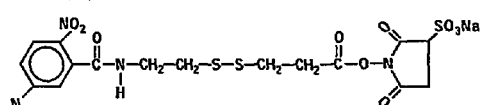

SAND

Pierce Chemical Technical Library cross-linking

Table 9: Photoreactive Cross-linkers (Continued)

| CROSS-LINKER | PRODUCT # | M.W. | SPACER ARM LENGTH | REACTIVITY | APPLICATIONS/REFERENCES |
|---|---|---|---|---|---|
| SANPAH<br>N-succinimidyl-6-(4'-azido-2'-nitrophenyl-amino)hexanoate | 22588 | 390.95 | 18.2 Å | • NHS-ester<br>• Phenylazide | • Cross-linking ligand-receptor complexes *in situ*[175]<br>• Preparing photoactivatable glycopeptide reagents for site-specific labeling of lectins[196]<br>• Photoaffinity labeling of the N-formyl peptide receptor binding site of intact human polymorphonuclear leukocytes[191]<br>• Cross-linking vasoactive intestinal peptide to receptors on intact human lymphoblasts[76] |
| Sulfo-SANPAH<br>Sulfosuccinimidyl 6-(4'-azido-2'-nitrophenylamino)hexanoate | 22589 | 492.39 | 18.2 Å | • NHS-ester<br>• Phenylazide | • See applications/references for SANPAH |
| SASD<br>Sulfosuccinimidyl 2-(p-azidosalicyl-amido)ethyl-1,3'-dithiopropionate | 27716 | 541.51 | 18.9 Å | • NHS-ester<br>• Phenylazide | • Derivatization of bacterial lipopolysaccharide[192]<br>• Identification of the murine interleukin receptor and N-formyl peptide receptor[193]<br>• Comparison of SASD radiolabeling techniques[194]<br>• Cross-linking of factor V and Va to iodinated peptides[195] |
| Sulfo-SAPB<br>Sulfosuccinimidyl 4-(p-azidophenyl)-butyrate | 21562 | 404.32 | 12.8 Å | • NHS-ester<br>• Phenylazide | |

Telephone: 800.874.3723 or 815.968.0747   Fax: 800.842.5007 or 815.968.7316
Internet: http://www.piercenet.com   E-mail: TA@piercenet.com

Pierce Chemical Technical Library cross-linking

References

26. Staros, J.V., Morgan, D.G. and Appling, D.R. (1981). A membrane-imper-meant, cleavable cross-linker. *J. Biol. Chem.* 256(11), 5890-5893.
71. Pilch, P.F. and Czech, M.P. (1979). Interaction of crosslinking agents with the insulin effector system of isolated fat cells. *J. Biol. Chem.* 254, 3375-3381.
72. Rebois, R.V., Omedeo-Sale, F. and Fishman, P.H. (1981). Covalent crosslinking of human chorionic gonadotropin to its receptors in rat testes. *Proc. Natl. Acad. Sci. USA* 78, 2086-2089.
73. Caamano, C.A., Fernandez, H.N. and Paladani, A.C. (1983). Specificity of covalently stabilized complexes of $^{125}$I-labeled human somatotropin and components of the lactogenic binding sites of rat liver. *Biochem. Biophys. Res. Comm.* 115, 29-37.
74. Morgan, C.J. and Stanley, E.R. (1984). Chemical crosslinking of the mononuclear phagocyte specific growth factor CSF-1 to its receptor at the cell surface. *Biochem. Biophys. Res. Comm.* 119, 35-41.
75. Sen, I., Bull, H.G. and Sutter, R.L. (1984). Isolation of an angiotensin II binding protein from liver. *Proc. Natl. Acad. Sci. USA* 81, 1679-1683.
76. Wood, C.L. and O'Dorisio, M.S. (1985). Covalent crosslinking of vasoactive intestinal polypeptide to its receptors on intact human lymphoblasts. *J. Biol. Chem.* 260, 1243-1247.
77. Petruzelli, L., Herrer, R., Garcia-Arenas, R. and Rosen, R.M. (1985). Acquisition of insulin-dependent protein tyrosine kinase activity during *Drosophilia embryogenesis*. *J. Biol. Chem.* 226, 16072-16075.
78. Cox, G.W., Mattieson, B.J., Giardina, S.L. and Varesio, L. (1990). Characterization of IL-2 receptor expression and function on murine macrophages. *J. Immunol.* 145, 1719-1726.
79. Vandlen, R.L., Arcuri, K.E. and Napier, M.A. (1985). Identification of a receptor for atrial natriuretic factor in rabbit aorta membranes by affinity crosslinking. *J. Biol. Chem.* 260, 10889-10892.
80. Rashidbaigi, A., Langer, J.A., Jung, V., Jones, C., Morse, R.G., Tischfield, J.A., Trill, J.J., Kung, H.-F. and Pestka, S. (1986). The gene for the human immune interferon receptor is located on chromosome 6. *Proc. Natl. Acad. Sci. USA* 83, 384-388.
81. Tsudo, M., Kozak, R.W., Goldman, C.K. and Waldmann, T.A. (1986). Demonstration of a non-Tac peptide that binds interleukin 2: a potential participant in a multichain interleukin 2 receptor complex. *Proc. Natl. Acad. Sci. USA* 83, 9694-9698.
82. Kehrl, J.H., Taylor, A.S., Delsing, G.A., Roberts, A.B., Sporn, M.B. and Fauci, A.S. (1989). Further studies in the role of transforming growth factor-β in human B cell function. *J. Immunol.* 143, 1868-1874.
83. Helmesta, D.M., Hammonds, Jr., R.G. and Li, C.H. (1986). Preparation of [$^{125}$I-Tyr$^{27}$, Leu$^5$] βh-endorphin and its use for crosslinking of opioid binding sites in human striatum and NG108-15 neuroblastoma-glioma cells. *Proc. Natl. Acad. Sci. USA* 83, 4622-4625.
84. Wright, B.S., Tyler, G.A., O'Brien, R., Corporale, L.H. and Rosenblatt, M. (1987). Immunoprecipitation of the parathyroid hormone receptor. *Proc. Natl. Acad. Sci. USA* 84, 26-30.
85. Novick, D., Orchansky, P., Revel, M. and Rubenstein, M. (1987). The human interferon-γ receptor. *J. Biol. Chem.* 262, 8483-8487.
86. Staros, J.V. (1982). N-Hydroxysulfosuccinimide active esters: Bis(N-hydroxysuccinimide) esters of two dicarboxylic acids are hydrophilic, membrane impermeant, protein cross-linkers. *Biochem.* 21, 3950-3955.
87. Giedroc, D.P., Keravis, T.M., Staros, J.V., Ling, N., Wells, J.N. and Puett, D. (1985). Functional properties of covalent β-endorphin peptide/calmodulin complexes. Chlorpromazine binding and phosphodiesterase activation. *Biochem.* 24, 1203-1211.
88. Staros, J.V. and Kakkad, B.P. (1983). Crosslinking and chymotryptic digestion of the extracytoplasmic domain of the anion exchange channel in intact human erythrocytes. *J. Memb. Biol.* 74, 247-254.
89. Knoller, S., Shpungin, S. and Pick, E. (1991). The membrane-associated component of the amphiphile-activated, cytosol-dependent superoxide-forming NADPH oxidase of macrophages is identical to cytochrome b559. *J. Biol. Chem.* 266, 2795-2804.
90. Waugh, S.M., DiBella, E.E. and Pilch, P.F. (1989). Isolation of a proteolytically derived domain of the insulin receptor containing the major site of crosslinking/binding. *Biochem.* 28, 3448-3455.
91. Hordern, J.S., Leonard, J.D. and Scraba, D.G. (1979). Structure of the mengo virion. *Virol.* 97, 131-140.
92. dePont, J.J., Schoot, B.M. and Bonting, S.L. (1980). Use of mono- and bifunctional group-specific reagents in the study of the renal Na+-K+-ATPase. *Int. J. Biochem.* 12, 307-313.

Telephone: 800.874.3723 or 815.968.0747  Fax: 800.842.5007 or 815.968.7316
Internet: http://www.piercenet.com   E-mail: TA@piercenet.com

Pierce Chemical Technical Library cross-linking

93. Joshi, S. and Burrows, R. (1990). ATP synthase complex from bovine heart mitochondria. *J. Biol. Chem.* 265, 14518-14525.
94. Chelsky, D. and Dahlquist, F.W. (1980). Chemotaxis in Escherichia coli: Association of protein components. *Biochem.* 19, 4633-4639.
95. Kim, C.G. and Sheffrey, M. (1990). Physical characterization of the affinity purified CCAAT transcription α-CP1. *J. Biol. Chem.* 265, 13362-13369.
96. Baskin, L.S. and Yang, C.S. (1982). Crosslinking studies of the protein topography of rat liver microsomes. *Biochim. Biophys. Acta.* 684, 263-271.
97. Tarvers, R.C., Noyes, C.M., Roberts, H.R. and Lundblad, R.L. (1982). Influence of metal ions on prothrombin self-association. *J. Biol. Chem.* 257, 10708-10714.
98. Schweizer, E., Angst, W. and Lutz, H.V. (1982). Glycoprotein topology on intact human red blood cells reevaluated by cross-linking following amino group supplementation. *Biochem.* 21, 6807-6818.
99. Laburthe, M., Breant, B. and Rouyer-Fessard, C. (1984). Molecular identification of receptors for vasoactive intestinal peptide in rat intestinal epithelium by covalent crosslinking. *Eur. J. Biochem.* 139, 181-187.
100. Park, L.S., Friend, D., Gillis, S. and Urdal, D.L. (1986). Characterization of the cell surface receptor for a multi-lineage colony-stimulating factor (CSF-2a). *J. Biol. Chem.* 261, 205-210.
101. Hamada, H. and Tsuro, T. (1987). Determination of membrane antigens by a covalent crosslinking method with two monoclonal antibodies. *Anal. Biochem.* 160, 483-488.
102. Jung, S.M. and Moroi, M. (1983). Crosslinking of platelet glycoprotein Ib by N-succinimidyl(4-azidophenyldithio)propionate and 3,3'-dithiobis-(sulfosuccinimidyl propionate). *Biochim. Biophys. Acta* 761, 152-162.
103. Caufield, M.P., Horiuchi, S., Tai, P.C. and Davis, B.D. (1984). The 64-kilodalton membrane protein of *Bacillus subtilis* is also present as a multiprotein complex on membrane-free ribosomes. *Biochem.* 81, 7772-7776.
104. Abdella, R.M., Smith, P.K. and Royer, G.P. (1979). A new cleavable reagent for cross-linking and reversible immobilization of proteins. *Biochem. Biophys. Res. Comm.* 87, 734-742.
105. Baskin, L.S. and Yang, C.S. (1980). Cross-linking studies of cytochrome P-450 and reduced nicotinamide adenine nucleotide phosphate-cytochrome P-450 reductase. *Biochem.* 19, 2260-2264.
106. Browning, J. and Ribolini, A. (1989). Studies on the differing effects of tumor necrosis factor and lymphotoxin on the growth of several human tumor lines. *J. Immunol.* 143, 1859-1867.
107. Conn, P.M., Rogers, D.C., Stewart, J.M., Niedel, J. and Sheffield, T. (1982). Conversion of a gonadotropin-releasing hormone antagonist to an agonist. *Nature* 296, 633-655.
108. Conn, P.M., Rogers, D.C. and McNeil, R. (1982). Potency enhancement of a GnRh agonist: GnRh-receptor microaggregation stimulates gonadotropin release. *Endocrinology* 111, 335-337.
109. Millar, J.B. and Rozengur, E. (1990). Chronic desensitization to bombesin by progressive down-regulation of bombesin receptors in Swiss 3T3 cells. *J. Biol. Chem.* 265, 12052-12058.
110. Smith, R.J., Capaldi, R.A., Muchmore, D. and Dahlquist, F. (1978). Crosslinking of ubiquinone Cytochrome C reductase (complex III) with periodate-cleavable bifunctional reagents. *Biochem.* 17, 3719-3723.
111. Bragg, P.D. and Hou, C. (1980). A crosslinking study of the $Ca^{2+}$, $Mg^{2+}$-activated adenosine triphosphate of *Escherichia coli*. *Eur. J. Biochem.* 106, 495-503.
112. Farries, T.C. and Atkinson, J.P. (1989). Biosynthesis of properdin. *J. Immunol.* 142, 842-847.
113. Zarling, D.A., Watson, A. and Bach, F.H. (1980). Mapping of lymphocyte surface polypeptide antigens by chemical crosslinking with BSOCOES. *J. Immunol.* 124, 913-920.
114. Howard, A., de La Baume, S., Gioannini, T.L. and Hiller, J.M. (1985). Covalent labeling of opioid receptors with human β-endorphin. *J. Biol. Chem.* 260, 10833-10839.
115. Bouizar, Z., Fouchereau-Person, M., Taboulet, J., Moukhtar, M.S. and Milhaud, G. (1986). Purification and characterization of calcitonin receptors in rat kidney membranes by covalent cross-linking techniques. *Eur. J. Biochem.* 155, 141-147.
116. Ishikawa, E., Imagawa, M. and Hashida, S. (1983). Ultra sensitive enzyme immunoassay using fluorogenic, luminogenic, radioactive and related substances and factors to limit the sensitivity. *Proceedings 2nd Internat. Sym. Immunoenzymatic Tech.*

Pierce Chemical Technical Library cross-linking

117. Yoshitake, S., Imagawa, M., Ishikawa, E., Niitsu, Y., Urushizaki, I., Nishiura, M., Kanazawa, R., Kurosaki, H., Tachibana, S., Nakazawa, N. and Ogawa, H. (1982). Mild and efficient conjugation of rabbit Fab' and horseradish peroxidase using a maleimide compound and its use for enzyme immunoassay. *J. Biochem.* 92, 1413-1424.

118. Yoshitake, S., Imagawa, M. and Ishikawa, E. (1982). Efficient preparation of rabbit Fab'-horseradish peroxidase conjugates using maleimide compounds and its use for enzyme immunoassay. *Anal. Lett.* 15(B2), 147-160.

119. Imagawa, M., Yoshitake, S., Hamaguchi, Y., Ishikawa, E., Niitsu, Y., Urushizaki, I., Kanazawa, R., Tachibana, S., Nakazawa, N. and Ogawa, H. (1982). Characteristics and evaluation of antibody-horseradish peroxidase conjugates prepared by using a maleimide compound, glutaraldehyde, and periodate. *J. Appl. Biochem.* 4, 41-57.

120. Freytag, J.W., Lau, H.P. and Wadsley, J.J. (1984) Affinity-column-mediated immunoenzymometric assays: influence of affinity-column ligand and valency of antibody-enzyme conjugates. *Clin. Chem.* 30(9), 1494-1498.

121. Hashida, S. and Ishikawa, E. (1985). Use of normal IgG and its fragments to lower the nonspecific binding of Fab'-enzyme conjugates in sandwich enzyme immunoassay. *Anal. Lett.* 18(B9), 1143-1155.

122. Mahan, D.E., Morrison, L., Watson, L. and Haugneland, L.S. (1987). Phase change enzyme immunoassay. *Anal. Biochem.* 162, 163-170.

123. Dewey, R.E., Timothy, D.H. and Levings III, C.S. (1987). A mitochondrial protein associated with cytoplasmic male sterility in the T cytoplasm of maize. *Proc. Natl. Acad. Sci. USA* 84, 5374-5378.

124. Peeters, J.M., Hazendonk, T.G., Beuvery, E.C. and Tesser, G.I. (1989). Comparison of four bifunctional reagents for coupling peptides to proteins and the effect of the three moieties on the immunogenicity of the conjugates. *J. Immunol. Meth.* 120, 133-143.

125. Uto, I., Ishimatsu, T., Hirayama, H., Ueda, S., Tsuruta, J. and Kambara, T. (1991). Determination of urinary Tamm-Horsfall protein by ELISA using a maleimide method for enzyme-antibody conjugation. *J. Immunol. Meth.* 138, 87-94.

126. Hashida, S., Imagawa, M., Inoue, S., Ruan, K.-H. and Ishikawa, E. (1984). More useful maleimide compounds for the conjugation of Fab' to horseradish peroxidase through thiol groups in the hinge. *J. Applied Biochem.* 6, 56-63.

127. Samoszuk, M.K., Petersen, A., Lo-Hsueh, M. and Rietveld, C. (1989). A peroxide-generating immunoconjugate directed to eosinophil peroxidase is cytotoxic to Hodgkin's disease cells in vitro. *Antibody Immunocon. Radiopharm.* 2(1), 37-46.

128. Kitagawa, T. and Aikawa, T. (1976). Enzyme coupled immunoassay of insulin using a novel coupling reagent. *J. Biochem.* 79, 233-236.

129. Liu, F.-T., Zinnecker, M., Hamaoka, T. and Katz, D.H. (1979). New procedures for preparation and isolation of conjugates of proteins and a synthetic copolymer of D-amino acids and immunochemical characterization of such conjugates. *Biochem.* 18, 690-697.

130. O'Sullivan, M.J., Gnemmi, E., Morris, D., Chieregatti, G., Simmonds, A.D., Simmons, M., Bridges, J.W. and Marks, V. (1979). Comparison of two methods of preparing enzyme-antibody conjugates: application of these conjugates for enzyme immunoassay. *Anal. Biochem.* 100, 100-108.

131. Youle, R.J. and Nevelle, Jr., D.M. (1980). Anti-Thy 1.2 monoclonal antibody linked to ricin is a potent cell-type-specific toxin. *PNAS* 77(9), 5483-5486.

132. Lerner, R.A., Green, N., Alexander, H., Liu, F.-T., Sutcliffe, J.G. and Shinnick, T.M. (1981). Chemically synthesized peptides predicted from the nucleotide sequence of the hepatitis B virus genome elicit antibodies reactive with the native envelope protein of Dane particles. *Proc. Natl. Acad. Sci. USA* 78(6), 3403-3407.

133. Kitagawa, T., Kawasaki, T. and Munechika, H. (1982). *J. Biochem.* 92, 585-590.

134. Freytag, J.W., Dickinson, J.C. and Tseng, S.Y. (1984). A highly sensitive affinity-column-mediated immunometric assay, as exemplified by digoxin. *Clin. Chem.* 30(3), 417-420.

135. Niman, H.L., Thompson, A.M.H., Yu, A., Markman, M., Willems, J.J., Herwig, K.R., Habib, N.A., Wood, C.B., Houghten, R.A. and Lerner, R.A. (1985). Anti-peptide antibodies detect oncogene-related proteins in urine. *Proc. Natl. Acad. Sci. USA* 82, 7924-7928.

136. Dell'Arciprete, L., Colombatti, M., Rappuoli, R. and Tridente, G. (1988). A C terminus cysteine of diphtheria toxin B chain involved in immunotoxin cell penetration and cytotoxicity. *J. Immunol.* 140, 2466-2471.

137. Chamberlain, N.R., DeOgny, L., Slaughter, C., Radolf, J.D. and Norgard, M.V. (1989). Acylation of the 47-kilodalton major membrane immunogen of *Treponema pallidum* determines its hydrophobicity. *Infection Immunity* 57(9), 2878-2885.

138. Edwards, R.J., Singleton, A.M., Boobis, A.R. and Davies, D.S. (1989). Cross-reaction of antibodies to coupling groups used in the production of anti-peptide antibodies. *J. Immunol. Meth.* 117, 215-220.

139. Kitagawa, T., Fujitake, T., Taniyama, H. and Aikawa, T. (1978). Enzyme immunoassay of viomycin. *J. Biochem.* 83, 1493-1501.

Pierce Chemical Technical Library cross-linking

140. Miller, M.D., Hata, S., De Waal Malefyt, R. and Krangel, M.S. (1989). A novel polypeptide secreted by activated human T lymphocytes. *J. Immunol.* 143(9), 2907-2916.

141. Swanson, S.J., Lin, B.-F., Mullenix, M.C. and Mortensen, R.F. (1991). A synthetic peptide corresponding to the phosphorylcholine (PC)-binding region of human C-reactive protein possesses the TEPC-15 myeloma PC-idiotype. *J. Immunol.* 146(5), 1596-1601.

142. Myers, D.E., Uckun, F.M., Swaim, S.E. and Vallera, D.A. (1989). The effects of aromatic and aliphatic maleimide crosslinkers on anti-CD5 ricin immunotoxins. *J. Immunol. Meth.* 121, 129-142.

143. Aithal, H.N., Knigge, K.M., Kartha, S., Czyewski, E.A. and Toback, F.G. (1988). An alternate method utilizing small quantities of ligand for affinity purification of monospecific antibodies. *J. Immunol. Meth.* 112, 63-70.

144. Martin, F.J. and Papahadjopoulos, D. (1982). Irreversible coupling of immunoglobulin fragments to preformed vesicles. *J. Biol. Chem.* 257, 286-288.

145. Gitman, A.G., Kahane, I. and Loyter, A. (1985). Use of virus-attached antibodies or insulin molecules to mediate fusion between Sendai virus envelopes and neuraminidase-treated cells. *Biochem.* 24, 2762-2768.

146. Gitman, A.G., Graessmann, A. and Loyter, A. (1985). Targeting of loaded Sendai virus envelopes by covalently attached insulin molecules to virus receptor-depleted cells: fusion-mediated microinjection of ricin A and simian virus 40 DNA. *Proc. Natl. Acad. Sci. USA* 82, 7309-7313.

147. Teale, J.M. and Kearney, J.F. (1986). Clonotypic analysis of the fetal B cell repertoire: evidence for an early and predominant expression of idiotypes associated with the VH 36-60 family. *J. Mol. Cell. Immunol.* 2, 283-292.

148. Iwai, K., Fukuoka, S.-I., Fushiki, T., Kido, K., Sengoku, Y. and Semba, T. (1988). Preparation of a verifiable peptide-protein immunogen: direction-controlled conjugation of a synthetic fragment of the monitor peptide with myoglobin and application for sequence analysis. *Anal. Biochem.* 171, 277-282.

149. Bangs, J.D., Andrews, N.W., Hart, G.W. and Englund, P.T. (1986). Post-translational modification and intracellular transport of a typanosome variant surface glycoprotein. *J. Cell. Biol.* 103, 255-263.

150. Yi, F., Denker, B.M. and Neer, E.J. (1991). Structural and functional studies of cross-linked Go protein subunits. *J. Biol. Chem.* 266(6), 3900-3906.

151. Pepinsky, R.B., Chen, L.L., Meier, W. and Wallner, B.P. (1991). The increased potency of cross-linked lymphocyte function-associated antigen-3 (LFA-3) multimers is a direct consequence of changes in valency. *J. Biol. Chem.* 266(27), 18244-18249.

152. Chen, L.L., Rosa, J.J., Turner, S. and Pepinsky, R.B. (1991). Production of multimeric forms of CD4 through a sugar-based cross-linking strategy. *J. Biol. Chem.* 266(27), 18237-18243.

153. Fujiwara, K., Matsumoto, N., Yagisawa, S., Tanimori, H., Kitagawa, T., Hirota, M., Hiratani, K., Fukushima, K., Tomonaga, A., Hara, K. and Yamamoto, K. (1988). Sandwich enzyme immunoassay of tumor-associated antigen sialosylated Lewis$^a$ using ß-D-galactosidase coupled to a monoclonal antibody of IgM isotype. *J. Immunol. Meth.* 112, 77-83.

154. Tanimori, H., Kitagawa, T., Tsunoda, R. and Tsuchiya, R.J. (1981). *Pham. Dyn.* 4, 812.

155. Kitagawa, J., et. al. (1981). *Chem. Pham. Bull.* 28, 1130.

168. O'Shannessy, D.J. and Quarles, R.H. (1985). Specific conjugation reactions of the oligosaccharide moieties of immunoglobulins. *J. Applied Biochem.* 7, 347-355.

169. Lewis, R.V., Roberts, M.F., Dennis, E.A. and Allison, W.S. (1977). Photoactivated heterobifunctional cross-linking reagents which demonstrate the aggregation state of Phospholipase A2. *Biochem.* 16(25), 5650-5654.

170. Krieg, U.C., Walter, P. and Johnson, A.E. (1986). Photocrosslinking of the signal sequence of nascent preprolactin to the 54-kilodalton polypeptide of the signal recognition particle. *Proc. Natl. Acad. Sci. USA* 83, 8604-8608.

171. Traut, R.R., et. al. (1989). Protein Function, A Practical Approach. Oxford: IRL Press, p. 101.

172. Ngo, T.T., et. al. (1981). *J. Biol. Chem.* 256, 11313-11318.

173. Politz, S.M., Noller, H.F. and McWhirter, P.D. (1981). *Biochem.* 20, 372-378.

174. Sgro, J., Jacrot, B. and Chroboczek, J. (1986). *Eur. J. Biochem.* 154, 69-76.

175. Galardy, R.E., Craig, L.C., Jamieson, J.D. and Printz, M.P. (1974). Photoaffinity labeling of peptide hormone binding sites. *J. Biol. Chem.* 249(11), 3510-3518.

176. Yeung, C.W.T., Moule, M.L. and Yip, C.C. (1980). Photoaffinity labeling of insulin receptor with an insulin analogue selectively modified at the amino terminal of the B chain. *Biochem.* 19, 2196-2203.

Pierce Chemical Technical Library cross-linking

177. Massague, J., et. al. (1981). *J. Biol. Chem.* 256, 9419-9424.
178. Ji, I. and Ji, T.H. (1981). Both α and β subunits of human choriogo-nadotropin photoaffinity label the hormone receptor. *Proc. Natl. Acad. Sci. USA* 78(9), 5465-5469.
179. Ballmer-Hofer, K., Schlup, V., Burn, P. and Burger, M.M. (1982). Isolation of *in situ* crosslinked ligand-receptor complexes using an anticrosslinker specific antibody. *Anal. Biochem.* 126, 246-250.
180. Ji, T.H. and Ji, I. (1982). Macromolecular photoaffinity labeling with radioactive photoactivable heterobifunctional reagents. *Anal. Biochem.* 121, 286-289.
181. Ji, I., Shin, J. and Ji, T.H. (1985). Radioiodination of a photoactivatable heterobifunctional reagent. *Anal. Biochem.* 151, 348-349.
182. Shanahan, M.F., Wadzinski, B.E., Lowndes, J.M. and Ruoho, A.E. (1985). Photoaffinity labeling of the human erythrocyte monosaccharide transporter with an aryl azide derivative of D-Glucose. *J. Biol. Chem.* 260(20), 10897-10900.
183. van der Horst, G.T.J., Mancini, G.M.S., Brossmer, R., Rose, U. and Verheijen, F.W. (1990). Photoaffinity labeling of a bacterial sialidase with an aryl azide derivative of sialic acid. *J. Biol. Chem.* 265(19), 10801-10804.
184. Pascual, A., Casanova, J. and Samuels, H.H. (1982). Photoaffinity labeling of thyroid hormone nuclear receptors in intact cells. *J. Biol. Chem.* 257(16), 9640-9647.
185. Casanova, J., Horowitz, Z.D., Copp, R.P., McIntyre, W.R., Pascual, A. and Samuels, H.H. (1984). Photoaffinity labeling of thyroid hormone nuclear receptors. *J. Biol. Chem.* 259(19), 12084-12091.
186. Baenziger, J.U. and Fiete, D. (1982). Photoactivatable glycopeptide reagents for site-specific labeling of lectins. *J. Biol. Chem.* 257(8), 4421-4425.
187. Zarling, D.A., Miskimen, J.A., Fan, D.P., Fujimoto, E.K. and Smith, P.K. (1982). Association of sendai virion envelope and a mouse surface membrane polypeptide on newly infected cells: lack of association with H-2K/D or alteration of viral immunogenicity. *J. Immunol.* 128(1), 251-257.
188. Vanin, E.F. and Ji, T.H. (1981). Synthesis and application of cleavable photoactivatable heterobifunctional reagents. *Biochem.* 20, 6754-6760.
189. Thevinin, B.J.-M., Shahrokh, Z., Williard, R.L., Fujimoto, E.K., Kang, J.-J., Ikemoto, N. and Shohet, S.B. (1992). A novel photoactivatable cross-linker for the functionally-directed region-specific fluorescent labeling of proteins. *Eur. J. Biochem.* 206, 471-477.
190. Kang, J.J., Tarcsafalvi, A., Carlos, A.D., Fujimoto, E., Shahrokh, Z., Thevenin, B.J.M., Shohet, S.B. and Ikemoto, N. (1992). Conformational changes in the foot protein of the sarcoplasmic reticulum assessed by site-directed fluorescent labeling. *Biochem.* 31, 3288-3293.
191. Schmitt, M., Painter, R.G., Jesaitis, A.J., Preissner, K., Sklar, L.A. and Cochrane, C.G. (1983). Photoaffinity labeling of the N-formyl peptide receptor binding site of intact human polymorphonuclear leukocytes. *J. Biol. Chem.* 258(1), 649-654.
192. Wollenweber, H.-W. and Morrison, D.C. (1985). Synthesis and biochemical characterization of a photoactivatable, iodinatable, cleavable bacterial l ipopolysaccharide derivative. *J. Biol. Chem.* 260(28), 15068-15074.
193. Sorensen, P., Farber, N.M. and Krystal, G. (1986). Identification of the interleukin-3 receptor using an iodinatable, cleavable, photoreactive crosslinking agent. *J. Biol. Chem.* 261, 9094-9097.
194. Shephard, E.G., DeBeer, F.C., von Holt, C. and Hapgood, J.P. (1988). The use of sulfosuccinimidyl-2-(p-azidosalicylamido)-1,3'-dithiopropionate as a crosslinking reagent to identify cell surface receptors. *Anal. Biochem.* 168, 306-313.
195. Chattopadhyay, A., James, H.L. and Fair, D.S. (1992). Molecular recognition sites on factor Xa which participate in the prothrombinase complex. *J. Biol. Chem.* 267(17), 12323-12329.

cross-linking

Pierce Chemical Technical Library

Subunit Cross-linking and Protein Structural Studies

Cross-linkers can be used to study the structure and composition of proteins in biological samples. Some proteins are difficult to study because they exist in different conformations under varying pH or salt conditions. One way to avoid conformational changes is to cross-link the subunits together. Amine-, carboxyl- or sulfhydryl-reactive reagents are employed for identification of particular amino acids or for the determination of the number, location and size of subunits in a protein. Short-to-medium spacer arm cross-linkers are selected when intramolecular cross-linking is performed. If the spacer arm is too long, intermolecular cross-linking can occur. Carbodiimides that result in no spacer arm, along with short length conjugating reagents, such as amine-reactive DFDNB (Product #21524, Table 10) or the photoactivatable amine-reactive cross-linker NHS-ASA (Product #27715), can cross-link between subunits without cross-linking to extraneous molecules if used in optimal concentrations and conditions. Slightly longer cross-linkers such as DMP (Product #20666), DMS (Product #20668), DTBP (Product #20665), DSS (Product #21555) or DSP (Product #22585) can also cross-link between subunits, but they may result in intermolecular coupling. Intermolecular cross-linking can be controlled by adjusting the amount of cross-linker and the concentration of the material to be cross-linked. Dilute protein solutions and high concentrations of cross-linker favor intramolecular cross-linking when homobifunctional cross-linkers are employed. BMH (Product #22319) and other non-cleavable, homobifunctional, sulfhydryl-reactive linkers can be used to link subunits of proteins that were joined by disulfide bonds. After reduction of the disulfides, and by cross-linking through the generated sulfhydryls, the protein will run as its full molecular mass using polyacrylamide gel electrophoresis and reducing conditions. In some circumstances, the cross-linking pattern or success may be affected by the cross-linker's solubility. Hydrophobic cross-linkers tend to cross-link more effectively in hydrophobic regions of molecules.

If the three-dimensional structure of a protein is to be determined or confirmed, cleavable cross-linkers with increasing spacer arm lengths can be used to determine the distance between two subunits. Experiments using cross-linkers with different reactive groups may indicate the locations of specific amino acids. Once conjugated, the proteins are subjected to two-dimensional electrophoresis. In the first dimension, the proteins are run under non-reducing conditions. The molecular weight of the non-reducing sample is recorded. It should be noted that some of the subunits may not be cross-linked and will run according to their individual molecular weights. Other subunits will be combined and, under nonreducing conditions, will run according to the combined molecular weight. The second dimension of the gel is then run using conditions to cleave the cross-linked subunits. The individual molecular weights of the cross-linked subunits can be determined. If the cross-linked subunits were not reduced, the pattern of the second dimension would be a diagonal. However, with the cleavable cross-linker, the cross-linked subunits will be released under reducing conditions, and the individual molecular weights of the subunits will be approximated. The cleaved subunits will be off the diagonal. The molecular weights of the individual subunits should be compared with pre-determined molecular weights of the protein subunits under reducing SDS-polyacrylamide gel electrophoresis.

Telephone: 800.874.3723 or 815.968.0747  Fax: 800.842.5007 or 815.968.7316
Internet: http://www.piercenet.com  E-mail: TA@piercenet.com

Pierce Chemical Technical Library cross-linking

Table 10: Bifunctional Aryl Halide

| Cross-Linker | Product # | M.W. | Spacer Arm Length | Reactivity | Applications/References |
|---|---|---|---|---|---|
| DFDNB<br>1,5-Difluoro-2,4-dinitrobenzene | 21524 | 204.1 | 3 Å | • Aryl halide-amine and sulfhydryl-reactive | • Cross-linking phospholipids in human erythrocyte membranes[196]<br>• Coupling peptides to albumin[197]<br>• Studies of near neighbor relationships of proteins in the myelin membrane[198]<br>• Cross-linking cytochrome oxidase subunits[199] |

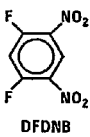

DFDNB

References

196. Marfey, S.P. and Tsai, K.H. (1975). Cross-linking of phospholipids in human erythrocyte membrane. *Biochem. Biophys. Res. Comm.* 65(1), 31-38.
197. Tager, H.S. (1976). Coupling of peptides to albumin with Difluorodini-trobenzene. *Anal. Biochem.* 71, 367-375.
198. Golds, E.E. and Braun, P.E. (1978). Protein associations and basic protein conformation in the myelin membrane. *J. Biol. Chem.* 253(22), 8162-8170.
199. Kornblatt, J.A. and Lake, D.F. (1980). Cross-linking of cytochrome oxidase subunits with difluorodinitrobenzene. *Can. J. Biochem.* 58, 219-224.

Pierce Chemical Technical Library cross-linking

Intermolecular Cross-linking for the Study of Protein Interactions and Associations Cross-linkers are widely used for identification of near-neighbor protein relationships, ligand-receptor identification and interactions, and enzyme-substrate orientations. The cross-linkers chosen for these applications are usually longer than those used for subunit cross-linking. Homobifunctional, amine-reactive NHS-esters or imidates and heterobifunctional, amine-reactive, photoactivatable phenyl azides are the most commonly-used cross-linkers for these procedures. Occasionally, a sulfhydryl- and amine-reactive cross-linker such as Sulfo-SMCC (Product #'s 22522, 22322) may be employed if one of the two proteins or molecules is known to contain sulfhydryls. Cleavable or noncleavable cross-linkers are typically used. Because the distances between two molecules are not always known, the optimum length of the spacer arm of the cross-linker may be determined by the use of a panel of similar cross-linkers with different lengths. DSS (Product #21555) or its cleavable analog DSP (Product #22585) are among the shorter cross-linkers used for protein-protein associations. NHS-ester, phenyl azides are very useful for this type of cross-linking because they usually result in some successful, if not efficient, cross-linking. SASD (Product #27716) is a unique sulfo-NHS-ester, photoactivatable phenylazide that is iodinatable and cleavable. Its characteristics allow for detection and analysis of small quantities of protein.

Cross-linkers can be used to determine whether a particular protein is located on the surface or the integral part of the membrane. These studies are possible because water-soluble cross-linkers are membrane-impermeable, while water-insoluble cross-linkers are membrane-permeable. The experiment can be carried out by performing a conjugation reaction of a particular cell membrane preparation to a known protein or radioactive label in the presence of water-soluble or water-insoluble cross-linkers. Upon conjugation the cells may be washed, solubilized and characterized by SDS-PAGE. The gel electrophoresis results can be used to determine whether the protein of interest was conjugated. Any integral membrane protein will conjugate in the presence of a water-insoluble cross-linker, but not in the presence of water-soluble cross-linkers. Surface membrane proteins should conjugate in the presence of both water-soluble and water-insoluble cross-linkers.

BASED (Product #21564), a homobifunctional photoactivatable phenyl azide, is one of the more versatile cross-linkers for the study of protein interactions and associations. It is cleavable and can be radiolabeled with $^{125}$I using IODO-BEADS® Iodination Reagent (Product #28665). After cleavage, both of the dissociated molecules will still be iodinated. Because both reactive groups on this cross-linker are nonspecific, the cross-linking is not dependent on amino acid composition for successful conjugation.

SDBP (Product #22340) is a cross-linker that is amine-reactive at both ends, but contains two different reactive groups with varying reactivity. Please see Table 11 for more information on SDBP. The reaction is controlled by temperature. SDBP is an NHS-ester with amine reactivity that is only slightly affected by temperature; however, its second amine-reactive functional group is a dibromoacetyl group that is slow to react with amines at physiological pH at 4°C. This cross-linker can be useful for studying conformational changes in proteins.

Telephone: 800.874.3723 or 815.968.0747  Fax: 800.842.5007 or 815.968.7316
Internet: http://www.piercenet.com  E-mail: TA@piercenet.com

Pierce Chemical Technical Library cross-linking

Table 11: Heterobifunctional Amine-Reactive Cross-linker

| CROSS-LINKER | PRODUCT # | M.W. | SPACER ARM LENGTH | REACTIVITY | APPLICATIONS/REFERENCES |
|---|---|---|---|---|---|
| SDBP<br>N-Hydroxysuccin-<br>imidyl 2,3-Dibromopropionate | 22340 | 328.96 | 5.0 Å | • NHS-ester<br>• Alkyl dibromide | • Preparation of immunotoxins[200] |

SDBP
M.W. 328.96
Spacer Arm 5.0 Å

References

200. McKenzie, J.A., Raison, R.L. and Rivett, E.E. (1988). Development of a bifunctional crosslinking agent with potential for the preparation of immunotoxins. *J. Protein Chem.* 7(5), 581-592.

Pierce Chemical Technical Library cross-linking

Cell Membrane Structural Studies

Cell membrane structural studies require reagents of varying hydrophobicity to determine the location and the environment within a cell's lipid bilayer. Fluorescent tags are used to locate proteins, lipids or other molecules inside and outside the membrane. Various cross-linkers with differing spacer arm lengths can be used to cross-link proteins to associated molecules within the membrane to determine the distance between molecules. Successful cross-linking with shorter cross-linkers is a strong indication that two molecules are interacting in some manner. Failure to obtain cross-linking with a panel of shorter cross-linkers, while obtaining conjugation with the use of longer reagents, generally indicates that the molecules are located in the same part of the membrane but are not interacting. Homobifunctional NHS-esters, imidates or heterobifunctional NHS-ester, photoactivatable, phenyl azides are commonly used for these procedures. Because they are membrane impermeant, sulfo-NHS-esters are not useful for cross-linking within the membrane. Imidoester cross-linkers (imidates) are water-soluble, but they are still able to penetrate membranes. DTBP (Product #20665) is an amine-reactive imidoester that is cleavable by sulfhydryls. Sulfhydryl-reactive cross-linkers may be useful for targeting molecules with cysteines to other molecules within the membrane.

EDC (Product #'s 22980, 22981), water insoluble dicyclohexylcarbodiimide, or DCC (Product #20320), and other water-soluble and water-insoluble coupling reagents are used to study membranes and cellular structure,[52,53] protein subunit structure and arrangement,[54,55] enzyme-substrate interactions,[56-58] and cell surface[59] and membrane receptors.[60,61] The hydrophilic character of EDC can result in much different cross-linking patterns in membrane and subunit studies than with hydrophobic carbodiimides such as DCC.[52,55] Often it is best to attempt cross-linking with a water-soluble and water-insoluble carbodiimide to obtain a complete picture of the spacial arrangements or protein-protein interactions involved.

References

52. Buisson, M. and Reboud, A.M. (1982). Carbodiimide-induced protein-RNA crosslinking in mammalian ribosomal subunits. *FEBS Lett.* 148(2), 247-250.
53. Zurrer, H., Snozzi, M. and Bachofen, R. (1983). Specific binding of DCCD to reaction centers of the photosynthetic bacterium *Rhodospirillum rubrum* and its effect of certain photosynthetic reactions. *FEBS Lett.* 153(1), 151-155.
54. Lotscher, H.-R., deJong, C. and Capaldi, R. (1984). Inhibition of the adenosinetriphosphatase activity of *Escherichia coli* F1 by the water-soluble carbodiimide 1-ethyl-3-[3-(dimethylamino)propyl]carbodiimide is due to modification of several carboxyls in the B subunit. *Biochem.* 23(18), 4134-4140.
55. Lotscher, H.-R. and Capaldi, R.A. (1984). Structural asymmetry of the F1 of *Escherichia coli* as indicated by reaction with dicyclohexylcarbodi-imide. *Biochem. Biophys. Res. Comm.* 121(1), 331-339.
56. Yamada, H., Imoto, T., Fujita, K., Okazaki, K and Motomura, M. (1981). Selective modification of aspartic acid-101 in lysozyme by carbodiimide reaction. *Biochem.* 20, 4836-4842.
57. Davidson, V.L., Jones, L.H. and Kumar, M.A. (1990). pH-dependent semiquinone formation by methylamine dehydrogenase from *Parcoccus denitriicans*. Evidence for intermolecular electron transfer between quinone cofactors. *Biochem.* 29, 10786-10791.
58. Gutweniger, H.E., Grassi, C. and Bisson, R. (1983). Interaction between Cytochrome C and ubiquinone-Cytochrome C oxidoreductase: a study with water-soluble carbodiimides. *Biochem. Biophys. Res. Comm.* 116(1), 272-283.
59. Grob, P.M., Berlot, C. and Bothwell, M.A. (1983). Affinity labeling and partial purification of nerve growth factor receptors from rat pheochromocytoma and human melanoma cells. *Proc. Natl. Acad. Sci. USA* 80, 6819-6823.
60. Taniuchi, M., Schweitzer, J.B. and Johnson Jr., E.M. (1986). Nerve growth factor receptor molecules in rat brain. *Proc. Natl. Acad. Sci. USA* 83, 1950-1954.
61. Taniuchi, M., Clark, H.B. and Johnson, Jr., E.M. (1986). Induction of nerve growth factor receptor in Schwann cells after axotomy. *Proc. Natl. Acad. Sci. USA* 83, 4094-4098.

Telephone: 800.874.3723 or 815.968.0747   Fax: 800.842.5007 or 815.968.7316
Internet: http://www.piercenet.com   E-mail: TA@piercenet.com

Pierce Chemical Technical Library cross-linking

Immunotoxins

Specific antibodies can be covalently linked to toxic molecules and then used to target antigens on cells. Often these antibodies are specific for tumor associated antigens. Immunotoxins are brought into the cell by surface antigens and, once internalized, they proceed to kill the cell by ribosome inactivation or other means. The type of cross-linker used to make an immunotoxin can affect its ability to locate and kill the appropriate cells. For immunotoxins to be effective, the conjugate must be stable in vivo. In addition, once the immunotoxin reaches its target, it is important that the antibody be separable from the toxin to allow the toxin to kill the cell. Thiol-cleavable, disulfide-containing conjugates have been shown to be more cytotoxic to tumor cells than noncleavable conjugates of ricin A immunotoxins. Cells are able to break the disulfide bond in the cross-linker, allowing the release of the toxin within the targeted cell.

SPDP (Product #'s 21757, 21657, 21557) is a reversible NHS-ester, pyridyl disulfide cross-linker used to conjugate amine-containing molecules to sulfhydryls. For several years, this has been the "workhorse" cross-linker for production of immunotoxins. The amine-reactive NHS-ester is usually reacted first with the antibody. In general, toxins do not contain surface sulfhydryls; therefore, sulfhydryls must be introduced onto them by reduction of disulfides, which is common for procedures involving ricin A chain and abrin A chain, or through chemical modification reagents. A second SPDP molecule can be used for this purpose. It is reacted with amines on the immunotoxin, then reduced to yield sulfhydryls. Another chemical modification reagent that is commonly used for production of immunotoxins is 2-iminothiolane, also known as Traut's Reagent (Product #26101). Traut's Reagent reacts with amines and yields a sulfhydryl when its ring structure opens during the reaction.

Other water-soluble SPDP analogs, such as Sulfo-LC-SPDP (Product #'s 21650, 21649), are available for immunotoxin production, allowing for ease of use or avoidance of organic solvents. In addition, Sulfo-LC-SPDP and LC-SPDP (Product #'s 21651, 21652) have longer spacer arms and can offer better conjugation efficiency.

SMPT (Product #21558) is a reversible, NHS-ester, pyridyl disulfide cross-linker developed to provide increased stability of immunotoxins *in vivo*. The disulfide bond in SMPT is protected, making it less likely to be cleaved *in vivo* prior to reaching the antigenic target. In addition, the NHS-ester of SMPT is much more stable in aqueous solution than typical NHS-ester compounds, showing little degradation even after several hours in aqueous solution. A water-soluble long chain version of SMPT is also offered—Sulfo-LC-SMPT (Product #'s 21569, 21568).

Pierce Chemical Technical Library cross-linking

Carrier Protein Hapten/Peptide/Polypeptide Conjugates for Use as Immunogens

Pierce offers many products in this area of immunological research. Easy-to-use kits are available for coupling ligands using several different chemistries. These kits and the use of immunogens are discussed in the Antibody Production Technical Section of this catalog. There are many cross-linkers used for the production of these conjugates, and the best choice is dependent on the reactive groups present on the hapten and the ability of the hapten-carrier conjugate to function successfully as an immunogen after its injection. Carbodiimides are good choices for producing peptide carrier conjugates because both proteins and peptides usually contain several carboxyls and primary amines. Carbodiimides such as EDC (Product #'s 22980, 22981) react with carboxyls first to yield highly reactive unstable intermediates. The intermediates can then couple to primary amines. Many different carboxyl- or amine-containing small molecules can be attached to carrier proteins using this easy-to-use chemistry.

Other heterobifunctional cross-linkers can also be used to make immunogen conjugates. Often peptides are synthesized with terminal cysteines to allow for their attachment to supports or to carrier proteins through a part of the molecule that is not important for activity or recognition. Sulfhydryl-reactive, heterobifunctional cross-linkers can be coupled to carrier proteins through their other functional group and then can be linked to peptides through terminal cysteines. This method can be very efficient and yield an immunogen that is capable of eliciting a good response upon injection. A good choice of cross-linker with these characteristics is Pierce's Sulfo-SMCC (Product #22322). This cross-linker is an amine-reactive NHS-ester that contains a cyclohexyl group in its spacer and a very stable maleimide group at the other end of the molecule. The maleimide of Sulfo-SMCC is more stable than the maleimide on other NHS-ester maleimide cross-linkers because of the stability imparted by the cyclohexyl ring. Pierce uses Sulfo-SMCC to produce its entire selection of Maleimide Activated Carrier Proteins and Kits. Please see the Antibody Production Technical Section for additional information. Other cross-linkers that can be used to make immunogens are MBS (Product #'s 22510, 22310), SMPB (Product #'s 22316, 22315) and GMBS (Product #22314). Water-soluble analogs are also available, including Sulfo-MBS (Product #'s 22313, 22312), Sulfo-SMPB (Product #'s 22318, 22317) and Sulfo-GMBS (Product #22324).

SDBP (Product #22340) is a cross-linker that is amine-reactive at both ends, but contains two different reactive groups with varying reactivity. The reaction is controlled by temperature. SDBP is an NHS-ester with amine reactivity that is only slightly affected by temperature; however, its second amine-reactive functional group is a dibromoacetyl group, which is slow to react with amines at physiological pH at 4°C. A possible application for this cross-linker is to allow the NHS group to react with amines on the carrier protein. After quick removal of the excess cross-linker from the carrier protein, an amine-containing hapten can be added to the solution, and the reaction can be allowed to warm to room temperature, then proceed for several hours.

Telephone: 800.874.3723 or 815.968.0747   Fax: 800.842.5007 or 815.968.7316
Internet: http://www.piercenet.com   E-mail: TA@piercenet.com

Pierce Chemical Technical Library cross-linking

Solid-Phase Immobilization

Proteins, peptides and other molecules can be immobilized on solid-phase matrices for use as affinity supports or for sample analysis. The matrices may be agarose, beaded polymers, polystyrene plates or balls, porous glass or glass slides, and nitrocellulose or other membrane materials. Some supports can be activated for direct coupling to a ligand. Other supports are made with nucleophiles or other functional groups that can be linked to proteins or other ligands using cross-linkers. Carbodiimides such as DCC (Product #20320) and EDC (Product #'s 22980, 22981) are very useful for coupling proteins to carboxy- and amine-activated glass, plastic and agarose supports. Carbodiimide procedures are usually one-step methods; however, two-step methods are possible if reactions are performed in organic solvents, or if NHS (Product #24500) or Sulfo-NHS (Product #24510) are used to enhance the reaction.

EDC is useful for coupling ligands to solid supports.[62-66] It can also be used to attach leashes onto affinity supports and for subsequent coupling of ligands. Useful spacers are diaminodipropylamine (DADPA),[62] ethylenediamine, hexanediamine,[63,64] 6-amino-caproic acid,[64,65] and any of several amino acids or peptides.[62] Useful solid supports for immobilization are agarose,[62-65] plastic,[62] or cellulose matrices.[64] Leashes become necessary to overcome steric effects when the ligand is immobilized too near the matrix to allow access by the molecule to be bound. Steric effects are usually most pronounced when the ligand is a small molecule. Reaction times are generally in the range of 1-3 hours for EDC coupling of molecules to solid supports. The amide bond formed by EDC coupling is relatively stable, especially at neutral pH.

Heterobifunctional cross-linkers that can be reacted in two-steps are often more useful and efficient for producing solid-phase supports than homobifunctional cross-linkers. Amine-activated supports can be converted to sulfhydryl-reactive supports using NHS-ester maleimide cross-linkers such as Sulfo-SMCC (Product #'s 22522, 22322). For some compounds that are difficult to immobilize, it may be possible to use NHS-ester, photoactivatable, phenyl azides to attach them to amine-activated supports. The photoactivatable, phenyl azide is unreactive in the dark but, once exposed to the appropriate wavelength range of light, it becomes extremely reactive and able to nonselectively couple to almost any ligand.

The cross-linker DMP (Product #20666) has been employed in the production of immobilized antibodies on protein A or protein G columns for use as antigen purification supports.[39] After antibody binds to the Fc-binding proteins, most or all of the antibody can be oriented so that the Fab region is available for antigen recognition. DMP is applied to the bound antibody column to link the two proteins through primary amines.

References

39. Schneider, C., Newman, R.A., Sutherland, D.R., Asser, U. and Greaves, M.F. (1982). A one-step purification of membrane proteins using a high efficiency immunomatrix. *J. Biol. Chem.* 257(18), 10766-10769.
62. Hermanson, G.T., Mallia, A.K. and Smith, P.K. (1992). *Immobilized Affinity Ligand Techniques.* California: Academic Press.
63. Stevens, D.A., Schreurs, J., Ihle, J.N. and May, W.S. (1991). Characterization of three related murine interleukin-3 surface receptor proteins. *J. Biol. Chem.* 266(7), 4151-4158.
64. Martzen, M.R., McMullen, B.A., Smith, N.E., Fujikawa, K. and Peanasky, R.J. (1990). Primary structure of the major pepsin inhibitor from the intestinal parasitic nematode *Ascaris suum. Biochem.* 29, 7366-7372.
65. Burton, S.C., Haggarty, N.W. and Harding, D.R.K. (1991). Efficient substitution of 1,1'-carbonyldiimidazole activated cellulose and sepharose matrices with amino acyl spacer arms. *J. Chrom.* 587, 271-275.
66. Mazid, M.A. and Kaplan, M. (1991). Immunoadsorbents with synthetic oligosaccharide hapten representing blood group A substances. *Bioconjugate Chem.* 2, 32-37.

Pierce Chemical Technical Library cross-linking

Protein-Protein Conjugates

One of the most widely used applications for cross-linkers is the production of protein-protein conjugates. Biological assays require methods for detection, and one of the most common methods for quantitation of results is to conjugate an enzyme, fluorophore or other molecule to a protein that has affinity for one of the components in the biological system being studied. Antibody-enzyme conjugates (primary or secondary antibodies) are among the most common protein-protein conjugates used. Secondary antibodies are relatively inexpensive and are available from Pierce (see the Antibody Ordering Section of this catalog). However, enzyme labeled primary antibodies are usually expensive and can be difficult to obtain. Many researchers find it necessary to label their primary antibodies.

There are many reagents used for the production of antibody-enzyme conjugates. These have been produced by glutaraldehyde cross-linking in one- and two-step procedures. These conjugates are easy to make but often yield conjugates that give high background in immunoassays. Carbohydrate moieties of antibodies can be oxidized and then coupled to primary amines on enzymes, such as horseradish peroxidase, in a procedure called reductive alkylation or amination. These conjugates give less background in enzyme immunoassays and are relatively easy to prepare. Some self-conjugation of antibody may occur in the protocol. Homobifunctional NHS-ester or imidoester cross-linkers can be substituted for glutaraldehyde in a one-step protocol; however, polymerization and self-conjugation are still likely to occur. Homobifunctional sulfhydryl-reactive cross-linkers such as BMH (Product #22319) and DPDPB (Product #21701) may be useful if both proteins to be conjugated contain sulfhydryls.

Heterobifunctional cross-linkers are perhaps the best choices for antibody-enzyme or other protein-to-protein cross-linking. Unwanted self-conjugation inherent when using homobifunctional NHS-ester reagents or glutaraldehyde can be avoided when using a reagent such as SMCC (Product #'s 22321, 22320) or Sulfo-SMCC (Product #'s 22522, 22322). Sulfo-SMCC is conjugated to one protein, and the second is thiolated with SATA (Product #26102) or Traut's Reagent (Product #26101). Alternatively, disulfides in the protein are reduced, and the two activated proteins are incubated together to form conjugates that are free of dimers of either protein. Any of the other NHS-ester maleimide or pyridyl disulfide cross-linkers can be substituted for Sulfo-SMCC in this reaction scheme. Heterobifunctional photoactivatable phenylazide cross-linkers are seldom used for making protein-protein conjugates because conjugation efficiencies

Pierce Chemical Technical Library cross-linking

DNA/RNA Cross-linking to Proteins

Cross-linking of DNA or RNA to proteins is more limited because the reactivities of most cross-linkers favor protein-protein cross-linking over protein-DNA cross-linking. To assist in these cross-linking methods, DNA probes are often synthesized with primary amines or thiols attached to specific bases. After insertion of the bases into DNA, amine- or sulfhydryl-reactive cross-linkers can be used for their conjugation to proteins. EDC (Product #'s 22980, 22981) has been reportedly used to cross-link RNA to ribosomal protein subunits. Other specialized chemistries are reviewed in Wong's book, *Chemistry of Protein Conjugation and Cross-linking* (Product #15010).

Pierce Chemical Technical Library cross-linking

Other Applications

There are many additional applications for cross-linkers that are either antiquated methods, new technologies or for more specialized needs. Older methods for peptide synthesis involve use of carbodiimide cross-linkers such as DCC (Product #20320) and EDC (Product #'s 22980, 22981) for the step-wise addition of individual amino acids to support bound peptides. Cross-linkers such as glutaraldehyde and dimethylpimelimidate have been used for tissue fixation. Newer cross-linkers are being developed that have more than two functional groups. Some trifunctionals are already reported in the literature.

What is claimed is:

1. A conjugate comprising a carrier substituted with one or more occurrences of a moiety having the structure:

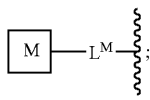

wherein each occurrence of M is independently a pharmaceutically useful modifier; the carrier comprises a biodegradable biocompatible polymer selected from polyacetals or polyketals and the molecular weight of the carrier is between about 0.5 and about 1500 kDa;

wherein at least a subset of the polyacetal repeat structural units have the following chemical structure:

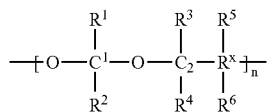

wherein for each occurrence of the n bracketed structure, one of $R^1$ and $R^2$ is hydrogen, and the other is a biocompatible group and includes a carbon atom covalently attached to $C^1$; $R^x$ includes a carbon atom covalently attached to $C^2$; n is an integer; each occurrence of $R^3$, $R^4$, $R^5$ and $R^6$ is a biocompatible group and is independently hydrogen or an organic moiety; and for each occurrence of the bracketed structure n, at least one of $R^1$, $R^2$, $R^3$, $R^4$, $R^5$ and $R^6$ comprises a carbonyl group suitable for oxime formation;

wherein at least a subset of the polyketal repeat structural units have the following chemical structure:

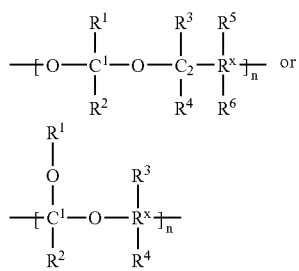

wherein each occurrence of $R^{1a}$ and $R^{2a}$ is a biocompatible group and includes a carbon atom covalently attached to $C^1$, and at least one of $R^{1a}$, $R^{2a}$, $R^3$, $R^4$, $R^5$ and $R^6$ comprises a carbonyl group suitable for oxime formation and each occurrence of $L^M$ is independently an oxime-containing linker.

2. The conjugate of claim 1, wherein each occurrence of $L^M$ is independently a moiety having the structure:

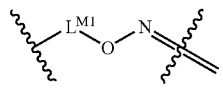

wherein each occurrence of $L^{M1}$ is independently a substituted or unsubstituted, cyclic or acyclic, linear or branched $C_{0-12}$alkylidene or $C_{0-12}$alkenylidene moiety wherein up to two non-adjacent methylene units are independently optionally replaced by CO, $CO_2$, COCO, $CONR^{Z1}$, $OCONR^{Z1}$, $NR^{Z1}NR^{Z2}$, $NR^{Z1}NR^{Z2}CO$, $NR^{Z1}CO$, $NR^{Z1}CO_2$, $NR^{Z1}CONR^{Z2}$, SO, $SO_2$, $NR^{Z1}SO_2$, $SO_2NR^{Z1}$, $NR^{Z1}SO_2NR^{Z2}$, O, S, or $NR^{Z1}$ wherein each occurrence of $R^{Z1}$ and $R^{Z2}$ is independently hydrogen, alkyl, heteroalkyl, aryl, heteroaryl or acyl.

3. The conjugate of claim 2, wherein one or more occurrences of $L^{M1}$ independently comprises a maleimide-containing crosslinker.

4. The conjugate of claim 3, wherein one or more occurrences of $L^{M1}$ independently comprises a 4-(N-maleimidomethyl)cyclohexane-1-carboxylate, m-maleimidobenzoyl or a 4-(p-maleimidophenyl)butyrate crosslinker.

5. The conjugate of claim 1, wherein one or more occurrences of M comprises, or is attached to the carrier through, a biodegradable bond.

6. The conjugate of claim 4, wherein the biodegradable bond is selected from the group consisting of acetal, ketal, amide, ester, thioester, enamine, imine, imide, dithio, and phosphoester bond.

7. The conjugate of claim 1, wherein the carrier is a biodegradable biocompatible polyacetal wherein at least a subset of the polyacetal repeat structural units have the following chemical structure:

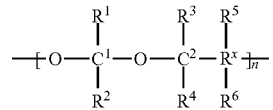

wherein for each occurrence of the n bracketed structure, one of $R^1$ and $R^2$ is hydrogen, and the other is a biocompatible group and includes a carbon atom covalently attached to $C^1$; $R^x$ includes a carbon atom covalently attached to $C^2$; n is an integer; each occurrence of $R^3$, $R^4$, $R^5$ and $R^6$ is a biocompatible group and is independently hydrogen or an organic moiety; and for each occurrence of the bracketed structure n, at least one of $R^1$, $R^2$, $R^3$, $R^4$, $R^5$ and $R^6$ comprises a carbonyl group suitable for oxime formation.

8. The conjugate of claim 1, wherein the carrier is a biodegradable biocompatible polyketal wherein at least a subset of the polyketal repeat structural units have the following chemical structure:

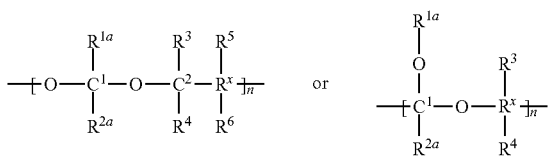

wherein each occurrence of $R^{1a}$, and $R^{2a}$ is a biocompatible group and includes a carbon atom covalently attached to $C^1$; $R^x$ includes a carbon atom covalently attached to $C^2$; n is an integer; each occurrence of $R^3$, $R^4$, $R^5$ and $R^6$ is a biocompatible group and is independently hydrogen or an organic moiety; and for each occurrence of the bracketed structure n, at least one of $R^{1a}$, $R^{2a}$, $R^3$, $R^4$, $R^5$ and $R^6$ comprises a carbonyl group suitable for oxime formation.

9. The conjugate of claim 8, wherein one or more occurrence of M is selected from the group consisting of proteins, antibodies, antibody fragments, peptides, antineoplastic drugs, hormones, cytokines, enzymes, enzyme substrates, receptor ligands, lipids, nucleotides, nucleosides, metal complexes, cations, anions, amines, heterocycles, heterocyclic amines, aromatic groups, aliphatic groups, intercalators, antibiotics, antigens, immunomodulators, and antiviral compounds.

10. The conjugate of claim 1, wherein the conjugate is water-soluble.

11. The conjugate of claim 1, wherein the conjugate comprises a pharmaceutically useful modifier and a detectable label.

12. A composition comprising the conjugate of claim 1 and a pharmaceutically suitable carrier or diluent.

13. A composition comprising a conjugate of claim 1 associated with an effective amount of a therapeutic agent; wherein the therapeutic agent is incorporated into and released from said conjugate matrix by degradation of the conjugate matrix or diffusion of the agent out of the matrix over a period of time.

14. The composition of claim 13 wherein said conjugate is further associated with a diagnostic label.

15. The conjugate of claim 4, wherein one or more occurrences of $L^{M1}$ independently comprises a 4-(N-maleimidomethyl)cyclohexane-1-carboxylate crosslinker.

16. The conjugate of claim 4, wherein one or more occurrences of $L^{M1}$ independently comprises a m-maleimidobenzoyl crosslinker.

17. The conjugate of claim 4, wherein one or more occurrences of $L^{M1}$ independently comprises a 4-(p-maleimidophenyl)butyrate crosslinker.

18. The conjugate of claim 1, wherein the molecular weight of the carrier is between about 1 and about 1000 kDa.

19. The conjugate of claim 7, wherein the molecular weight of the carrier is between about 1 and about 1000 kDa.

20. The conjugate of claim 8, wherein the molecular weight of the carrier is between about 1 and about 1000 kDa.

21. The conjugate of claim 1, wherein the carrier is hydrophilic.

22. The conjugate of claim 7, wherein the carrier is hydrophilic.

23. The conjugate of claim 8, wherein the carrier is hydrophilic.

* * * * *

UNITED STATES PATENT AND TRADEMARK OFFICE
CERTIFICATE OF CORRECTION

PATENT NO. : 8,030,459 B2
APPLICATION NO. : 10/521334
DATED : October 4, 2011
INVENTOR(S) : Papisov et al.

Page 1 of 3

It is certified that error appears in the above-identified patent and that said Letters Patent is hereby corrected as shown below:

In column 1, beginning at line 6 and ending at line 12, please delete:

"The present application claims the benefit under 35 U.S.C. § 371 of International Application No.: PCT/US03/33584 (published PCT application No. WO 04/09082), filed July 18, 2003, which claims priority to U.S. Patent Application Number 60/397,283, filed July 19, 2002, the entire contents of each of the above cited applications are incorporated herein by reference."

and insert:

--The present application claims the benefit under 35 U.S.C. § 371 of International Application No.: PCT/US03/22584 (published PCT application No. WO 04/09082), filed July 18, 2003, which claims priority to U.S. Patent Application Number 60/397,283, filed July 19, 2002, the entire contents of each of the above cited applications are incorporated herein by reference.--

In column 1, beginning at line 16 and ending at line 21, please delete:

"The present invention was made with support, in part, from a grant from the National Center for Research Resources of the National Institutes of Health (Number R21-RR14221) and a DoE grant (Number DE-FG02-00ER63057). Accordingly, the United States Government may have certain rights in this invention."

and insert:

--The present invention was made with support, in part, from a grant from the National Center for Research Resources of the National Institutes of Health (Number R21-RR14221) and a DoE grant (Number DE-FG02-00ER63057). Accordingly, the United States Government has certain rights in this invention.--

Signed and Sealed this
Twentieth Day of November, 2012

David J. Kappos
*Director of the United States Patent and Trademark Office*

CERTIFICATE OF CORRECTION (continued)
U.S. Pat. No. 8,030,459 B2

In claim 1, column 137, beginning at line 20 and ending at line 25, please delete the structure:

" 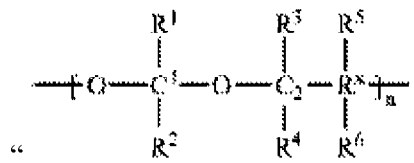 " and insert the structure: -- 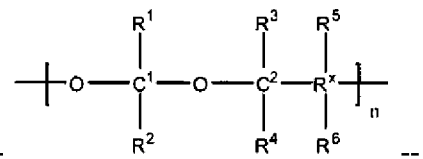 --

In claim 1, column 137, beginning at line 40 and ending at line 50, please delete the structures:

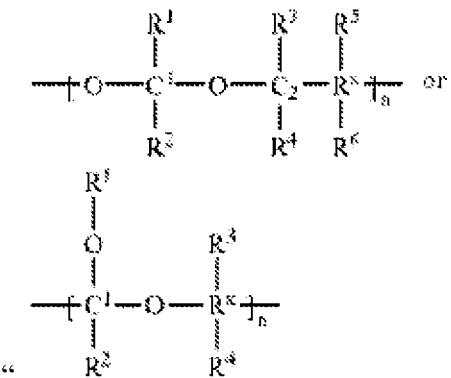

and insert the structures:

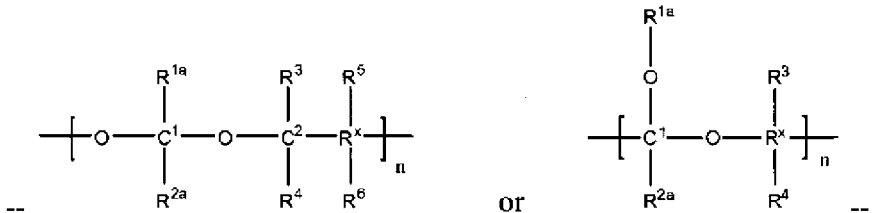 --

In claim 3, column 138, beginning at line 13 and ending at line 15, please delete:

"The conjugate of claim 2, wherein one or more occurrences of $L^{M1}$ independently comprises a maleimide-containing crosslinker."

and insert:

--The conjugate of claim 1, wherein one or more occurrences of $L^{M1}$ independently comprises a maleimide-containing crosslinker.--

CERTIFICATE OF CORRECTION (continued)
U.S. Pat. No. 8,030,459 B2

In claim 6, column 138, beginning at line 23 and ending at line 26, please delete:

"The conjugate of claim 4, wherein the biodegradable bond is selected from the group consisting of acetal, ketal, amide, ester, thioester, enamine, imine, imide, dithio, and phosphoester bond."

and insert:

--The conjugate of claim 5, wherein the biodegradable bond is selected from the group consisting of acetal, ketal, amide, ester, thioester, enamine, imine, imide, dithio, and phosphoester bond.--